US006307123B1

(12) United States Patent
Kriz et al.

(10) Patent No.: US 6,307,123 B1
(45) Date of Patent: Oct. 23, 2001

(54) METHODS AND COMPOSITIONS FOR TRANSGENE IDENTIFICATION

(75) Inventors: Alan L. Kriz, Gales Ferry; T. Michael Spencer, Mystic, both of CT (US)

(73) Assignee: Dekalb Genetics Corporation, Dekalb, IL (US)

( * ) Notice: Subject to any disclaimer, the term of this patent is extended or adjusted under 35 U.S.C. 154(b) by 0 days.

(21) Appl. No.: 09/080,625

(22) Filed: May 18, 1998

(51) Int. Cl.$^7$ .......................... C12N 15/00; C12M 15/09; A01H 5/00; A01H 1/02
(52) U.S. Cl. .......................... 800/282; 800/266; 800/288; 800/300; 800/301; 536/23.4; 536/24.1
(58) Field of Search .................................. 536/24.1, 23.4; 435/69.1, 172.3, 410, 411, 419, 430.1; 800/278, 266, 282, 288, 200, 301

(56) References Cited

U.S. PATENT DOCUMENTS

| 4,946,046 | * | 8/1990 | Affleck et al. . | |
|---|---|---|---|---|
| 5,474,929 | | 12/1995 | Pelcher | 435/240.4 |
| 5,525,716 | * | 6/1996 | Roger et al. . | |
| 5,550,318 | | 8/1996 | Adams et al. . | |

FOREIGN PATENT DOCUMENTS

| 2032443 | 6/1991 | (CA) . |
|---|---|---|
| WO 91/0259 | 2/1991 | (WO) . |
| WO 92/17593 | 10/1992 | (WO) . |
| WO 94/09699 | 5/1994 | (WO) . |
| WO 95/23230 | 8/1995 | (WO) . |
| WO 95/34634 | 12/1995 | (WO) . |
| WO 97/41228 | 11/1997 | (WO) . |
| WO 98/16824 | 4/1998 | (WO) . |

OTHER PUBLICATIONS

Xu et al. FEMS Microbiol Letter. 1991. vol. 1: 55–59.*
Alonso. Gene. 1988. vol. 30: 325–326.*
Napoli et al. The Plant Cell. 1989. vol. 2: 278–289.*
Dekeyser et al. The Plant Cell. 1990. vol. 2: 591–602.*
Bennett et al., "Fusion of green fluorescent protein witht he Zeocin™–resistant marker allows visual screening and drug selection of transfected eukaryotic cells," *BioTechniques*, 24:478–482, Mar. 1998.
Barnes, "Variable patterns of expression of luciferase in transgenic tobacco leaves," *Proc. Natl. Acad. Sci. USA*, 87:9183–9187, 1990.
Beck et al., "Nucleotide sequence and exact localization of the neomycin phosphotransferase gene from transposon Tn5," *Gene*, 9:327–336, 1982.
Chalfie et al., "Green fluorescent protein as a marker for gene expression," *Science*, 263:725–888, 1994.
Chiu et al., "Engineered GFP as a vital reporter in plants," *Curr. Biol.*, 6:325–330, 1996.
Cody et al., "Chemical structure of the hexapeptide chromophore of the Aequorea green fluorescent protein," *Biochemistry*, 32:1212–1218, 1993.

Cormack et al., "FACS optimized mutants of the green fluorescent protein (GFP)," *Gene*, 173:33–38, 1996.
Dhaese et al., "Identification of sequences involved in polyadenylation of higher plant nuclear transcripts using Agrobacterium T–DNA genes as models," *EMBO J.*, 2:419–426, 1983.
Fodor et al., "Light–directed, spatially addressable parallel chemical synthesis," *Science*, 251:767–773, 1991.
Haseloff and Amos, "GFP in plants," *Trends Genet*, 11:328–329, 1995.
Haseloff et al., "Removal of a cryptic intron and subcellular localization of green fluorescent protein are required to mark transgenic Arabidopsis plants brightly," *Proc. Natl. Acad. Sci., USA*, 94:2122–2127, 1997.
Heim and Tsien, "Engineering green fluorescent protein for improved brightness, longer wavelengths and fluorescence resonance energy transfer," *Curr. Biol.*, 6:178–182, 1996.
Heim et al., "Improved green fluorescence," *Nature*, 373:663–664, 1995.
Heim et al., "Wavelength mutations and postranslational autoxidation of green fluorescent protein," *Proc. Natl. Acad. Sci., USA*, 91:12501–12504, 1994.
Hinchee et al., "Production of transgenic soybean plants using Agrobacterium–mediated DNA transfer," *Bio/technol.*, 6:915–922, 1988.
Hu and Cheng, "Expression of Aequorea green fluorescent protein in plant cells," *FEBS Lett.*, 369:331–334, 1995.
Kaether and Gerdes, "Visualization of protein transport along the secretory pathway using green fluorescence protein," *FEBS Lett.*, 369:267–271, 1995.
Lee and Huang, "Genes encoding oleosins in maize kernel of inbreds Mo 17 and B73," *Plant Molecular Biology*, 26:1981–1987, 1994.
Leite et al., "Nucleotide sequence of a cDNA clone encoding γ–coixin from *Coix lacryma–jobi* seeds," *Plant Physiology*, 97:1604–1605, 1991.

(List continued on next page.)

*Primary Examiner*—Paula Hutzell
(74) *Attorney, Agent, or Firm*—Fulbright&Jaworski LLP

(57) ABSTRACT

The present invention provides methods and compositions for the identification of transgenic seeds. This is accomplished by use of screenable markers linked to aleurone-specific promoters. The screenable markers can be provided as gene fusions with selectable markers, allowing both selection and screening of transformants. The use of aleurone-specific promoters, which also direct expression in embryogenic tissues, allows efficient selection of transgenic cells and the screening of viable transgenic seeds, while avoiding the deleterious effects associated with constitutive expression of screenable marker genes. Screening of transgenic seeds avoids the need for growing and assaying of seeds for transgenes and allows implementation of automated seed screening techniques for the identification of transgenic seeds.

69 Claims, 6 Drawing Sheets

OTHER PUBLICATIONS

Lybarger et al., "Rapid Generation and Flow Cytometric Analysis of Stable GFP–Expressing Cells," *Cytometry,* 25:211–220, 1996.

McElroy et al., "Isolation of an efficient actin promoter for use in rice transformation," *Plant Cell,* 2(2):163–171, 1990.

Millar et al., "The regulation of circadian period by phototransduction pathways in Arabidopsis," *Science,* 267:1161–1163, 1995.

Ow et al., "Transient and stable expression of the firefly luciferase gene in plant cells and transgenic plants," *Science,* 234:856–859, 1986.

Pang et al., "An improved green fluorescent protein gene as a vital marker in plants," *Plant Physiol.,* 112:893–900, 1996.

Plautz et al., "Green fluorescent protein and its derivatives as versatile markers for gene expression in living *Drosophila melanogaster,* plant and mammalian cells," *Gene,* 173:83–87, 1996.

Potrykus et al., "Direct gene transfer to cells of a graminaceous monocot," *Mol. Gen. Genet.,* 199:183–188, 1985.

Prasher et al., "Primary structure of the *Aequorea victoria* green fluorescent protein," *Gene,* 111:229–233, 1992.

Reichel et al., "Enhanced green fluorescence by the expression of an *Aequorea victoria* green fluorescent protein mutant in mono– and dicotyledonous plant cells," *Proc. Natl. Acad. Sci., USA,* 93:5888–5893, 1996.

Sheen et al., "Green fluorescent protein as a new vital marker in plant cells," *Plant J.,* 8(5):777–784, 1995.

Stalker et al., "Purification and properties of a nitrilase specific for the herbicide bromoxynil and corresponding nucleotide sequence analysis of the bxn gene," *J Biol. Chem.,* 263(13):6310–6314, 1988.

Thillet et al., "Site–directed mutagenesis of mouse dihydrofolate reductase," *J. Biol. Chem.,* 263:12500–12508, 1988.

Tian et al., "Expression of the green fluorescent protein gene in conifer tissues," *Plant Cell Rep.,* 16:267–271, 1997.

Yang et al., "Optimized codon usage and chromophore mutations provide enhanced sensitivity with the green fluorescent protein," *Nucleic Acid Res.,* 24:4592–4593, 1996.

Co–pending U.S. Patent Application Serial No. 08/113,561, filed Aug. 25, 1993 (DEKM:055).

* cited by examiner

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 1701 base pairs
      (B) TYPE: nucleic acid
      (C) STRANDEDNESS: double
      (D) TOPOLOGY: linear (xi) SEQUENCE DESCRIPTION: SEQ ID NO:1:

```
ATGGGCAAGG GCGAGGAACT GTTCACTGGC GTGGTCCCAA TCCTGGTGGA ACTGGATGGT      60

GATGTGAACG GGCACAAGTT CTCCGTCAGC GGCGCGGGTG AAGGTGATGC CACCTACGGA     120

AAGCTCACCC TGAAGTTCAT CTGCACTACC GGAAAGCTCC CTGTTCCGTG GCCAACCCTC     180

GTCACCACTT TCAGCTACGG TGTTCAGTGC TTCTCCCGGT ACCCAGATCA CATGAAGCAG     240

CATGACTTCT TCAAGAGCGC CATGCCCGAA GGCTACGTGC AAGAAAGGAC TATCTTCTTC     300

AAGGATGACG GGAACTACAA GACACGTGCC GAAGTCAAGT TCGAAGGTGA TACCCTGGTG     360

AACCGCATCG AGCTGAAAGG TAAGTTTCTG CTTCTACCTT TGATATATAT ATAATAATTA     420

TCATTAATTA GTAGTAATAT AATATTTCAA ATATTTTTTT CAAAATAAAA GAATGTAGTA     480

TATAGCAATT GCTTTTCTGT AGTTTATAAG TGTGTATATT TTAATTTATA ACTTTTCTAA     540

TATATGACCA AAATTTGTTG ATGTGCAGGT ATCGATTTCA AGGAAGATGG AAACATCCTC     600

GGACACAAGC TGGAGTACAA CTACAACTCC CACAACGTAT ACATCATGGC CGACAAGCAG     660

AAGAACGGCA TCAAGGTGAA CTTCAAGATC AGGCACAACA TCGAAGATGG AAGCGTGCAA     720

CTGGCGGACC ACTACCAGCA GAACACGCCC ATCGGCGATG GCCCTGTCCT GCTGCCGGAC     780

AACCATTACC TGTCCACGCA ATCTGCCCTC TCCAAGGACC CCAACGAGAA GAGGGACCAC     840

ATGGTCCTGC TGGAGTTCGT GACGGCTGCT GGGATCACGC ATGGCATGGA TGAACTCTAC     900

AAGGGATCCA TTGAACAAGA TGGATTGCAC GCAGGTTCTC CGGCCGCTTG GGTGGAGAGG     960

CTATTCGGCT ATGACTGGGC ACAACAGACA ATCGGCTGCT CTGATGCCGC CGTGTTCCGG    1020

CTGTCAGCGC AGGGGCGCCC GGTTCTTTTT GTCAAGACCG ACCTGTCCGG TGCCCTGAAT    1080

GAACTGCAGG ACGAGGCAGC GCGGCTATCG TGGCTGGCCA CGACGGGCGT TCCTTGCGCA    1140

GCTGTGCTCG ACGTTGTCAC TGAAGCGGGA AGGGACTGGC TGCTATTGGG CGAAGTGCCG    1200
```

-continued

```
GGGCAGGATC TCCTGTCATC TCACCTTGCT CCTGCCGAGA AAGTATCCAT CATGGCTGAT      1260

GCAATGCGGC GGCTGCATAC GCTTGATCCG GCTACCTGCC CATTCGACCA CCAAGCGAAA      1320

CATCGCATCG AGCGAGCACG TACTCGGATG GAAGCCGGTC TTGTCGATCA GGATGATCTG      1380

GACGAAGAGC ATCAGGGGCT CGCGCCAGCC GAACTGTTCG CCAGGCTCAA GGCGCGCATG      1440

CCCGACGGCG AGGATCTCGT CGTGACCCAT GGCGATGCCT GCTTGCCGAA TATCATGGTG      1500

GAAAATGGCC GCTTTTCTGG ATTCATCGAC TGTGGCCGGC TGGGTGTGGC GGACCGCTAT      1560

CAGGACATAG CGTTGGCTAC CCGTGATATT GCTGAAGAGC TTGGCGGCGA ATGGGCTGAC      1620

CGCTTCCTCG TGCTTTACGG TATCGCCGCT CCCGATTCGC AGCGCATCGC CTTCTATCGC      1680

CTTCTTGACG AGTTCTTCTG A                                                1701

(2) INFORMATION FOR SEQ ID NO:2:

(i) SEQUENCE CHARACTERISTICS:
        (A) LENGTH: 3336 base pairs
        (B) TYPE: nucleic acid
        (C) STRANDEDNESS: double
        (D) TOPOLOGY: linear (xi) SEQUENCE DESCRIPTION: SEQ ID NO:2:

CTCGAGGTCA CTAAGCAACT AACTTTGAGG AATGAGGTGA TGATGAATTA ACTCACTCCA        60

TTCCACAAAC CAAACAAAAA TTTGAGGAGT GAGAAGATGA TTGACTATCT CATTCCTCAA       120

ACCAAACACC TCAAATATAT CTGCTATCGG GATTGGCATT CCTGTATCCC TACGCCCGTG       180

TACCCCCTGT TTAGAGAACC TCCAAAGGTA TAAGATGGCG AAGATTATTG TTGTCTTGTC       240

TTTCATCATA TATCGAGTCT TTCCCTAGGA TATTATTATT GGCAATGAGC ATTACACGGT       300

TAATCGATTG AGAGAACATG CATCTCACCT TCAGCAAATA ATTACGATAA TCCATATTTT       360

ACGCTTCGTA ACTTCTCATG AGTTTCGATA TACAAATTTG TTTTCTGGAC ACCCTACCAT       420

TCATCCTCTT CGGAGAAGAG AGGAAGTGTC CTCAATTTAA ATATGTTGTC ATGCTGTAGT       480

TCTTCACAAA ATCTCAACAG GTACCAAGCA CATTGTTTCC ACAAATTATA TTTTAGTCAC       540

AATAAATCTA TATTATTATT AATATACTAA AACTATACTG ACGCTCAGAT GCTTTTACTA       600

GTTCTTGCTA GTATGTGATG TAGGTCTACG TGGACCAGAA AATAGTGAGA CACGGAAGAC       660

AAAAGAAGTA AAAGAGGCCC GGACTACGGC CCACATGAGA TTCGGCCCCG CCACCTCCGG       720

CAACCAGCGG CCGATCCAAC GGCAGTGCGC GCACACACAC AACCTCGTAT ATATCGCCGC       780

GCGGAAGCGG CGCGACCGAG GAAGCCTTGT CCTCGACACC CCCTACACAG GTGTCGCGCT       840

GCCCCCGACA CGAGTCCCGC ATGCGTCCCA CGCGGCCGCG CCAGATCCCG CCTCCGCGCG       900

TTGCCACGCC CTCTATAAAC ACCCAGCTCT CCCTCGCCCT CATCTACCTC ACTCGTAGTC       960

GTAGCTCAAG CATCAGCGGC AGCGGCAGCG GCAGGATCTC TGGGCAGCGT GCGCACGTGG      1020

GGTATCTAGC TCGCTCTGCT AGCCTACCAA TCGAATTAAT TCGGCTTAAC CATGGGCAAG      1080

GGCGAGGAAC TGTTCACTGG CGTGGTCCCA ATCCTGGTGG AACTGGATGG TGATGTGAAC      1140

GGGCACAAGT TCTCCGTCAG CGGCGCGGGT GAAGGTGATG CCACCTACGG AAAGCTCACC      1200

CTGAAGTTCA TCTGCACTAC CGGAAAGCTC CCTGTTCCGT GGCCAACCCT CGTCACCACT      1260

TTCAGCTACG GTGTTCAGTG CTTCTCCCGG TACCCAGATC ACATGAAGCA GCATGACTTC      1320

TTCAAGAGCG CCATGCCCGA AGGCTACGTG CAAGAAAGGA CTATCTTCTT CAAGGATGAC      1380

GGGAACTACA AGACACGTGC CGAAGTCAAG TTCGAAGGTG ATACCCTGGT GAACCGCATC      1440

GAGCTGAAAG GTAAGTTTCT GCTTCTACCT TTGATATATA TATAATAATT ATCATTAATT      1500
```

-continued

```
AGTAGTAATA TAATATTTCA AATATTTTTT TCAAAATAAA AGAATGTAGT ATATAGCAAT    1560

TGCTTTTCTG TAGTTTATAA GTGTGTATAT TTTAATTTAT AACTTTTCTA ATATATGACC    1620

AAAATTTGTT GATGTGCAGG TATCGATTTC AAGGAAGATG GAAACATCCT CGGACACAAG    1680

CTGGAGTACA ACTACAACTC CCACAACGTA TACATCATGG CCGACAAGCA GAAGAACGGC    1740

ATCAAGGTGA ACTTCAAGAT CAGGCACAAC ATCGAAGATG GAAGCGTGCA ACTGGCGGAC    1800

CACTACCAGC AGAACACGCC ATCGGCGAT GGCCCTGTCC TGCTGCCGGA CAACCATTAC     1860

CTGTCCACGC AATCTGCCCT CTCCAAGGAC CCCAACGAGA GAGGGACCA CATGGTCCTG     1920

CTGGAGTTCG TGACGGCTGC TGGGATCACG CATGGCATGG ATGAACTCTA CAAGGGATCC    1980

ATTGAACAAG ATGGATTGCA CGCAGGTTCT CCGGCCGCTT GGGTGGAGAG GCTATTCGGC    2040

TATGACTGGG CACAACAGAC AATCGGCTGC TCTGATGCCG CCGTGTTCCG GCTGTCAGCG    2100

CAGGGGCGCC CGGTTCTTTT TGTCAAGACC GACCTGTCCG GTGCCCTGAA TGAACTGCAG    2160

GACGAGGCAG CGCGGCTATC GTGGCTGGCC ACGACGGGCG TTCCTTGCGC AGCTGTGCTC    2220

GACGTTGTCA CTGAAGCGGG AAGGGACTGG CTGCTATTGG GCGAAGTGCC GGGGCAGGAT    2280

CTCCTGTCAT CTCACCTTGC TCCTGCCGAG AAAGTATCCA TCATGGCTGA TGCAATGCGG    2340

CGGCTGCATA CGCTTGATCC GGCTACCTGC CCATTCGACC ACCAAGCGAA ACATCGCATC    2400

GAGCGAGCAC GTACTCGGAT GGAAGCCGGT CTTGTCGATC AGGATGATCT GGACGAAGAG    2460

CATCAGGGGC TCGCGCCAGC CGAACTGTTC GCCAGGCTCA AGGCGCGCAT GCCCGACGGC    2520

GAGGATCTCG TCGTGACCCA TGGCGATGCC TGCTTGCCGA ATATCATGGT GGAAAATGGC    2580

CGCTTTTCTG GATTCATCGA CTGTGGCCGG CTGGGTGTGG CGGACCGCTA TCAGGACATA    2640

GCGTTGGCTA CCCGTGATAT TGCTGAAGAG CTTGGCGGCG AATGGGCTGA CCGCTTCCTC    2700

GTGCTTTACG GTATCGCCGC TCCCGATTCG CAGCGCATCG CCTTCTATCG CCTTCTTGAC    2760

GAGTTCTTCT GAGAGCTCGG TACCAAGCTG GGATCGATG AGCTAAGCTA GCTATATCAT     2820

CAATTTATGT ATTACACATA ATATCGCACT CAGTCTTTCA TCTACGGCAA TGTACCAGCT    2880

GATATAATCA GTTATTGAAA TATTTCTGAA TTTAAACTTG CATCAATAAA TTTATGTTTT    2940

TGCTTGGACT ATAATACCTG ACTTGTTATT TTATCAATAA ATATTTAAAC TATATTTCTT    3000

TCAAGATATC ATTCTTTACA AGTATACGTG TTTAAATTGA ATACCATAAA TTTTTATTTT    3060

TCAAATACAT GTAAAATTAT GAAATGGGAG TGGTGGCGAC CGAGCTCAAG CACACTTCAA    3120

TTCCTATAAC GGACCAAATC GCAAAAATTA TAATAACATA TTATTTCATC CTGGATTAAA    3180

AGAAAGTCAC CGGGGATTAT TTTGTGACGC CGATTACATA CGGCGACAAT AAAGACATTG    3240

GAAATCGTAG TACATATTGG AATACACTGA TTATATTAAT GATGAATACA TACTTTAATA    3300

TCCTTACGTA GGATCGATCC GAATTTCGAC CTCGAG                              3336

(2) INFORMATION FOR SEQ ID NO:3:

(i) SEQUENCE CHARACTERISTICS:
        (A) LENGTH: 3153 base pairs
        (B) TYPE: nucleic acid
        (C) STRANDEDNESS: double
        (D) TOPOLOGY: linear (xi) SEQUENCE DESCRIPTION: SEQ ID NO:3:

CTCGAGGTCA CTAAGCAACT AACTTTGAGG AATGAGGTGA TGATGAATTA ACTCACTCCA     60

TTCCACAAAC CAAACAAAAA TTTGAGGAGT GAGAAGATGA TTGACTATCT CATTCCTCAA    120

ACCAAACACC TCAAATATAT CTGCTATCGG GATTGGCATT CCTGTATCCC TACGCCCGTG    180
```

-continued

```
TACCCCCTGT TTAGAGAACC TCCAAAGGTA TAAGATGGCG AAGATTATTG TTGTCTTGTC    240

TTTCATCATA TATCGAGTCT TTCCCTAGGA TATTATTATT GGCAATGAGC ATTACACGGT    300

TAATCGATTG AGAGAACATG CATCTCACCT TCAGCAAATA ATTACGATAA TCCATATTTT    360

ACGCTTCGTA ACTTCTCATG AGTTTCGATA TACAAATTTG TTTTCTGGAC ACCCTACCAT    420

TCATCCTCTT CGGAGAAGAG AGGAAGTGTC CTCAATTTAA ATATGTTGTC ATGCTGTAGT    480

TCTTCACAAA ATCTCAACAG GTACCAAGCA CATTGTTTCC ACAAATTATA TTTTAGTCAC    540

AATAAATCTA TATTATTATT AATATACTAA AACTATACTG ACGCTCAGAT GCTTTTACTA    600

GTTCTTGCTA GTATGTGATG TAGGTCTACG TGGACCAGAA AATAGTGAGA CACGGAAGAC    660

AAAAGAAGTA AAAGAGGCCC GGACTACGGC CCACATGAGA TTCGGCCCCG CCACCTCCGG    720

CAACCAGCGG CCGATCCAAC GGCAGTGCGC GCACACACAC AACCTCGTAT ATATCGCCGC    780

GCGGAAGCGG CGCGACCGAG GAAGCCTTGT CCTCGACACC CCCTACACAG GTGTCGCGCT    840

GCCCCCGACA CGAGTCCCGC ATGCGTCCCA CGCGGCCGCG CCAGATCCCG CCTCCGCGCG    900

TTGCCACGCC CTCTATAAAC ACCCAGCTCT CCCTCGCCCT CATCTACCTC ACTCGTAGTC    960

GTAGCTCAAG CATCAGCGGC AGCGGCAGCG GCAGGATCTC TGGGCAGCGT GCGCACGTGG   1020

GGTATCTAGC TCGCTCTGCT AGCCTACCAA TCGAATTAAT TCGGCTTCCG GCCATGGTGA   1080

GCAAGGGCGA GGAGCTGTTC ACCGGGGTGG TGCCCATCCT GGTCGAGCTG GACGGCGACG   1140

TAAACGGCCA CAAGTTCAGC GTGTCCGGCG AGGGCGAGGG CGATGCCACC TACGGCAAGC   1200

TGACCCTGAA GTTCATCTGC ACCACCGGCA AGCTGCCCGT GCCCTGGCCC ACCCTCGTGA   1260

CCACCCTGAC CTACGGCGTG CAGTGCTTCA GCCGCTACCC CGACCACATG AAGCAGCACG   1320

ACTTCTTCAA GTCCGCCATG CCCGAAGGCT ACGTCCAGGA GCGCACCATC TTCTTCAAGG   1380

ACGACGGCAA CTACAAGACC CGCGCCGAGG TGAAGTTCGA GGGCGACACC CTGGTGAACC   1440

GCATCGAGCT GAAGGGCATC GACTTCAAGG AGGACGGCAA CATCCTGGGG CACAAGCTGG   1500

AGTACAACTA CAACAGCCAC AACGTCTATA TCATGGCCGA CAAGCAGAAG AACGGCATCA   1560

AGGTGAACTT CAAGATCCGC CACAACACCG AGGACGGCAG CGTGCAGCTC GCCGACCACT   1620

ACCAGCAGAA CACCCCCATC GGCGACGGCC CCGTGCTGCT GCCCGACAAC CACTACCTGA   1680

GCACCCAGTC CGCCTTGAGC AAAGACCCCA ACGAGAAGCG CGATCACATG GTCCTGCTGG   1740

AGTTCGTGAC CGCCGCCGGG ATCACTCTCG GCATGGACGA GCTGTACAAG GGATCCATTG   1800

AACAAGATGG ATTGCACGCA GGTTCTCCGG CCGCTTGGGT GGAGAGGCTA TTCGGCTATG   1860

ACTGGGCACA ACAGACAATC GGCTGCTCTG ATGCCGCCGT GTTCCGGCTG TCAGCGCAGG   1920

GGCGCCCGGT TCTTTTTGTC AAGACCGACC TGTCCGGTGC CCTGAATGAA CTGCAGGACG   1980

AGGCAGCGCG GCTATCGTGG CTGGCCACGA CGGGCGTTCC TTGCGCAGCT GTGCTCGACG   2040

TTGTCACTGA AGCGGGAAGG GACTGGCTGC TATTGGGCGA AGTGCCGGGG CAGGATCTCC   2100

TGTCATCTCA CCTTGCTCCT GCCGAGAAAG TATCCATCAT GGCTGATGCA ATGCGGCGGC   2160

TGCATACGCT TGATCCGGCT ACCTGCCCAT TCGACCACCA AGCGAAACAT CGCATCGAGC   2220

GAGCACGTAC TCGGATGGAA GCCGGTCTTG TCGATCAGGA TGATCTGGAC GAAGAGCATC   2280

AGGGGCTCGC GCCAGCCGAA CTGTTCGCCA GGCTCAAGGC GCGCATGCCC GACGGCGAGG   2340

ATCTCGTCGT GACCCATGGC GATGCCTGCT TGCCGAATAT CATGGTGGAA AATGGCCGCT   2400

TTTCTGGATT CATCGACTGT GGCCGGCTGG GTGTGGCGGA CCGCTATCAG GACATAGCGT   2460

TGGCTACCCG TGATATTGCT GAAGAGCTTG GCGGCGAATG GGCTGACCGC TTCCTCGTGC   2520

TTTACGGTAT CGCCGCTCCC GATTCGCAGC GCATCGCCTT CTATCGCCTT CTTGACGAGT   2580
```

-continued

```
TCTTCTGAGA GCTCCCAAGC CGAATTGGGG ATCGATGAGC TAAGCTAGCT ATATCATCAA    2640

TTTATGTATT ACACATAATA TCGCACTCAG TCTTTCATCT ACGGCAATGT ACCAGCTGAT    2700

ATAATCAGTT ATTGAAATAT TTCTGAATTT AAACTTGCAT CAATAAATTT ATGTTTTTGC    2760

TTGGACTATA ATACCTGACT TGTTATTTTA TCAATAAATA TTTAAACTAT ATTTCTTTCA    2820

AGATATCATT CTTTACAAGT ATACGTGTTT AAATTGAATA CCATAAATTT TTATTTTTCA    2880

AATACATGTA AAATTATGAA ATGGGAGTGG TGGCGACCGA GCTCAAGCAC ACTTCAATTC    2940

CTATAACGGA CCAAATCGCA AAAATTATAA TAACATATTA TTTCATCCTG GATTAAAAGA    3000

AAGTCACCGG GGATTATTTT GTGACGCCGA TTACATACGG CGACAATAAA GACATTGGAA    3060

ATCGTAGTAC ATATTGGAAT ACACTGATTA TATTAATGAT GAATACATAC TTTAATATCC    3120

TTACGTAGGA TCGATCCGAA TTTCGACCTC GAG                                3153
```

(2) INFORMATION FOR SEQ ID NO:4:

(i) SEQUENCE CHARACTERISTICS:
        (A) LENGTH: 3877 base pairs
        (B) TYPE: nucleic acid
        (C) STRANDEDNESS: double
        (D) TOPOLOGY: linear (xi) SEQUENCE DESCRIPTION: SEQ ID NO:4:

```
CTCGAGGTCA CTAAGCAACT AACTTTGAGG AATGAGGTGA TGATGAATTA ACTCACTCCA      60

TTCCACAAAC CAAACAAAAA TTTGAGGAGT GAGAAGATGA TTGACTATCT CATTCCTCAA     120

ACCAAACACC TCAAATATAT CTGCTATCGG GATTGGCATT CCTGTATCCC TACGCCCGTG     180

TACCCCCTGT TTAGAGAACC TCCAAAGGTA TAAGATGGCG AAGATTATTG TTGTCTTGTC     240

TTTCATCATA TATCGAGTCT TTCCCTAGGA TATTATTATT GGCAATGAGC ATTACACGGT     300

TAATCGATTG AGAGAACATG CATCTCACCT TCAGCAAATA ATTACGATAA TCCATATTTT     360

ACGCTTCGTA ACTTCTCATG AGTTTCGATA TACAAATTTG TTTTCTGGAC ACCCTACCAT     420

TCATCCTCTT CGGAGAAGAG AGGAAGTGTC CTCAATTTAA ATATGTTGTC ATGCTGTAGT     480

TCTTCACAAA ATCTCAACAG GTACCAAGCA CATTGTTTCC ACAAATTATA TTTTAGTCAC     540

AATAAATCTA TATTATTATT AATATACTAA AACTATACTG ACGCTCAGAT GCTTTTACTA     600

GTTCTTGCTA GTATGTGATG TAGGTCTACG TGGACCAGAA AATAGTGAGA CACGGAAGAC     660

AAAAGAAGTA AAAGAGGCCC GGACTACGGC CCACATGAGA TTCGGCCCCG CCACCTCCGG     720

CAACCAGCGG CCGATCCAAC GGCAGTGCGC GCACACACAC AACCTCGTAT ATATCGCCGC     780

GCGGAAGCGG CGCGACCGAG GAAGCCTTGT CCTCGCACAC CCCTACACAG GTGTCGCGCT     840

GCCCCCGACA CGAGTCCCGC ATGCGTCCCA CGCGGCCGCG CCAGATCCCG CCTCCGCGCG     900

TTGCCACGCC CTCTATAAAC ACCCAGCTCT CCCTCGCCCT CATCTACCTC ACTCGTAGTC     960

GTAGCTCAAG CATCAGCGGC AGCGGCAGCG GCAGGATCTC TGGGCAGCGT GCGCACGTGG    1020

GGTATCTAGC TCGCTCTGCT AGCCTACCAA TCGAATTCGG TAACCACCCG CCCCTCTCCT    1080

CTTTCTTTCT CCGTTTTTTT TTTCCGTCTC GGTCTCGATC TTTGGCCTTG GTAGTTTGGG    1140

TGGGCGAGAG GCGGCTTCGT GCGCGCCCAG ATCGGTGCGC GGGAGGGGCG GGATCTCGCG    1200

GCTGGGGCTC TCGCCGGCGT GGATCCGGCC CGGATCTCGC GGGGAATGGG GCTCTCGGAT    1260

GTAGATCTGC GATCCGCCGT TGTTGGGGGA GATGATGGGG GGTTTAAAAT TTCCGCCATG    1320

CTAAACAAGA TCAGGAAGAG GGGAAAAGGG CACTATGGTT TATATTTTTA TATATTTCTG    1380

CTGCTTCGTC AGGCTTAGAT GTGCTAGATC TTTCTTTCTT CTTTTTGTGG GTAGAATTTG    1440
```

-continued

```
AATCCCTCAG CATTGTTCAT CGGTAGTTTT TCTTTTCATG ATTTGTGACA AATGCACCTC    1500

GTGCGGAGCT TTTTTGTAGG TAGAATTCCA GCACACTGGC GGCCGTTACT AGTGGATCCG    1560

AGCTCGGTAC CAAGCTTATC GATACCGTCG AGATCCCCAA TTCGGCTTAA CCATGGGCAA    1620

GGGCGAGGAA CTGTTCACTG GCGTGGTCCC AATCCTGGTG GAACTGGATG GTGATGTGAA    1680

CGGGCACAAG TTCTCCGTCA GCGGCGCGGG TGAAGGTGAT GCCACCTACG GAAAGCTCAC    1740

CCTGAAGTTC ATCTGCACTA CCGGAAAGCT CCCTGTTCCG TGGCCAACCC TCGTCACCAC    1800

TTTCAGCTAC GGTGTTCAGT GCTTCTCCCG GTACCCAGAT CACATGAAGC AGCATGACTT    1860

CTTCAAGAGC GCCATGCCCG AAGGCTACGT GCAAGAAAGG ACTATCTTCT TCAAGGATGA    1920

CGGGAACTAC AAGACACGTG CCGAAGTCAA GTTCGAAGGT GATACCCTGG TGAACCGCAT    1980

CGAGCTGAAA GGTAAGTTTC TGCTTCTACC TTTGATATAT ATATAATAAT TATCATTAAT    2040

TAGTAGTAAT ATAATATTTC AAATATTTTT TTCAAAATAA AAGAATGTAG TATATAGCAA    2100

TTGCTTTTCT GTAGTTTATA AGTGTGTATA TTTTAATTTA TAACTTTTCT AATATATGAC    2160

CAAAATTTGT TGATGTGCAG GTATCGATTT CAAGGAAGAT GGAAACATCC TCGGACACAA    2220

GCTGGAGTAC AACTACAACT CCCACAACGT ATACATCATG GCCGACAAGC AGAAGAACGG    2280

CATCAAGGTG AACTTCAAGA TCAGGCACAA CATCGAAGAT GGAAGCGTGC AACTGGCGGA    2340

CCACTACCAG CAGAACACGC CCATCGGCGA TGGCCCTGTC CTGCTGCCGG ACAACCATTA    2400

CCTGTCCACG CAATCTGCCC TCTCCAAGGA CCCCAACGAG AAGAGGGACC ACATGGTCCT    2460

GCTGGAGTTC GTGACGGCTG CTGGGATCAC GCATGGCATG GATGAACTCT ACAAGGGATC    2520

CATTGAACAA GATGGATTGC ACGCAGGTTC TCCGGCCGCT TGGGTGGAGA GGCTATTCGG    2580

CTATGACTGG GCACAACAGA CAATCGGCTG CTCTGATGCC GCCGTGTTCC GGCTGTCAGC    2640

GCAGGGGCGC CCGGTTCTTT TTGTCAAGAC CGACCTGTCC GGTGCCCTGA ATGAACTGCA    2700

GGACGAGGCA GCGCGGCTAT CGTGGCTGGC CACGACGGGC GTTCCTTGCG CAGCTGTGCT    2760

CGACGTTGTC ACTGAAGCGG GAAGGGACTG GCTGCTATTG GGCGAAGTGC CGGGGCAGGA    2820

TCTCCTGTCA TCTCACCTTG CTCCTGCCGA GAAAGTATCC ATCATGGCTG ATGCAATGCG    2880

GCGGCTGCAT ACGCTTGATC CGGCTACCTG CCCATTCGAC CACCAAGCGA AACATCGCAT    2940

CGAGCGAGCA CGTACTCGGA TGGAAGCCGG TCTTGTCGAT CAGGATGATC TGGACGAAGA    3000

GCATCAGGGG CTCGCGCCAG CCGAACTGTT CGCCAGGCTC AAGGCGCGCA TGCCCGACGG    3060

CGAGGATCTC GTCGTGACCC ATGGCGATGC CTGCTTGCCG AATATCATGG TGGAAAATGG    3120

CCGCTTTTCT GGATTCATCG ACTGTGGCCG GCTGGGTGTG GCGGACCGCT ATCAGGACAT    3180

AGCGTTGGCT ACCCGTGATA TTGCTGAAGA GCTTGGCGGC GAATGGGCTG ACCGCTTCCT    3240

CGTGCTTTAC GGTATCGCCG CTCCCGATTC GCAGCGCATC GCCTTCTATC GCCTTCTTGA    3300

CGAGTTCTTC TGAGAGCTCG GTACCAAGCT GGGGATCGAT GAGCTAAGCT AGCTATATCA    3360

TCAATTTATG TATTACACAT AATATCGCAC TCAGTCTTTC ATCTACGGCA ATGTACCAGC    3420

TGATATAATC AGTTATTGAA ATATTTCTGA ATTTAAACTT GCATCAATAA ATTTATGTTT    3480

TTGCTTGGAC TATAATACCT GACTTGTTAT TTTATCAATA AATATTTAAA CTATATTTCT    3540

TTCAAGATAT CATTCTTTAC AAGTATACGT GTTTAAATTG AATACCATAA ATTTTTATTT    3600

TTCAAATACA TGTAAAATTA TGAAATGGGA GTGGTGGCGA CCGAGCTCAA GCACACTTCA    3660

ATTCCTATAA CGGACCAAAT CGCAAAAATT ATAATAACAT ATTATTTCAT CCTGGATTAA    3720

AAGAAAGTCA CCGGGGATTA TTTTGTGACG CCGATTACAT ACGGCGACAA TAAAGACATT    3780
```

```
GGAAATCGTA GTACATATTG GAATACACTG ATTATATTAA TGATGAATAC ATACTTTAAT    3840

ATCCTTACGT AGGATCGATC CGAATTTCGA CCTCGAG                              3877

(2) INFORMATION FOR SEQ ID NO:5:

(i) SEQUENCE CHARACTERISTICS:
        (A) LENGTH: 3694 base pairs
        (B) TYPE: nucleic acid
        (C) STRANDEDNESS: double
        (D) TOPOLOGY: linear (xi) SEQUENCE DESCRIPTION: SEQ ID NO:5:

CTCGAGGTCA CTAAGCAACT AACTTTGAGG AATGAGGTGA TGATGAATTA ACTCACTCCA      60

TTCCACAAAC CAAACAAAAA TTTGAGGAGT GAGAAGATGA TTGACTATCT CATTCCTCAA     120

ACCAAACACC TCAAATATAT CTGCTATCGG GATTGGCATT CCTGTATCCC TACGCCCGTG     180

TACCCCCTGT TTAGAGAACC TCCAAAGGTA TAAGATGGCG AAGATTATTG TTGTCTTGTC     240

TTTCATCATA TATCGAGTCT TTCCCTAGGA TATTATTATT GGCAATGAGC ATTACACGGT     300

TAATCGATTG AGAGAACATG CATCTCACCT TCAGCAAATA ATTACGATAA TCCATATTTT     360

ACGCTTCGTA ACTTCTCATG AGTTTCGATA TACAAATTTG TTTTCTGGAC ACCCTACCAT     420

TCATCCTCTT CGGAGAAGAG AGGAAGTGTC CTCAATTTAA ATATGTTGTC ATGCTGTAGT     480

TCTTCACAAA ATCTCAACAG GTACCAAGCA CATTGTTTCC ACAAATTATA TTTTAGTCAC     540

AATAAATCTA TATTATTATT AATATACTAA AACTATACTG ACGCTCAGAT GCTTTTACTA     600

GTTCTTGCTA GTATGTGATG TAGGTCTACG TGGACCAGAA AATAGTGAGA CACGGAAGAC     660

AAAAGAAGTA AAAGAGGCCC GGACTACGGC CCACATGAGA TTCGGCCCCG CCACCTCCGG     720

CAACCAGCGG CCGATCCAAC GGCAGTGCGC GCACACACAC AACCTCGTAT ATATCGCCGC     780

GCGGAAGCGG CGCGACCGAG GAAGCCTTGT CCTCGACACC CCCTACACAG GTGTCGCGCT     840

GCCCCCGACA CGAGTCCCGC ATGCGTCCCA CGCGGCCGCG CCAGATCCCG CCTCCGCGCG     900

TTGCCACGCC CTCTATAAAC ACCCAGCTCT CCCTCGCCCT CATCTACCTC ACTCGTAGTC     960

GTAGCTCAAG CATCAGCGGC AGCGGCAGCG GCAGGATCTC TGGGCAGCGT GCGCACGTGG    1020

GGTATCTAGC TCGCTCTGCT AGCCTACCAA TCGAATTCGG TAACCACCCG CCCCTCTCCT    1080

CTTTCTTTCT CCGTTTTTTT TTTCCGTCTC GGTCTCGATC TTTGGCCTTG GTAGTTTGGG    1140

TGGGCGAGAG GCGGCTTCGT GCGCGCCCAG ATCGGTGCGC GGGAGGGGCG GGATCTCGCG    1200

GCTGGGGCTC TCGCCGGCGT GGATCCGCC CGGATCTCGC GGGGAATGGG GCTCTCGGAT    1260

GTAGATCTGC GATCCGCCGT TGTTGGGGGA GATGATGGGG GGTTTAAAAT TTCCGCCATG    1320

CTAAACAAGA TCAGGAAGAG GGGAAAAGGG CACTATGGTT TATATTTTA TATATTTCTG    1380

CTGCTTCGTC AGGCTTAGAT GTGCTAGATC TTTCTTTCTT CTTTTTGTGG GTAGAATTTG    1440

AATCCCTCAG CATTGTTCAT CGGTAGTTTT TCTTTTCATG ATTTGTGACA AATGCACCTC    1500

GTGCGGAGCT TTTTTGTAGG TAGAATTCCA GCACACTGGC GGCCGTTACT AGTGGATCCG    1560

AGCTCGGTAC CAAGCTTATC GATACCGTCG AGATCCCCAA TTCGGCTTCC GGCCATGGTG    1620

AGCAAGGGCG AGGAGCTGTT CACCGGGGTG GTGCCCATCC TGGTCGAGCT GGACGGCGAC    1680

GTAAACGGCC ACAAGTTCAG CGTGTCCGGC GAGGGCGAGG GCGATGCCAC CTACGGCAAG    1740

CTGACCCTGA AGTTCATCTG CACCACCGGC AAGCTGCCCG TGCCCTGGCC CACCCTCGTG    1800

ACCACCCTGA CCTACGGCGT GCAGTGCTTC AGCCGCTACC CCGACCACAT GAAGCAGCAC    1860

GACTTCTTCA AGTCCGCCAT GCCCGAAGGC TACGTCCAGG AGCGCACCAT CTTCTTCAAG    1920
```

```
GACGACGGCA ACTACAAGAC CCGCGCCGAG GTGAAGTTCG AGGGCGACAC CCTGGTGAAC    1980

CGCATCGAGC TGAAGGGCAT CGACTTCAAG GAGGACGGCA ACATCCTGGG GCACAAGCTG    2040

GAGTACAACT ACAACAGCCA CAACGTCTAT ATCATGGCCG ACAAGCAGAA GAACGGCATC    2100

AAGGTGAACT TCAAGATCCG CCACAACACC GAGGACGGCA GCGTGCAGCT CGCCGACCAC    2160

TACCAGCAGA ACACCCCCAT CGGCGACGGC CCCGTGCTGC TGCCCGACAA CCACTACCTG    2220

AGCACCCAGT CCGCCTTGAG CAAAGACCCC AACGAGAAGC GCGATCACAT GGTCCTGCTG    2280

GAGTTCGTGA CCGCCGCCGG GATCACTCTC GGCATGGACG AGCTGTACAA GGGATCCATT    2340

GAACAAGATG GATTGCACGC AGGTTCTCCG GCCGCTTGGG TGGAGAGGCT ATTCGGCTAT    2400

GACTGGGCAC AACAGACAAT CGGCTGCTCT GATGCCGCCG TGTTCCGGCT GTCAGCGCAG    2460

GGGCGCCCGG TTCTTTTTGT CAAGACCGAC CTGTCCGGTG CCCTGAATGA ACTGCAGGAC    2520

GAGGCAGCGC GGCTATCGTG GCTGGCCACG ACGGGCGTTC CTTGCGCAGC TGTGCTCGAC    2580

GTTGTCACTG AAGCGGGAAG GGACTGGCTG CTATTGGGCG AAGTGCCGGG GCAGGATCTC    2640

CTGTCATCTC ACCTTGCTCC TGCCGAGAAA GTATCCATCA TGGCTGATGC AATGCGGCGG    2700

CTGCATACGC TTGATCCGGC TACCTGCCCA TTCGACCACC AAGCGAAACA TCGCATCGAG    2760

CGAGCACGTA CTCGGATGGA AGCCGGTCTT GTCGATCAGG ATGATCTGGA CGAAGAGCAT    2820

CAGGGGCTCG CGCCAGCCGA ACTGTTCGCC AGGCTCAAGG CGCGCATGCC CGACGGCGAG    2880

GATCTCGTCG TGACCCATGG CGATGCCTGC TTGCCGAATA TCATGGTGGA AAATGGCCGC    2940

TTTTCTGGAT TCATCGACTG TGGCCGGCTG GGTGTGGCGG ACCGCTATCA GGACATAGCG    3000

TTGGCTACCC GTGATATTGC TGAAGAGCTT GGCGGCGAAT GGGCTGACCG CTTCCTCGTG    3060

CTTTACGGTA TCGCCGCTCC CGATTCGCAG CGCATCGCCT TCTATCGCCT TCTTGACGAG    3120

TTCTTCTGAG AGCTCCCAAG CCGAATTGGG GATCGATGAG CTAAGCTAGC TATATCATCA    3180

ATTTATGTAT TACACATAAT ATCGCACTCA GTCTTTCATC TACGGCAATG TACCAGCTGA    3240

TATAATCAGT TATTGAAATA TTTCTGAATT TAAACTTGCA TCAATAAATT TATGTTTTTG    3300

CTTGGACTAT AATACCTGAC TTGTTATTTT ATCAATAAAT ATTTAAACTA TATTTCTTTC    3360

AAGATATCAT TCTTTACAAG TATACGTGTT TAAATTGAAT ACCATAAATT TTTATTTTTC    3420

AAATACATGT AAAATTATGA ATGGGAGTG GTGGCGACCG AGCTCAAGCA CACTTCAATT    3480

CCTATAACGG ACCAAATCGC AAAAATTATA ATAACATATT ATTTCATCCT GGATTAAAAG    3540

AAAGTCACCG GGGATTATTT TGTGACGCCG ATTACATACG GCGACAATAA AGACATTGGA    3600

AATCGTAGTA CATATTGGAA TACACTGATT ATATTAATGA TGAATACATA CTTTAATATC    3660

CTTACGTAGG ATCGATCCGA ATTTCGACCT CGAG                                3694
```

(2) INFORMATION FOR SEQ ID NO:6:

(i) SEQUENCE CHARACTERISTICS:
        (A) LENGTH: 1515 base pairs
        (B) TYPE: nucleic acid
        (C) STRANDEDNESS: double
        (D) TOPOLOGY: linear (xi) SEQUENCE DESCRIPTION: SEQ ID NO:6:

```
ATGGTGAGCA AGGGCGAGGA GCTGTTCACC GGGGTGGTGC CCATCCTGGT CGAGCTGGAC      60

GGCGACGTAA ACGGCCACAA GTTCAGCGTG TCCGGCGAGG GCGAGGGCGA TGCCACCTAC     120

GGCAAGCTGA CCCTGAAGTT CATCTGCACC ACCGGCAAGC TGCCCGTGCC CTGGCCCACC     180

CTCGTGACCA CCCTGACCTA CGGCGTGCAG TGCTTCAGCC GCTACCCCGA CCACATGAAG     240
```

-continued

```
CAGCACGACT TCTTCAAGTC CGCCATGCCC GAAGGCTACG TCCAGGAGCG CACCATCTTC      300

TTCAAGGACG ACGGCAACTA CAAGACCCGC GCCGAGGTGA AGTTCGAGGG CGACACCCTG      360

GTGAACCGCA TCGAGCTGAA GGGCATCGAC TTCAAGGAGG ACGGCAACAT CCTGGGGCAC      420

AAGCTGGAGT ACAACTACAA CAGCCACAAC GTCTATATCA TGGCCGACAA GCAGAAGAAC      480

GGCATCAAGG TGAACTTCAA GATCCGCCAC AACACCGAGG ACGGCAGCGT GCAGCTCGCC      540

GACCACTACC AGCAGAACAC CCCCATCGGC GACGGCCCCG TGCTGCTGCC CGACAACCAC      600

TACCTGAGCA CCCAGTCCGC CTTGAGCAAA GACCCCAACG AGAAGCGCGA TCACATGGTC      660

CTGCTGGAGT TCGTGACCGC CGCCGGGATC ACTCTCGGCA TGGACGAGCT GTACAAGGGA      720

TCCATTGAAC AAGATGGATT GCACGCAGGT TCTCCGGCCG CTTGGGTGGA GAGGCTATTC      780

GGCTATGACT GGGCACAACA GACAATCGGC TGCTCTGATG CCGCCGTGTT CCGGCTGTCA      840

GCGCAGGGGC GCCCGGTTCT TTTTGTCAAG ACCGACCTGT CCGGTGCCCT GAATGAACTG      900

CAGGACGAGG CAGCGCGGCT ATCGTGGCTG GCCACGACGG GCGTTCCTTG CGCAGCTGTG      960

CTCGACGTTG TCACTGAAGC GGGAAGGGAC TGGCTGCTAT TGGGCGAAGT GCCGGGGCAG      1020

GATCTCCTGT CATCTCACCT TGCTCCTGCC GAGAAAGTAT CCATCATGGC TGATGCAATG      1080

CGGCGGCTGC ATACGCTTGA TCCGGCTACC TGCCCATTCG ACCACCAAGC GAAACATCGC      1140

ATCGAGCGAG CACGTACTCG GATGGAAGCC GGTCTTGTCG ATCAGGATGA TCTGGACGAA      1200

GAGCATCAGG GGCTCGCGCC AGCCGAACTG TTCGCCAGGC TCAAGGCGCG CATGCCCGAC      1260

GGCGAGGATC TCGTCGTGAC CCATGGCGAT GCCTGCTTGC CGAATATCAT GGTGGAAAAT      1320

GGCCGCTTTT CTGGATTCAT CGACTGTGGC CGGCTGGGTG TGGCGGACCG CTATCAGGAC      1380

ATAGCGTTGG CTACCCGTGA TATTGCTGAA GAGCTTGGCG GCGAATGGGC TGACCGCTTC      1440

CTCGTGCTTT ACGGTATCGC CGCTCCCGAT TCGCAGCGCA TCGCCTTCTA TCGCCTTCTT      1500

GACGAGTTCT TCTGA                                                      1515
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:7:

```
AACCATGGGC AAGGGCG                                                    17
```

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:8:

```
CTGGATCCCT TGTAGAGTTC ATCCATGC                                        28
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

CCGGCCATGG TGAGCAAGGG CG                    22

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:10:

CTGGATCCCT TGTACAGCTC GTCCATGC              28

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

CGGGATCCAT TGAACAAGAT TGCAC                 25

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:12:

GGGAGCTCTC AGAAGAACTC GTCAAGAAG             29

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

CGGGTCGATG CTGGTGCTGT C                     21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

GGTCGATGCG GTGCTGTGCT G                     21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

```
GGTAGGCTAG CAGAGCGAGC T                                                         21

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:16:

TCGAGGTCGA CGGTATC                                                              17

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:17:

TTGCTGAAGG TGAGATGC                                                             18

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:18:

GGAATTCGGT AACCACCCCG CCCCTCT                                                   27

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:19:

GGAATTCTAC CTACAAAAAA GCTCCG                                                    26
```

METHODS AND COMPOSITIONS FOR TRANSGENE IDENTIFICATION

BACKGROUND OF THE INVENTION

1. Field of the Invention

The present invention relates generally to the field of agricultural biotechnology. More particularly, it concerns methods and compositions for the efficient identification of transgenic plant seeds.

2. Description of Related Art

Many attempts have been made to genetically engineer desired traits into plant genomes by introduction of exogenous genes using genetic engineering techniques. The uptake of new DNA by recipient plant cells has been accomplished by various means, including Agrobacterium infection (Nester et al., 1984), polyethylene glycol (PEG)-mediated DNA uptake (Lorz et al., 1985), electroporation of protoplasts (Fromm et al., 1986) and microprojectile bombardment (Klein et al., 1987).

An important aspect of the success achieved in transforming plants has been the ability to select or screen for transformed cells and/or plants. Most of the first successes in plant transformation relied on utilization of selectable markers for identification of transformed cells. Genes which have been used for selection of transformed plant cells include, for example, a neomycin phosphotransferase gene (Potrykus et al., 1985) which provides resistance to kanamycin, paromomycin and G418; a bar gene which codes for bialaphos or phosphinothricine resistance (U.S. Pat. No. 5,550,318); a mutant aroA gene which encodes an altered EPSP synthase protein conferring glyphosate resistance (Hinchee et al., 1988); a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS inhibiting chemicals (European Patent Application 154,204, 1985); a methotrexate resistant DHFR gene (Thillet et al., 1988); a dalapon dehalogenase gene that confers resistance to the herbicide dalapon; and a mutated anthranilate synthase gene that confers resistance to 5-methyl tryptophan.

More recently, interest has increased in utilization of screenable markers. One particularly useful screenable marker which has been discovered is the green fluorescent protein (GFP) (Sheen et al., 1995). GFP was first cloned and sequenced from the cnidarian *Aequorea victoria* (Prasher et al., 1992). Since then, it has been expressed in a variety of organisms, ranging from bacteria (Leff and Leff, 1996), fungi (Spellig et al., 1996), invertebrates (Plautz et al., 1996), vertebrates (Zolotukhin et al., 1996) and plants (Haseloff et al., 1997; Reichel et al., 1996; Sheen et al., 1995; Tian et al., 1997). An important advantage of GFP is that it can be assayed non-destructively. Firefly luciferase represents another useful fluorescent marker which can be assayed non-destructively, although detection requires addition of an exogenous substrate (luciferin) for detection (Ow et al., 1986; Millar et al., 1995). In contrast, the assay of the screenable marker GUS is cytotoxic, and therefore, recovery of live transformed cells is difficult (Jefferson et al., 1987).

One means that has been employed for the utilization of screenable markers, such as GFP, has been the fusion of the screenable marker with a selectable marker. Fusion proteins have been made, for example, between GFP and the selectable marker neomycin phosphotransferase (NPTII) (Genbank Accession No. AF004665), between GFP and hygromycin phosphotransferase (Lybarger et al. 1996), between the firefly luciferase gene (luc) and the neomycin phosphotransferase (NPTII) (Barnes, 1990), and between the ALS gene and GFP or GUS (WO 97/41228). The screening of transgenic maize cells based on GFP expression was described in WO 97/41228.

The identification of transgenic seeds using a GFP screenable marker also was described in WO 97/41228. In this case, however, the GFP gene was constitutively expressed using the ubiquitin promoter. It was found that seeds expressing GFP did not germinate when planted in soil, and could only be germinated by excision of embryos and plating on growth medium.

The failure to identify a method of non-destructively identifying transgenic seeds which can be directly germinated has represented a significant hindrance to breeders during the development of novel transgenic plant lines. Without labor-intensive embryo-rescue, current technology requires the growing and assaying of potentially transgenic seeds. The identification of a direct means for selection of transgenic cells, regeneration of plants from the transgenic cells and the screening of transgenic seeds which could, in turn, be directly advanced in breeding protocols would greatly improve scientists abilities to develop novel transgenic plant lines for the benefit of consumers.

SUMMARY OF THE INVENTION

The current invention seeks to overcome deficiencies in the prior art by providing methods and composition for the efficient identification of transgenic seeds. Therefore, in one aspect, the current invention provides a construct comprising a screenable marker gene operably linked to an aleurone-specific promoter. This screenable marker gene can be provided as a gene fusion between the screenable marker gene and a selectable marker gene, wherein the gene fusion is operably linked to an aleurone-specific promoter. In particular embodiments of the invention, the screenable marker gene is selected from the group consisting of a GFP gene, a luciferase gene, and an R gene. In other embodiments of the invention, the selectable marker gene comprises a gene selected from the group consisting of NPTII, bar, EPSPS, anthranalite synthase and dalapon dehalogenase. In still other embodiments of the invention, the aleurone-specific promoter is selected from the group consisting of an oleosin promoter, globulin 1 promoter, a barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter. The oleosin promoter may be an L3 oleosin promoter. The marker gene constructs of the invention may additionally comprise first, second, third, or any additional number of exogenous genes which can physically be placed on the construct. The exogenous gene may be operably linked to a second promoter.

In another aspect, the invention provides a transgenic plant comprising a screenable marker gene operably linked to an aleurone-specific promoter. This screenable marker gene can be provided as a gene fusion between a selectable marker gene and the screenable marker gene, wherein the gene fusion is operably linked to an aleurone-specific promoter. In one embodiment of the invention, the screenable marker gene is selected from the group consisting of a GFP gene, a luciferase gene, and an R gene. In other embodiments of the invention, the screenable marker is a GFP gene. The selectable marker gene may comprise any suitable gene, for example, bar, EPSPS, NPTII, anthranalite synthase or dalapon dehalogenase. The promoter may be selected from the group consisting of an L3 oleosin promoter, a globulin 1 promoter, and a barley LTP2 promoter. The plant may be a monocotyledonous plant, and may be further defined as a plant selected from the group consisting of maize, rice, wheat, barley, oat, rye, millet, sorghum, sugarcane and turfgrass. In particular embodiments of the invention, the monocotyledonous plant is maize. The plant may also be a dicotyledonous plant, and may still further be selected from the group consisting of cotton, soybean, tomato, potato, citrus, and tobacco. In particular embodiments of the invention, the dicotyledonous plant is soybean.

In still yet another aspect, the invention provides a progeny plant of any generation of a transgenic plant comprising a screenable marker gene operably linked to an aleurone-specific promoter, wherein the progeny comprises said screenable marker gene. This screenable marker gene can be provided as a gene fusion between a selectable marker gene and the screenable marker gene, wherein the gene fusion is operably linked to an aleurone-specific promoter.

In still yet another aspect, the invention provides a method of identifying transgenic seeds comprising the steps of: (a) obtaining a transgenic plant, the cells of which comprise a screenable marker gene operably linked to an aleurone-specific promoter; (b) cultivating said plant until seed set; (c) collecting seeds produced on said plant; and (d) screening said seeds based on a phenotype conferred upon seeds by said screenable marker gene. In one embodiment of the invention, the screenable marker gene is provided as a gene fusion between a selectable marker gene and the screenable marker gene, wherein the gene fusion is operably linked to an aleurone-specific promoter. In particular embodiments of the invention, the screenable marker gene is selected from the group consisting of a GFP gene, a luciferase gene, and an R gene. The transgenic plant may be a monocotyledonous plant, and further, may be selected from the group consisting of maize, rice, wheat, barley, oat, rye, millet, sorghum, sugarcane and turfgrass. In particular embodiments of the invention, the monocotyledonous plant is maize. The transgenic plant may also be a dicotyledonous plant, and further defined as selected from the group consisting of cotton, soybean, tomato, potato, citrus, and tobacco. In particular embodiments of the invention, the dicotyledonous plant is soybean.

In the method of identifying seeds provided by the invention, the transgenic plant may further comprise an exogenous gene encoding a selected trait, wherein the exogenous gene is genetically linked to said screenable marker gene. The exogenous gene may still further comprise a promoter and 3' region operably linked to said exogenous gene. In particular embodiments of the invention, the exogenous gene encodes a trait selected from the group consisting of an insect resistance gene, a viral disease resistance gene, a bacterial disease resistance gene, a fungal disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene. The screenable marker gene may also comprise a 3' region operatively linked to the gene, and also an element enhancing the expression of said gene. In particular embodiments of the invention, the screening of collected seeds is automated.

In still yet another aspect, the invention provides a method of plant breeding comprising the steps of: (a) obtaining first and second plants, wherein cells of one or both of said first or second plants comprises a screenable marker gene operably linked to an aleurone-specific promoter; (b) crossing said first and second plants; and (c) collecting the seeds resulting from said crossing. The method may further comprise the step of: (d) selecting transgenic seeds from said collected seeds based on a phenotype conferred upon said transgenic seeds by said screenable marker gene. The screenable marker gene can be provided as a gene fusion between a selectable marker gene and the screenable marker gene, wherein the gene fusion is operably linked to an aleurone-specific promoter. In particular embodiments of the invention, the screenable marker gene may be selected from the group consisting of a GFP gene, a luciferase gene, and an R gene. In other embodiments of the invention, the selectable marker gene is selected from the group consisting of bar, EPSPS, NPTII, anthranalite synthase and dalapon dehalogenase. In still further embodiments of the invention, the aleurone-specific promoter is selected from the group consisting of an oleosin promoter, globulin 1 promoter, barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter. Where the promoter is an oleosin promoter, an L3 oleosin promoter may be used.

In the method of plant breeding, the first and second transgenic plants may be monocotyledonous plants, and may be selected from the group consisting of maize, rice, wheat, barley, oat, rye, millet, sorghum, sugarcane and turfgrass. In particular embodiments of the invention, the monocotyledonous plants are maize plants. The plants may also be dicotyledonous plants, and can be selected from the group consisting of cotton, soybean, tomato, potato, citrus, and tobacco. In one embodiment of the invention, the dicotyledonous plants are soybean plants. In other embodiments of the invention, the step of selecting can be automated.

In still yet another aspect, the invention provides a method of plant breeding comprising the steps of: (a) obtaining a transgenic plant, the cells of which comprise a screenable marker gene operably linked to an aleurone-specific promoter; (b) allowing said plant to self fertilize; and (c) collecting the seeds produced on said plant. The method may further comprise the step of: (d) selecting transgenic seeds from said collected seeds based on the phenotype conferred upon said transgenic seeds by said screenable marker gene. The screenable marker gene can be provided as a gene fusion between a selectable marker gene and the screenable marker gene, wherein the gene fusion is operably linked to an aleurone-specific promoter. In particular embodiments of the invention, the screenable marker gene is selected from the group consisting of a GFP gene, a luciferase gene, and an R gene. In other embodiments of the invention, the selectable marker gene is selected from the group consisting of bar, EPSPS, NPTII, anthranalite synthase and dalapon dehalogenase. In still further embodiments of the invention, the aleurone-specific promoter is selected from the group consisting of an oleosin promoter, globulin 1 promoter, a barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter. In certain embodiments of the invention, the oleosin promoter may be an L3 oleosin promoter. comprises a globulin 1 promoter. The transgenic plant may be a monocotyledonous plant, and may still further be selected from the group consisting of maize, rice, wheat, barley, oat, rye, millet, sorghum, sugarcane and turfgrass. In particular embodiments of the invention, the monocotyledonous plant is a maize plant. The transgenic plant may also be a dicotyledonous plant, and may further be selected from the group consisting of cotton, soybean, tomato, potato, citrus, and tobacco. In particular embodiments of the invention, the dicotyledonous plant is a soybean plant. In other embodiments of the invention, the step of selecting may be automated.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
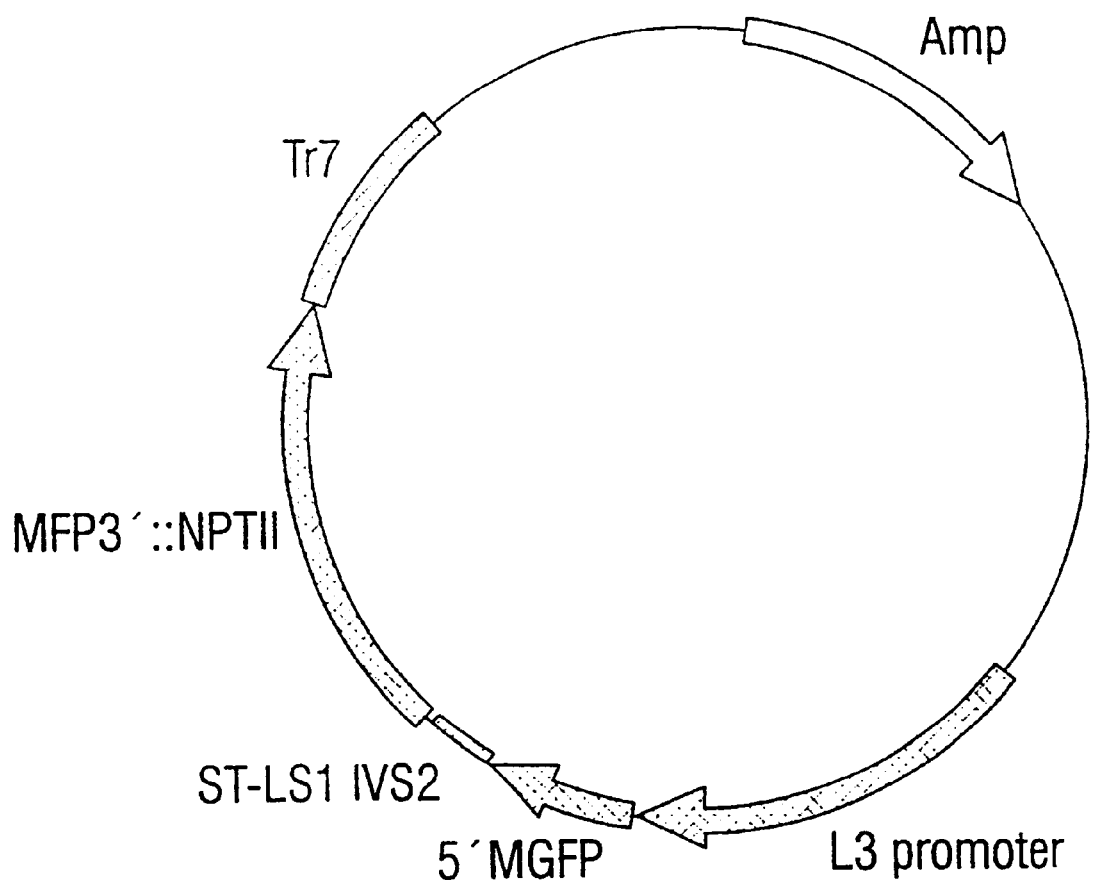
FIG. 1: Map of plasmid DV130. The 6237 bp plasmid contains an expression cassette comprising a 1039 bp promoter from the maize L3 oleosin gene; the coding sequence of a MGFP::NPTII translational fusion; and the Tr7 terminator.
Figure 2:
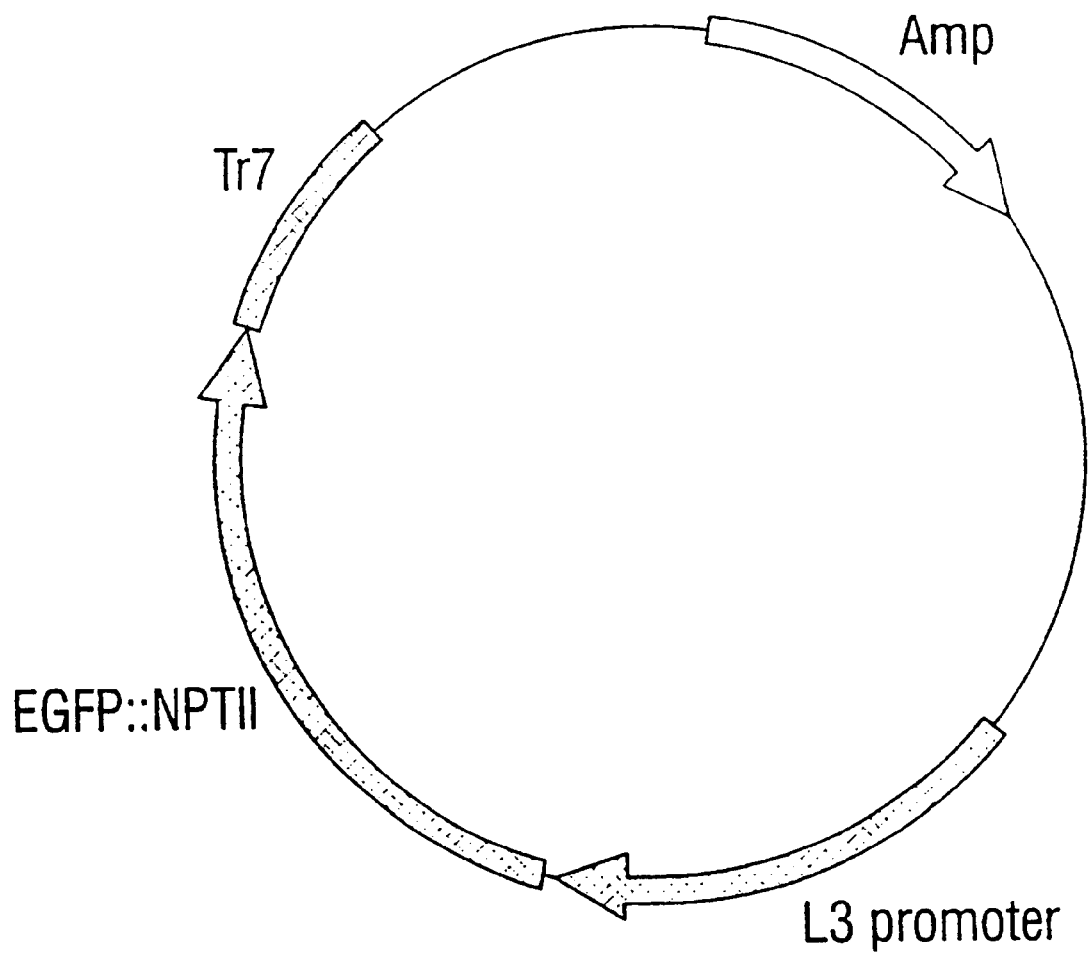
FIG. 2: Map of plasmid DV131. The 6054 bp plasmid contains an expression cassette comprised of a 1039 bp promoter from the maize L3 oleosin gene; the coding sequence of a EGFP::NPTII translational fusion; and the Tr7 terminator.
Figure 3:
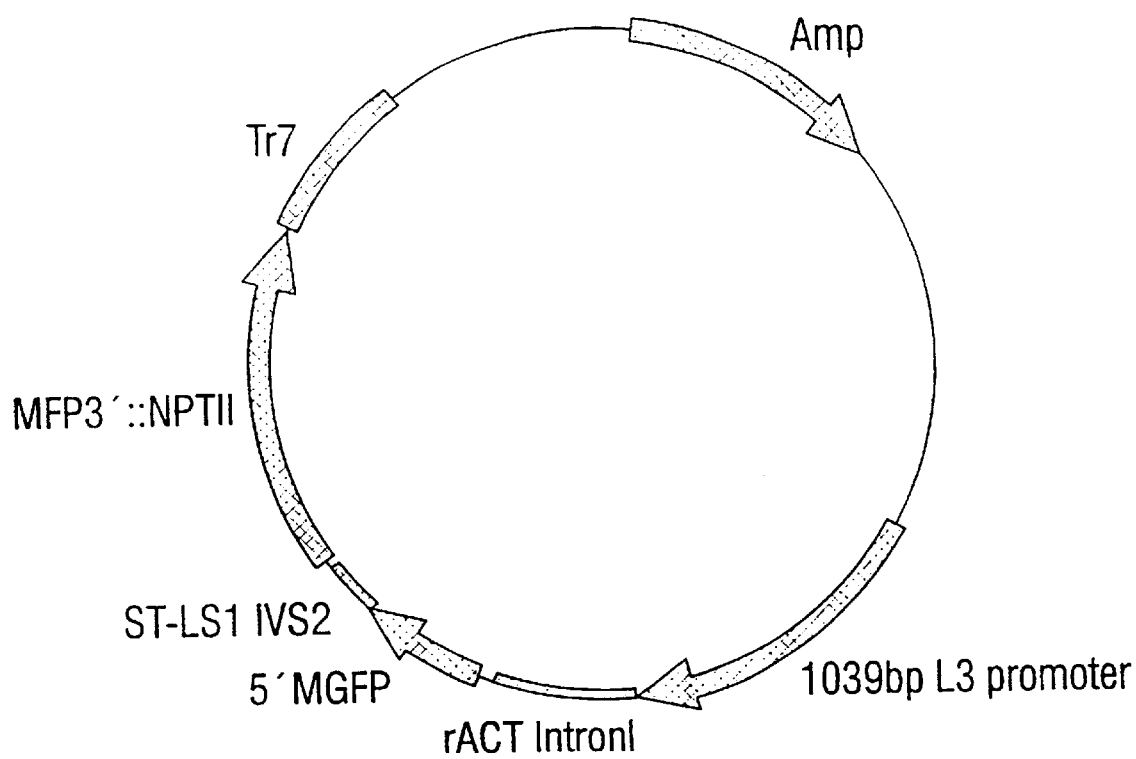
FIG. 3: Map of plasmid DV132. The 6778 bp plasmid contains an expression cassette comprised of a 1039 bp promoter from the maize L3 oleosin gene; the rice actin 1 intron 1; the coding sequence of a MGFP::NPTII translational fusion; and the Tr7 terminator.
Figure 4:
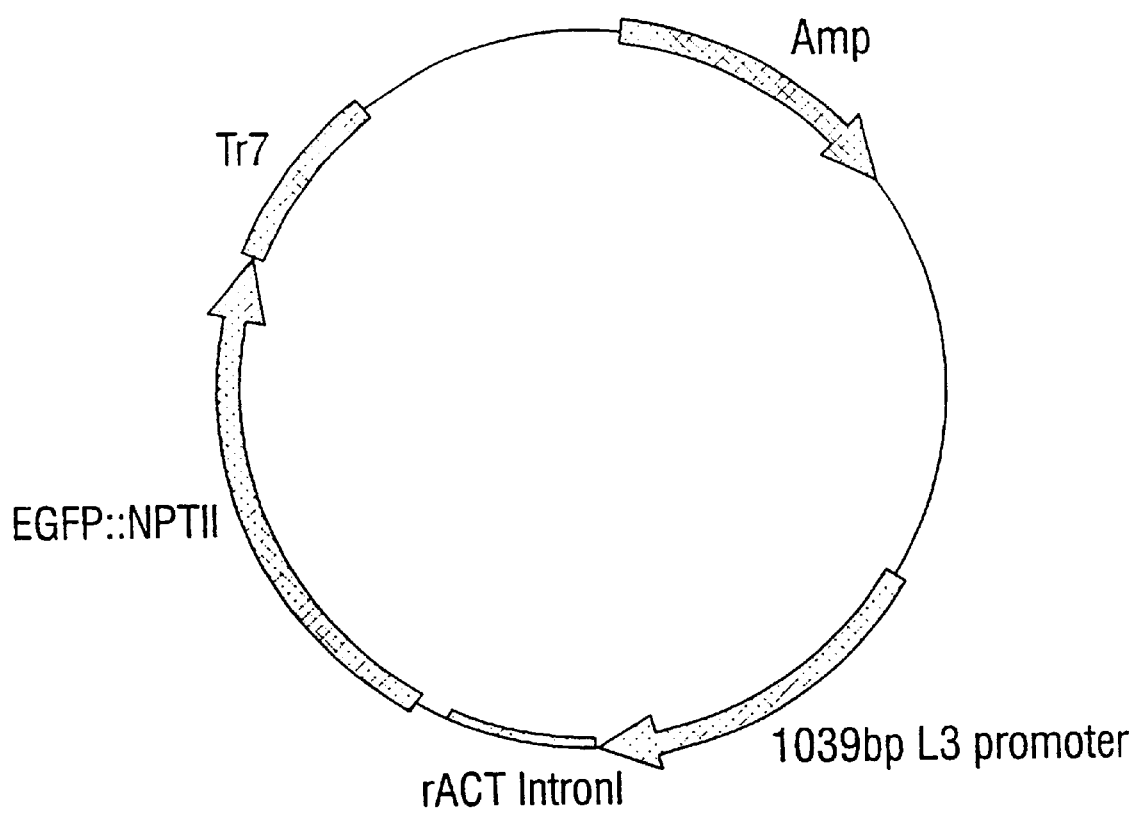
FIG. 4: Map of plasmid DV133. The 6595 bp plasmid contains an expression cassette comprised of a 1039 bp promoter from the maize L3 oleosin gene; the rice actin 1 intron 1; the coding sequence of a EGFP::NPTII translational fusion; and the Tr7 terminator.

The current invention overcomes deficiencies in the prior art by providing constructs which allow the visual identification of seeds which have inherited a transgene prepared in accordance to the instant invention. In particular, the present invention provides transformation constructs which include a screenable marker which is preferentially expressed in the seed coat or aleurone of seeds, but not in the whole seed. Such promoters also direct expression of the construct in embryogenic tissues, thereby allowing the identification and regeneration of transgenic cells into whole plants. The expression of the screenable marker gene specifically in embryogenic tissues and the aleurone allows for direct detection of transgenic cells and seeds, while avoiding the deleterious effects associated with the expression of green fluorescent protein (GFP) and other screenable markers in whole seeds or plants.

The constructs of the invention also are provided as gene fusions between selectable and screenable marker genes. Gene fusions are expressed as a single unit, yet produce a gene product conferring both the selectable and screenable marker gene phenotypes of the non-fused starting genes. Because the genes are expressed together, expression of the selectable marker phenotype is directly correlated with the screenable marker phenotype. In cases where selectable and screenable marker genes are transformed on different DNA segments, or even on the same DNA segment but under the control of a separate promoter, the expression of one marker may often not be correlated with the expression of the other.

By expression of the selectable-screenable marker gene fusion with a promoter which directs expression specifically in the aleurone, but also in embryogenic cells, transgenic cells can be identified using a selective agent and transgenic seeds identified by expression of the screenable marker. Selection of transgenic cells is often preferable to screening, because typically only a small number of target cells will be transformed. In cases where intact cells are transformed, screening for transgenic cells can lead to regeneration of chimeric plants, wherein regenerated plants contain both transgenic and non-transgenic cells. The tissue-specific expression of a selectable-screenable marker gene fusion is important because it serves to eliminate problems associated with constitutive expression of selectable marker genes, and in particular, with GFP.

Preferably, the DNA construct which comprises the screenable marker gene also contains at least a first exogenous gene encoding a selected trait. Alternatively, a construct comprising an exogenous gene may be co-transformed with a second construct comprising a screenable marker in accordance with the current invention. In these instances, the screenable marker or selectable-screenable marker gene phenotype typically will be genetically linked to the exogenous gene and, therefore, can be used to predict the presence of the exogenous gene. As such, a screenable marker gene expressed, for example, in a seed, can provide predictive value for the presence of exogenous genes which otherwise could not be non-destructively assayed at the whole-seed level. The exogenous genes used in combination with the marker genes of the invention may confer potentially any trait one desires to have expressed in a transgenic plant. Specific examples of such traits and the genes which confer these traits are disclosed herein below.

I. Marker Gene Compositions

The present invention provides methods and composition for the expression and identification of screenable marker genes in seeds, thereby allowing rapid visual confirmation of transgenic seeds. While the expression constructs of the invention could include only a screenable marker gene linked to an aleurone-specific promoter, more preferred will be constructs which also include a selectable marker gene. The selectable marker allows for efficient isolation of transformed cells and subsequent regeneration of transformed plants, which would typically not be achieved using screening techniques alone. Even more preferred for use will be a screenable marker gene which has been fused to a selectable marker gene to form a selectable-screenable marker gene fusion.

The protein produced by a selectable-screenable marker gene fusion exhibits the activity of both the selectable and the screenable marker genes, yet comprises a single transcribed gene product, thereby decreasing the overall size of the construct and minimizing size constraints for the inclusion in the construct of one or more expressible genes encoding a selected trait. Additionally, by decreasing the overall size of the construct used for transformation, the likelihood of obtaining transgenes with rearranged insertion events is minimized. Still further, utilization of a fusion protein should maximize the correlation between expression of the marker genes with the presence of any exogenous genes encoded on the construct.

A number of different screenable and selectable marker genes are known in the art and could be employed for the preparation of a selectable-screenable marker gene fusion. For use with the instant invention, the screenable marker gene should be detectable when expressed in seeds using non-lethal assays and should be preferentially expressed in the aleurone or embryo. The selectable marker gene should allow for efficient recovery of transformed cells and subsequent recovery of transformed plants. The selectable and screenable marker genes also should be capable of forming a fusion protein which exhibits the activities of both marker genes. Further, it is preferable that marker genes having shorter overall gene sequences be used in order to limit the length of the resulting construct.

One particularly useful screenable marker for the production of selectable-screenable marker gene fusions, in accordance with the current invention, is the green fluorescent protein (GFP) (Sheen et al., 1995). Detection of GFP fluorescence does not require a cofactor or a substrate, and is non-lethal (Cody et al., 1993). Detection of GFP in living cells only requires excitation by light at 395 or 470 nm. Additionally, many variants of GFP have been produced which exhibit various desirable characteristics such as altered wavelengths of fluorescence excitation and emission.

Another screenable marker gene contemplated for use in the present invention is firefly luciferase, encoded by the lux gene (Ow et al., 1986). The presence of the lux gene is detected by immersion of the transformed cells in the substrate luciferin, followed by detection using, for example, X-ray film, scintillation counting, fluorescent spectrophotometry, low-light video cameras, photon counting cameras or multiwell luminometry. Genes from the maize R gene complex also could be used as screenable markers with the current invention. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively, any plant species can be utilized if the C1 and R alleles are introduced together.

A number of selectable marker genes also may be used in connection with the present invention. One selectable marker gene deemed especially useful for the creation of selectable-screenable marker gene fusions in accordance with the instant invention is the neomycin phosphotransferase II (NPTII) gene (Potrykus et al., 1985) which codes for kanamycin resistance and can be selected for using kanamycin, G418, paromomycin, etc. Examples of other selectable marker genes which could potentially be used with the instant invention include a bar gene from *Streptomyces hygroscopicus* or a pat gene from *Streptomyces viridochromogenes*, which genes confer bialaphos resistance; a mutant EPSP synthase gene (Hinchee et al., 1988) conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS inhibiting chemicals (European Patent Application 154,204); a methotrexate resistant DHFR gene (Thillet et al., 1988); a dalapon dehalogenase gene that confers resistance to the herbicide dalapon; a hygromycin phosphotransferase gene conferring resistance to hygromycin or a mutated anthranilate synthase gene that confers resistance to 5-methyl tryptophan. Where a mutant EPSP synthase gene is employed, additional benefit may be realized through the incorporation of a suitable chloroplast transit peptide, e.g., CTP (U.S. Pat. No. 5,188, 642)or OTP (U.S. Pat. No. 5,633,448) and use of the modified maize EPSPS gene described in PCT Application WO 97/04103.

II. Optimization of GFP

Various modifications may be made in the gene encoding green fluorescent protein to modify its characteristics as a fluorescent marker. These modifications are specifically contemplated by the inventors for use with the current invention. In particular, it is contemplated that the utility of GFP for the identification of transformed seeds may be supplemented by the development of chromophore-mutated versions of GFP, in which amino acid substitutions have produced forms of the protein with shifted excitation peaks, increased stability, single excitation and emission peaks, brighter fluorescence, and more rapid chromophore formation (Heim et al., 1995). These modifications can be used to increase the sensitivity of GFP detection, allow simultaneous analysis of two GFP constructs per cell, seed or organism, and offer better matching to standard filter sets.

Wild-type GFP has two excitation points at about 395 and 470 nm, and it emits the most amount of green light at 508–509 nm (Chalfie et al., 1994a). A blue-shifted variant can be produced by substituting histidine or tryptophan for tyrosine at position 66 in the chromophore (Heim and Tsien, 1996). These mutants, called blue fluorescent proteins (BFPs) (Heim and Tsien, 1996) were created to enhance GFP as a molecular tool by providing a second visibly distinct color for in vivo visualization of subcellular activities (Heim et al., 1994). Similarly a GFP protein has been produced with a red-shifted excitation peak (Delagrave et al., 1995)

Other mutations, made by changing a serine at amino acid 65 to cysteine and threonine, have increased the magnitude of green fluorescence, significantly improving the detection levels of GFP (Reichel et al., 1996). In addition, other modifications, known as F64L and S65T, have improved the folding in a marker known as EGFP, a modified version of the native GFP protein (Cormack et al., 1996; Yang et al., 1996a).

Though the wild-type gene has been expressed in both monocot and dicot cells (Reichel et al., 1996), expression had generally been low or unstable in plants (Hu and Cheng, 1995). Therefore, modified versions of the gene, such as mgfp4, were produced when an 84-bp sequence necessary for proper protein folding and expression was found to be mis-spliced in Arabidopsis (Haseloff and Amos, 1995). The sequence similarity to known plant introns caused it to be spliced-out during transcription, so Haseloff and colleagues reduced its AT content and reduced the chance of the sequence being excised, thereby restoring proper expression in the plant (Haseloff et al., 1997). To help improve visible fluorescence from GFP, a modified GFP construct (mgfp5-er) has also been produced that targets the protein to the endoplasmic reticulum, resulting in high, in vivo, expression in plants (Haseloff et al., 1997).

III. Codon Modifications for Plant Gene Expression

It may, in particular embodiments of the invention, be desirable to utilize genes in which the native DNA sequence has been modified to enhance expression in maize or other plants. Specifically, it may be desired to adjust the DNA sequence of the transgene to more closely resemble that of genes which are efficiently expressed in the host plant. For example, it has been shown that by modifying the codon usage of the GFP gene to decrease the overall AT content of the gene, expression of the GFP protein can be dramatically increased in corn protoplasts and tobacco plants (Chiu et al., 1996).

Such codon modifications may be carried out by substitution of bases in a native gene sequence without changing the sequence of the encoded polypeptide. In this manner, an identical polypeptide may be produced, but at levels much higher than would otherwise be produced using constructs comprising the native gene sequence. Such alterations may be particularly desirable in the case of genes which were originally isolated from organisms distantly related to the plant host, such as with the case of bacterial genes.

In designing synthetic genes for enhanced expression in plants, the DNA sequence of the native structural gene is modified in order to contain codons preferred by highly expressed plant genes. Preferably, the A+T content of the synthetic gene is substantially equal to that of genes for highly expressed proteins in the host plant. In genes encoding highly expressed plant proteins, the A+T content is approximately 55%. It is preferred that the synthetic gene have an A+T content near this value, and not sufficiently high as to cause destabilization of RNA and, therefore, lower the protein expression levels. More preferably, the A+T content is no more than about 60% and most preferably is about 55%.

It is known in the art that seldom used codons are generally detrimental to gene expression and must be avoided or used judiciously. Thus, in designing a synthetic gene encoding the desired transgene polypeptide, individual amino acid codons found in the original gene are altered to reflect the codons preferred by the host plant for a particular amino acid. However, attention is given to maintaining the overall distribution of codons for each amino acid within the coding region of the gene. Hence, the synthetic gene is designed such that its distribution frequency of codon usage deviates, preferably, no more than 25% from that of highly expressed plant genes and, more preferably, no more than about 10%. Preferred codons used in maize, for example, are given in Table 1. The preferred codons for design of synthetic genes for expression in other plants will be well known to those of skill in the art and may be found in, for example, Wada et al., 1990.

In designing a heterologous gene for expression in plants, sequences which interfere with the efficacy of gene expression, such as plant polyadenylation signals, polymerase II termination sequences, hairpins, plant consensus splice sites and the like, are eliminated. Also, for ultimate expression in plants, the synthetic gene nucleotide sequence is preferably modified to form a plant initiation sequence at the 5' end of the coding region. In addition, particular attention is preferably given to assure that unique restriction sites are placed in strategic positions to allow efficient assembly of oligonucleotide segments during construction of the synthetic gene and to facilitate subsequent nucleotide modification. Consideration will also be given to the percentage G+C content of the degenerate third base (monocot plants appear to favor G+C in this position, whereas dicots do not). It is recognized that the XCG nucleotide is the least preferred codon in dicots whereas the XTA codon is avoided in both monocots and dicots. Synthetic genes will also preferably have CG and TA doublet avoidance indices approximating those of the chosen host plant.

As is known to those skilled in the art of synthesizing genes, the DNA sequence to be synthesized is divided into segment lengths which can be synthesized conveniently and without undue complication. Each segment has unique restriction sequences at the cohesive ends. Single-stranded oligonucleotides are annealed and ligated to form the DNA segments. The length of the protruding cohesive ends in complementary oligonucleotide segments is four to five residues. In the strategy evolved for gene synthesis, the sites designed for the joining of oligonucleotide pieces and DNA segments are different from the restriction sites created in the gene. The nucleotide sequence of each fragment is determined at this stage by the dideoxy method using recombinant phage DNA as templates and selected synthetic oligonucleotides as primers. Each segment is individually excised at the flanking restriction sites from its cloning vector and spliced into the vector containing segment. Most often, segments are added as a paired segment, instead of as a single segment, to increase efficiency. In this way, the entire gene is constructed in the original plasmid. Exemplary procedures for the design and production of synthetic genes which may be used in the context of the current invention are disclosed in, for example, U.S. Pat. Nos. 5,567,600; 5,567,862; 5,500,365; and 5,508,468, each of which is specifically incorporated herein by reference in its entirety.

TABLE 1

Preferred Maize DNA Codons

| Amino Acids | | Codons (most preferred → less preferred) |
|---|---|---|
| Alanine | Ala A | GCC GCT GCG GCA |
| Cysteine | Cys C | TGC TGT |
| Aspartic acid | Asp D | GAC GAT |
| Glutamic acid | Glu E | GAG GAA |
| Phenylalanine | Phe F | TTC TTT |
| Glycine | Gly G | GGC GGT GGG GGA |
| Histidine | His H | CAC CAT |
| Isoleucine | Ile I | ATC ATT ATA |
| Lysine | Lys K | AAG AAA |
| Leucine | Leu L | CTG CTC CTT TTG CTA TTA |
| Methionine | Met M | ATG |
| Asparagine | Asn N | AAC AAT |
| Proline | Pro P | CCG CCA CCC CCT |
| Glutamine | Gln Q | CAG CAA |
| Arginine | Arg R | CGC AGG CGG CGT AGA CGA |

TABLE 1-continued

Preferred Maize DNA Codons

| Amino Acids | | Codons (most preferred → less preferred) |
|---|---|---|
| Serine | Ser S | AGC TCC TCG TCT TCA AGT |
| Threonine | Thr T | ACC ACG ACT ACA |
| Valine | Val V | GTG GTC GTT GTA |
| Tryptophan | Trp W | TGG |
| Tyrosine | Tyr Y | TAC TAT |

IV. Automated Screening of Transgenic Seeds

Automated screening techniques may be implemented with the current invention for the identification of transgenic seeds. By implementation of automated techniques, large numbers of seeds can be efficiently screened and the transgenic seeds among a total population of seeds collected. Automated techniques may be faster, less expensive and more accurate than reliance upon human technicians.

Seed sorting machines which could be used with the current invention have been described. For example, described in U.S. Pat. No. 4,946,046, the disclosure of which is specifically incorporated herein by reference in its entirety, is an apparatus for sorting seeds according to color. In this machine, seeds are sorted according to color by placing the seeds in uniform rows of indentations in a rotating drum and passing the seeds beneath a digital imaging camera and a light source. Images are read by the camera and are fed to a computer, which also receives information from a drum speed sensor. The computer generates a signal which causes a blast of air to blow through an opening in the bottom of an indentation containing a colored seed to collect such seed. Collected seeds are fed into a collection hopper, and the non-colored seeds into a separate hopper.

By varying the wavelength of the light source used for detection of colored seeds, as well as barrier filters placed between the colored seed and the detection camera, potentially any screenable marker could be detected with this technique. For example, to detect seeds expressing GFP, the excitation wavelength is in the blue light—UV spectrum, typically at about 395 nm. Suitable light sources for UV emission are well known to those of skill in the art, and include xenon or mercury lamps. Suitable filter sets also are well known to those of skill in the art, and include, for example, a BP450-490 exciter filter, an FT510 chromatic beam splitter, and a BP515-565 barrier filter (Carl Zeiss, Inc., Thornwood, N.Y.). Such filter sets and emission wavelengths are discussed in more detail in Heim and Tsien, 1996, the disclosure of which is specifically incorporated herein by reference in its entirety.

The detection system described above also may be adapted to sort seeds based on the strength of coloration of the seeds. By decreasing the intensity of the light source, or changing the selection criteria, only those seeds which strongly express the screenable marker gene will be selected. It is specifically contemplated that this will allow the selection of highly expressing transformation events. Further, by use for transformation of constructs comprising one or more exogenous genes in addition to selectable-screenable marker genes, the selective power can be extended to the exogenous genes. Therefore, large numbers of transgenic seeds, representing a variety of different transformation events, can be efficiently screened and only those transformation events which are highly expressed selected.

V. Transformation Constructs

In addition to marker genes, the DNA constructs of the invention may further include structures such as exogenous genes, enhancers, polylinkers, or regulatory genes as desired. The DNA constructs may be in the form of vectors and plasmids, or linear DNA fragments. Whole vector DNA may be used for transformation, or alternatively, an isolated expression cassette containing the constructs of the invention can be used. The constructs may additionally be co-transformed into recipient cells with one or more other vectors. Using this method, it is assumed that the additional vector inserts into the host genome at a location which is genetically linked to the marker gene, thereby allowing the use of the marker gene for identification of transformants which include the co-transformed vector DNA. The constructs of the invention used for transformation may be contained on vectors such as plasmids, cosmids, YACs (yeast artificial chromosomes), BACs (bacterial artificial chromosomes) or DNA segments isolated therefrom.

(i) Regulatory Elements

The constructs of the invention will include a selectable-screenable marker gene fusion, wherein the screenable marker permits the identification of seeds which have inherited the transgene construct. As such, the marker gene fusion should be operably linked to a promoter capable of preferentially directing expression in seeds. Where a selectable-screenable marker gene fusion is used, the promoter will also preferably be expressed in the target tissue which is used for transformation, thereby allowing efficient selection of transformed cells. For example, callus or embryo expression of the selectable-screenable marker gene fusion would allow utilization of a selection agent for efficient recovery of transformed cells. The promoter should also not direct expression of the marker gene in the whole plant and seed, as it has been reported that some screenable marker genes may exhibit phytotoxicity. Examples of the most preferred promoters for use with the instant invention include the maize L3 oleosin, maize globulin 1 and barley LTP 2 promoters. Examples of some other suitable promoters for directing the expression of the constructs of the invention include the alpha-amylase, chitinase, beta-glucanase, cysteine proteinase, glutaredoxin, HVA1, serine carboxypeptidaseII, catalase, alpha-glucosidase, beta-amylase, VP1, and bronze2 promoters, as well as oleosin promoters in addition to the L3 oleosin promoter.

As indicated above, the constructs of the invention will preferably include, in addition to a screenable marker gene or selectable-screenable marker gene fusion, at least a first exogenous gene. For expression of exogenous genes, virtually any promoter capable of directing gene expression in plants can be used. Which promoter is used will depend on the gene being expressed and the desired pattern of expression, and will be known to those of skill in the art in light of the instant disclosure. Useful promoters for the expression of an exogenous gene include those that are inducible, viral, synthetic, constitutive, temporally regulated, spatially regulated, and spatio-temporally regulated (Chau et al., 1989; Poszkowski et al., 1989; Odell et al., 1985).

A promoter is selected for its ability to direct the transformed plant cell's or transgenic plant's transcriptional activity to the coding region. Promoters can be near-constitutive, such as the CaMV 35S promoter (Odell et al., 1985), CaMV 19S (Lawton et al., 1987), nos (Ebert et al., 1987), Adh (Walker et al., 1987), sucrose synthase (Yang & Russell, 1990), α-tubulin, actin (Wang et al., 1992), cab (Sullivan et al., 1989), PEPCase (Hudspeth & Grula, 1989)

and R gene complex-associated promoters (Chandler et al., 1989). Where the promoter is a near-constitutive promoter, increases in polypeptide expression generally are found in a variety of transformed plant tissues (e.g., callus, leaf, seed and root).

Alternatively, expression of transgenes can be directed to specific plant tissues by using vectors containing a tissue-specific promoter. An exemplary tissue-specific promoter is the lectin promoter (Vodkin et al., 1983; Lindstrom et al., 1990.). Other exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), truncated CaMV 35s (Odell et al., 1985), Potato patatin promoters (Wenzler et al., 1989), maize zein and globulin-1 promoters. Other tissue specific promoters including root cell promoters (Conkling et al., 1990) and tissue specific enhancers (Fromm et al., 1989) also are contemplated to be particularly useful, as are inducible promoters such as ABA- and turgor-inducible promoters.

Ultimately, the most desirable DNA segments for introduction into a monocot genome may be homologous genes or gene families which encode a desired trait (for example, increased yield per acre), and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Therefore, when the term "exogenous gene" is used, is it intended to include genes which are native to the host genome, but which are under the control of a novel regulatory element. Indeed, it is envisioned that a particular use of the present invention may be the production of transformants comprising a transgene which is targeted in a tissue-specific manner. For example, insect resistant genes may be expressed specifically in the whorl and collar/sheath tissues which are targets for the first and second broods, respectively, of European Corn Borer (ECB). Likewise, genes encoding proteins with particular activity against rootworm may be targeted directly to root tissues.

Vectors for use in tissue-specific targeting of gene expression in transgenic plants typically will include tissue-specific promoters and also may include other tissue-specific control elements such as enhancer sequences. Promoters which direct specific or enhanced expression in certain plant tissues will be known to those of skill in the art in light of the present disclosure.

It also is contemplated that tissue specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* (Bt) may be introduced such that it is expressed in all tissues using the 35S promoter from Cauliflower Mosaic Virus. Alternatively, a rice actin promoter or a histone promoter from a dicot or monocot species also could be used for constitutive expression of a gene. Furthermore, it is contemplated that promoters combining elements from more than one promoter may be useful. For example, U.S. Pat. No. 5,491,288 discloses combining a Cauliflower Mosaic Virus promoter with a histone promoter. Expression of an antisense transcript of the Bt gene in a maize kernel, using for example a zein promoter, would prevent accumulation of the Bt protein in seed. Hence the protein encoded by the introduced gene would be present in all tissues except the kernel. It is specifically contemplated by the inventors that a similar strategy could be used with the instant invention to direct expression of a screenable marker in seed tissue.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

It is contemplated that expression of some genes in transgenic plants will be desired only under specified conditions. For example, it is proposed that expression of certain genes that confer resistance to environmental stress factors such as drought will be desired only under actual stress conditions. It further is contemplated that expression of such genes throughout a plants development may have detrimental effects. It is known that a large number of genes exist that respond to the environment. For example, expression of some genes such as rbcS, encoding the small subunit of ribulose bisphosphate carboxylase, are regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It also is anticipated that expression of genes conferring resistance to insect predation would be desired only under conditions of actual insect infestation. Therefore, for some desired traits, inducible expression of genes in transgenic plants will be desired.

It is proposed that, in some embodiments of the present invention, expression of a gene in a transgenic plant will be desired only in a certain time period during the development of the plant. Developmental timing frequently is correlated with tissue specific gene expression. For example, expression of zein storage proteins is initiated in the endosperm about 15 days after pollination.

It also is contemplated that it may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have a gene introduced through transformation replace an existing gene in the cell.

1. Untranslated Leader Sequences

Another type of element which can regulate gene expression is the DNA sequence between the transcription initiation site and the start of the coding sequence, termed the untranslated leader sequence. The leader sequence can influence gene expression and compilations of leader sequences have been made to predict optimum or sub-optimum sequences and generate "consensus" and preferred leader sequences (Joshi, 1987). Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred.

2. Enhancers

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. In some instances these 5' enhancing elements are introns. Examples of enhancers include elements from the CaMV 35S promoter, octopine synthase genes (Ellis et al., 1987), the rice actin 1 gene, the maize alcohol dehydrogenase gene, the maize shrunken 1 gene and promoters from non-plant eukaryotes (e.g. yeast; Ma et al., 1988).

Specifically contemplated for use in accordance with the present invention are vectors which include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, may be used to increase the level of transcription from adjacent promoters when applied in the context of monocot transformation.

(ii) Terminators

Constructs will typically include the gene of interest along with a 3' end DNA sequence that acts as a signal to terminate transcription and allow for the poly-adenylation of the resultant mRNA. The most preferred 3' elements are contemplated to be those from the nopaline synthase gene of *Agrobacterium tumefaciens* (nos 3' end) (Bevan et al., 1983), the terminator for the T7 transcript from the octopine synthase gene of *Agrobacterium tumefaciens,* and the 3' end of the protease inhibitor I or II genes from potato or tomato. Regulatory elements such as Adh intron I (Callis et al., 1987), sucrose synthase intron (Vasil et al., 1989) or TMV omega element (Gallie, et al., 1989), may further be included where desired.

(iii) Transit or signal peptides

Sequences that are joined to the coding sequence of a gene, which are removed post-translationally from the initial translation product and which facilitate the transport of the protein into or through intracellular or extracellular membranes are termed transit (usually into vacuoles, vesicles, plastids and other intracellular organelles) and signal sequences (usually to the outside of the cellular membrane). By facilitating the transport of the protein into compartments inside and outside the cell these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It is further contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a protein conferring herbicide resistance, such as the mutant EPSPS protein, to a particular organelle such as the chloroplast rather than to the cytoplasm. This is exemplified by the use of the rbcS transit peptide, the chloroplast transit peptide described in European Patent No. 0189707, or the optimized transit peptide described in U.S. Pat. No. 5,510, 471, which confers plastid-specific targeting of proteins. In addition, it may be desirable to target certain genes responsible for male sterility to the mitochondria, or to target certain genes for resistance to phytopathogenic organisms to the extracellular spaces, or to target proteins to the vacuole. A further use concerns the direction of enzymes involved in amino acid biosynthesis or oil synthesis to the plastid. Such enzymes include dihydrodipicolinic acid synthase which may contribute to increasing lysine content of a feed.

VI. Exogenous Genes for Modification of Plants

A particularly important advance of the present invention is that it provides methods and compositions for the efficient identification of plant seeds comprising transgene constructs having exogenous genes in addition to marker genes. Such exogenous genes will preferably confer the host plant with a desirable phenotype and often will be genes that direct the expression of a particular protein or polypeptide product, but they also may be non-expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The inventors also contemplate that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to recipient cells with the constructs of the invention often will depend on the purpose of the transformation. One of the major purposes of transformation of crop plants is to add commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress, or oxidative stress; increased yields; food content and makeup; physical appearance; male sterility; drydown; standability; prolificacy; starch quantity and quality; oil quantity and quality; protein quality and quantity; amino acid composition; and the like. One may desire to incorporate on the constructs of the invention one or more genes conferring any such desirable trait or traits, such as, for example, a gene or genes encoding herbicide resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate3-phosphate synthase (EPSP Synthase), is normally inhibited by the herbicide N-(phosphonomethyl)glycine(glyphosate). However, genes are known that encode glyphosate-resistantEPSP synthase enzymes. These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

2. Insect Resistance

Potential insect resistance genes that can be introduced include *Bacillus thuringiensis* crystal toxin genes or Bt genes (Watrud et al., 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development also may be employed in this regard.

It is contemplated that preferred Bt genes for use in the transformation protocols disclosed herein will be those in which the coding sequence has been modified to effect increased expression in plants, and more particularly, in maize. Means for preparing synthetic genes are well known in the art and are disclosed in, for example, U.S. Pat. Nos. 5,500,365 and 5,689,052, each of the disclosures of which are specifically incorporated herein by reference in their entirety. Examples of such modified Bt toxin genes include a synthetic Bt CryIA(b) gene (Perlak et al., 1991), and the synthetic CryIA(c) gene termed 1800b (PCT Application WO 95/06128). Some examples of other Bt toxin genes known to those of skill in the art are given in Table 2 below.

TABLE 2

| Bacillus thuringiensis δ-Endotoxin Genes[a] | | |
|---|---|---|
| New Nomenclature | Old Nomenclature | GenBank Accession # |
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic maize expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972).

Further genes encoding proteins characterized as having potential insecticidal activity also may be used as transgenes in accordance herewith. Such genes include, for example, the cowpea trypsin inhibitor (CpTI; Hilder et al., 1987) which may be used as a rootworm deterrent; genes encoding avermectin (Avermectin and Abamectin., Campbell, W. C., Ed., 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can convert a non-toxic insecticide (pro-insecticide) applied to the outside of the plant into an insecticide inside the plant also are contemplated.

3. Environment or Stress Resistance

Improvement of a plant's ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance also may be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; ErdMann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol 0-methyltransferase.

It is contemplated that the expression of specific proteins also may increase drought tolerance. Three classes of Late Embryogenic Proteins have been assigned based on structural similarities (see Dure et al., 1989). All three classes of LEAs have been demonstrated in maturing (i.e. desiccating) seeds. Within these 3 types of LEA proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in corn. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993 which are incorporated herein by reference). Spatial and temporal expression patterns of these genes may enable corn to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn to utilize water more efficiently, through the introduction and expression of novel genes, will improve overall performance even when soil water availability is not limiting. By introducing genes that improve the ability of corn to maximize water usage across a full range of stresses relating to water availability, yield stability or consistency of yield performance may be realized.

4. Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses. Examples of viral and viral-like diseases, for which one could introduce resistance to in a transgenic plant in accordance with the instant invention, are listed below, in Table 3.

TABLE 3

Plant Virus and Virus-like Diseases

| DISEASE | CAUSATIVE AGENT |
| --- | --- |
| American wheat striate (wheat striate mosaic) | American wheat striate mosaic virus mosaic (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle* | Cereal chlorotic mottle virus (CCMV) |
| Corn chlorotic vein banding (Brazilian maize mosaic) | Corn chlorotic vein banding virus (CCVBV) |
| Corn lethal necrosis | Virus complex (Maize chlorotic mottle virus [MCMV] and Maize dwarf mosaic virus |

TABLE 3-continued

Plant Virus and Virus-like Diseases

| DISEASE | CAUSATIVE AGENT |
| --- | --- |
| | [MDMV] A or B or Wheat streak mosaic virus [WSMV]) |
| Cucumber mosaic | Cucumber mosaic virus (CMV) |
| Cynodon chlorotic streak*,1 | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D,B and F |
| Maize leaf fleck | Maize leaf fleck virus (MLFV) |
| Maize line* | Maize line virus (MLV) |
| Maize mosaic (corn leaf stripe, enanismo rayado) | Maize mosaic virus (MMV) |
| Maize mottle and chlorotic stunt[1] | Maize mottle and chlorotic stunt virus* |
| Maize pellucid ringspot* | Maize pellucid ringspot virus (MPRV) |
| Maize raya gruesa*,1 | Maize raya gruesa virus (MRGV) |
| maize rayado fino* (fine striping disease) | Maize rayado fino virus (MRFV) |
| Maize red leaf and red stripe* | Mollicute? |
| Maize red stripe* | Maize red stripe virus (MRSV) |
| Maize ring mottle* | Maize ring mottle virus (MRMV) |
| Maize rio IV* | Maize rio cuarto virus (MRCV) |
| Maize rough dwarf* (nanismo ruvido) | Maize rough dwarf virus (MRDV) (= Cereal tillering disease virus*) |
| Maize sterile stunt* | Maize sterile stunt virus (strains of barley yellow striate virus) |
| Maize streak* | Maize streak virus (MSV) |
| Maize stripe (maize chlorotic stripe, maize hoja blanca) | Maize stripe virus |
| Maize stunting*,1 | Maize stunting virus |
| Maize tassel abortion* | Maize tassel abortion virus (MTAV) |
| Maize vein enation* | Maize vein enation virus (MVEV) |
| Maize wallaby ear* | Maize wallaby ear virus (MWEV) |
| Maize white leaf* | Maize white leaf virus |
| Maize white line mosaic | Maize white line mosaic virus (MWLMV) |
| Millet red leaf* | Millet red leaf virus (MRLY) |
| Northern cereal mosaic* | Northern cereal mosaic virus (NCMV) |
| Oat pseudorosette* (zakuklivanie) | Oat pseudorosette virus |
| Oat sterile dwarf* | Oat sterile dwarf virus (OSDV) |
| Rice black-streaked dwarf* | Rice black-streaked dwarf virus (RBSDV) |
| Rice stripe* | Rice stripe virus (RSV) |
| Sorghum mosaic | Sorghum mosaic virus (SrMV), formerly sugarcane mosaic virus (SCMV) strains H, I and M |
| Sugarcane Fiji disease* | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Vein enation*,1 | Virus? |
| Wheat spot mosaic | Wheat spot mosaic virus (WSMV) |

*Not known to occur naturally on corn in the United States. [1]Minor viral disease.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are, β-1,3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics. Examples of bacterial and fungal diseases, including downy mildews, for which one could introduce resistance to in a transgenic plant in accordance with the instant invention, are listed below, in Tables 4, 5 and 6.

TABLE 4

Plant Bacterial Diseases

| DISEASE | CAUSATIVE AGENT |
| --- | --- |
| Bacterial leaf blight and stalk rot | *Pseudomonas avenae* subsp. avenae |
| Bacterial Leaf spot | *Xanthomonas campestris* pv. holcicola |
| Bacterial stalk rot | *Enterobacter dissolvens* = *Erwinia dissolvens* |
| Bacterial stalk and top rot | *Erwinia carotovora* subsp. carotovora, *Erwinia chpysanthemi* pv. zeae |
| Bacterial stripe | *Pseudomonas andropogonis* |
| Chocolate spot | *Pseudomonas syringae* pv. coronafaciens |
| Goss's bacterial wilt and blight (leaf freckles and wilt) | *Clavibacter michiganensis* subsp. nebraskensis = *Corynebacterium michiganense* pv. nebraskense |
| Holcus spot | *Pseudomonas syringae* pv. syringae |
| Purple leaf sheath | Hemiparasitic bacteria + (See under Fungi) |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

TABLE 5

Plant Fungal Diseases

| DISEASE | PATHOGEN |
| --- | --- |
| Anthracnose leaf blight and anthracnose stalk rot | *Colletotrichum graminicola* (teleomorph: *Glomerella graminicola* Politis), *Glomerella tucumanensis* (anamorph: *Glomerella falcatum* Went) |
| Aspergillus ear and kernel rot | *Aspergillus flavus* Link:Fr. |
| Banded leaf and sheath spot* | *Rhizoctonia solani* Kuhn = *Rhizoctonia microsclerotia* J. Matz (teleomorph: *Thanatephorus cucumeris*) |
| Black bundle disease | *Acremonium strictum* W. Gams = *Cephalosporium acremonium* Auct. non Corda |
| Black kernel rot* | *Lasiodiplodia theobromae* = *Botryodiplodia theobromae* |
| Borde blanco* | *Marasmiellus* sp. |
| Brown spot (black spot, stalk rot) | *Physoderma maydis* |
| Cephalosponum kernel rot | *Acremonium strictum* = *Cephalosporium acremonium* |
| Charcoal rot | *Macrophomina phaseolina* |
| Corticium ear rot* | *Thanatephorus cucumeris* = *Corticium sasakii* |
| Curvularia leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| Didymella leaf spot* | *Didymella exitalis* |
| Diplodia ear rot and stalk rot | *Diplodia frumenti* (teleomorph: *Botryosphaeria festucae*) |
| Diplodia ear rot, stalk rot, seed rot and seedling blight | *Diplodia maydis* = *Stenocarpella maydis* |
| Diplodia leaf spot or leaf streak | *Stenocarpella macrospora* = *Diplodia macrospora* |

*Not known to occur naturally on corn in the United States.

TABLE 6

Plant Downy Mildews

| DISEASE | CAUSATIVE AGENT |
| --- | --- |
| Brown stripe downy mildew* | *Sclerophthora rayssiae* var. zeae |
| Crazy top downy mildew | *Sclerophthora macrospora* = *Sclerospora macrospora* |
| Green ear downy mildew (graminicola downy mildew) | *Sclerospora graminicola* |

TABLE 6-continued

Plant Downy Mildews

| DISEASE | CAUSATIVE AGENT |
| --- | --- |
| Java downy mildew* | *Peronosclerospora maydis* = *Sclerospora maydis* |
| Philippine downy mildew* | *Peronosclerospora philippinensis* = *Sclerospora philippinensis* |
| Sorghum downy mildew | *Peronosclerospora sorghi* = *Sclerospora sorghi* |
| Spontaneum downy mildew* | *Peronosclerospora spontanea* = *Sclerospora spontanea* |
| Sugarcane downy mildew* | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii*. |
| Ergot* (horse's tooth, diente de caballo) | *Claviceps gigantea* (anamorph: *Sphacelia* sp.) |
| Eyespot | *Aureobasidium zeae* = *Kabatiella zeae* |
| Fusarium ear and stalk rot | *Fusarium subglutinans* = *F. moniliforme* var. *subglutinans* |
| Fusarium kernel, root and stalk rot, seed rot and seedling blight | *Fusariuin moniliforme* (teleomorph: *Gibberella fujikuroi*) |
| Fusarium stalk rot, seedling root rot | *Fusarium avenaceum* (teleomorph: *Gibberella avenacea*) |
| Gibberella ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (Cercospora leaf spot) | *Cercospora sorghi* = *C. sorghi* var. *maydis*, *C. zeae-maydis* |
| Helminthosporium root rot | *Exserohilum pedicellatum* = *Helminthosporium pedicellatum* (teleomorph: *Setosphaeria pedicellata*) |
| Hormodendrum ear rot (Cladosporium rot) | *Cladosporium cladosporioides* = *Hormodendrum cladosporioides*, *C. herbarum* (teleomorph: *Mycosphaerella tassiana*) |
| Hyalothyridium leaf spot* | *Hyalothyridium maydis* |
| Late wilt* | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicocdum nigrum*, *Exserohilum prolatum* = *Drechsleraprolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot, Helminthosporium ear rot (race 1) | *Cochliobolus carbonum* (anamorph: *Bipolaris zeicola* = *Helminthosporium carbonum*) |
| Penicillium ear rot (blue eye, blue mold) | *Penicillium* spp., *P. chrysogenum*, *P. expansum*, *P. oxalicum* |
| Phaeocytostroma stalk rot and root rot | *Phaeocytostroma ambiguum*, = *Phaeocytosporella zeae* |
| Phaeosphaeria leaf spot* | *Phaeosphaeria maydis* = *Sphaerulina maydis* |
| Physalospora ear rot (Botryosphaeria ear rot) | *Botryosphaeria festucae* = *Physalospora zeicola* (anamorph: *Diplodia frumenti*) |
| Purple leaf sheath | Hemiparasitic bacteria and fungi |
| Pyrenochaeta stalk rot and root rot | *Phoma terrestris* = *Pyrenochaeta terrestris* |
| Pythium root rot | *Pythium* spp., *P. arrhenomanes*, *P. graminicola* |
| Pythium stalk rot | *Pythium aphanidermatum* = *P. butleri* L. |
| Red kernel disease (ear mold, leaf and seed rot) | *Epicoccum nigrum* |
| Rhizoctonia ear rot (sclerotial rot) | *Rhizoctonia zeae* (teleomorph: *Waitea circinata*) |

TABLE 6-continued

Plant Downy Mildews

| DISEASE | CAUSATIVE AGENT |
| --- | --- |
| Rhizoctonia root rot and stalk rot: | Rhizoctonia solani, Rhizoctonia zeae |
| Root rots, minor | Alternaria alternata, Cercospora sorghi, Dictochaetafertills, Fusarium acuminatum (teleomorph: Gibberella acuminata), F. equiseti (teleomorph: G. intricans), F. oxysporum, F. pallidoroseum,F. poae, F. roseum, G. cyanogena, (anamorph: F. sulphureum), Microdochium bolleyi, Mucor sp., Periconia circinata, Phytophthora cactorum, P. drechsleri, P. nicotianae var. parasitica, Rhizopus arrhizus |
| Rostratum leafspot (Helminthosporium leaf disease, ear and stalk rot) | Setosphaeria rostrata, (anamorph: Exserohilum rostratum = Helminthosporium rostratum) |
| Rust, common corn | Puccinia sorghi |
| Rust, southern corn | Puccinia polysora |
| Rust, tropical corn | Physopellapallescens, P. zeae = Angiopsora zeae |
| Sclerotium ear rot* (southern blight) | Sclerotium rolfsii Sacc. (teleomorph: Athelia rolfsii) |
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F moniliforme, Gibberella zeae (anamorph: F. graminearum), Macrophomina phaseolina, Penicillium Spp.; Phomopsis sp., Pythium spp., Rhizoctonia solani, R. zeae, Sclerotium rolfsii, Spicaria sp. |
| Selenophoma leaf spot* | Selenophoma sp. |
| Sheath rot | Gaeumannomyces graminis |
| Shuck rot | Myrothecium gramineum |
| Silage mold | Monascus purpureus, M. ruber |
| Smut, common | Ustilago zeae = U. maydis |
| Smut, false | Ustilaginoidea virens |
| Smut, head | Sphacelotheca reiliana = Sporisorium holci-sorghi |
| Southern corn leaf blight and stalk rot | Cochliobolus heterostrophus (anamorph: Bipolaris maydis = Helminthosporium maydis) |
| Southern leaf spot | Stenocarpella macrospora = Diplodia macrospora |
| Stalk rots, minor | Cercospora sorghi, Fusarium episphaeria, F. merismoides, F. oxysporum Schlechtend, F. poae, F. roseum, F. solani (teleomorph: Nectria haematococca), F. tricinctum, Mariannaea elegans, Mucor sp., Rhopographus zeae, Spicaria sp. |
| Storage rots | Aspergillus spp., Penicillium spp. and other fungi |
| Tar spot* | Phyllachora maydis |
| Trichoderma ear rot and root rot | Trichoderma viride = T. lignorum teleomorph: Hypocrea sp. |
| White ear rot, root and stalk rot | Stenocarpella maydis = Diplodia zeae |
| Yellow leaf blight | Ascochyta ischaemi, Phyllosticta maydis (teleomorph: Mycosphaerella zeae-maydis) |
| Zonate leaf spot | Gloeocercospora sorghi |

*Not known to occur naturally on corn in the United States.

Plant parasitic nematodes are a cause of disease in many plants, including maize. It is proposed that it would be possible to make a plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins. Examples of nematode-associated plant diseases, for which one could introduce resistance to in a transgenic plant in accordance with the invention are given below, in Table 7.

TABLE 7

Parasitic Nematodes

| DISEASE | PATHOGEN |
| --- | --- |
| Awl | Dolichodorus spp., D. heterocephalus |
| Bulb and stem (Europe) | Ditylenchus dipsaci |
| Burrowing | Radopholus similis |
| Cyst | Heterodera avenae, H. zeae, Punctodera chalcoensis |

TABLE 7-continued

Parasitic Nematodes

| DISEASE | PATHOGEN |
| --- | --- |
| Dagger | Xiphinema spp., X. americanum, X. mediterraneum |
| False root-knot | Nacobbus dorsalis |
| Lance, Columbia | Hoplolaimus columbus |
| Lance | Hoplolaimus spp., H. galeatus |
| Lesion | Pratylenchus spp., P. brachyurus, P. crenatus, P. hexincisus, P. neglectus, P. penetrans, P. scribneri, P. thornei, P. zeae |
| Needle | Longidorus spp., L. breviannulatus |
| Ring | Criconemella spp., C. ornata |
| Root-knot | Meloidogyne spp., M. chitwoodi, M. incognita, M. javanica |
| Spiral | Helicotylenchus spp. |
| Sting | Belonoiaimus spp., B. longicaudatus |
| Stubby-root | Paratrichodorus spp., P. christiei, P. minor, Quinisulcius acutus, Trichodorus spp. |
| Stunt | Tylenchorhynchus dubius |

5. Mycotoxin Reduction/Elimination

Production of mycotoxins, including aflatoxin and fumonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It also is proposed that it may be possible to introduce novel genes into monocotyledonous plants such as maize that would inhibit synthesis of the mycotoxin without interfering with fungal growth. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

6. Grain Composition or Quality

Genes may be introduced into plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes, but in no way provide an exhaustive list of possibilities.

The protein of cereal grains including maize is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It also is proposed that the protein composition of the grain may be modified through the phenomenon of co-suppression, i.e., inhibition of expression of an endogenous gene through the expression of an identical structural gene or gene fragment introduced through transformation (Goring et al., 1991). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described. The improvements may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvements in feed or food value, genes also may be introduced which improve the processing of corn and improve the value of the products resulting from the processing. The primary method of processing corn is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or combination. DNA such as antisense constructs also may be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties also may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $C_8$ to $C_{12}$ saturated fatty acids.

Improvements in the other major corn wetmilling products, corn gluten meal and corn gluten feed, also may be achieved by the introduction of genes to obtain novel corn plants. Representative possibilities include but are not limited to those described above for improvement of food and feed value.

In addition, it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, and industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

7. Plant Agronomic Characteristics

Two of the factors determining where corn or other crops can be grown are the average daily temperature during the growing season and the length of time between frosts. Within the areas where it is possible to grow corn, there are varying limitations on the maximal time it is allowed to grow to maturity and be harvested. The corn to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest, it is desirable to have maximal drying take place in the field to minimize the amount of energy required for additional drying post-harvest. Also, the more readily the grain can dry down, the more time there is available for growth and kernel fill. It is considered that genes that influence maturity and/or dry down can be identified and introduced into corn lines using transformation techniques to create new corn varieties adapted to different growing locations or the same growing location, but having improved yield to moisture ratio at harvest. Expression of genes that are involved in regulation of plant development may be especially useful, e.g., the liguleless and rough sheath genes that have been identified in corn.

It is contemplated that genes may be introduced into monocots that would improve standability and other plant growth characteristics. Expression of novel genes which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in corn may be advantageous. Expression of such a gene may reduce apical dominance, confer semidwarfism on a plant, and increase shade tolerance (U.S. Pat. No. 5,268,526). Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would be advantageous. For example, a nonyellowing mutant has been identified in *Festuca pratensis* (Davies et al., 1990). Expression of this gene as well as others may prevent premature breakdown of chlorophyll and thus maintain canopy function.

8. Nutrient Utilization

The ability to utilize available nutrients may be a limiting factor in growth of crop plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It is further contemplated that enhanced nitrogen utilization by the corn plant is desirable. Expression of a glutamate dehydrogenase gene in maize, e.g., *E. coli* gdhA genes, may lead to increased fixation of nitrogen in organic compounds. Furthermore, expression of gdhA in corn may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

9. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

10. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding a Bt gene that confers insect resistance on the plant may be introduced into a plant together with a bar gene that is useful as a selectable marker and confers resistance to the herbicide Liberty® on the plant. However, it may not be desirable to have an insect resistant plant that also is resistant to the herbicide Liberty®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (NPT II) has been investigated as a negative selectable marker in tobacco (*Nicotiana tabacum*) and *Arabidopsis thaliana* (Xiang. and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers also may be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, 1993). In the presence of this enzyme the compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

It also is contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

(vi) Non-Protein-Expressing Sequences

1. RNA-Expressing

DNA may be introduced into crop plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Genes also may be constructed or isolated, which when transcribed produce RNA enzymes, or ribozymes, which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above that may be affected by antisense RNA.

It also is possible that genes may be introduced to produce novel transgenic plants which have reduced expression of a native gene product by a mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

2. Non-RNA-Expressing

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

VII. Transformation

There are many methods for transforming DNA segments into cells, but not all are suitable for delivering DNA to plant cells. Suitable methods for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, maize cells as well as those of virtually any other plant species may be stably transformed, and these cells developed into transgenic plants. In certain embodiments, acceleration methods are preferred and include, for example, microprojectile bombardment and the like.

(i) Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin, 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

(ii) Microprojectile Bombardment

A preferred method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

(iii) Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and maize (Ishidia et al., 1996).

Modem Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

(iv) Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

VIII. Optimization of Microprooectile Bombardment

For microprojectile bombardment transformation using the constructs of the instant invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that prebombardment manipulations are especially important for successful transformation of immature embryos.

Accordingly, it is contemplated that one may wish to adjust various bombardment parameters in small scale studies to fully optimize the conditions. One may particularly wish to adjust physical parameters such as DNA concentration, gap distance, flight distance, tissue distance, and helium pressure. It is further contemplated that the grade of helium may effect transformation efficiency. For example, differences in transformation efficiencies may be witnessed between bombardments using industrial grade (99.99% pure) or ultra pure helium (99.999% pure), although it is not currently clear which is more advantageous for use in bombardment. One also may optimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

Other physical factors include those that involve manipulating the DNA/microprojectile precipitate or those that affect the flight and velocity of either the macro- or microprojectiles. Biological factors include all steps involved in manipulation of cells immediately before and after bombardment. The prebombardment culturing conditions, such as osmotic environment, the bombardment parameters, and the plasmid configuration have been adjusted to yield the maximum numbers of stable transformants.

(i) Physical Parameters

1. Gap Distance

The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and therefore the total number of recovered stable transformants.

2. Flight Distance

The fixed nest (contained within the variable nest) can be varied between 0.5 and 2.25 cm in predetermined 0.5 cm increments by the placement of spacer rings to adjust the flight path traversed by the macroprojectile. Short flight paths allow for greater stability of the macroprojectile in flight but reduce the overall velocity of the microprojectiles. Increased stability in flight increases, for example, the number of centered GUS foci. Greater flight distances (up to some point) increase velocity but also increase instability in flight. Based on observations, it is recommended that bombardments typically be done with a flight path length of about 1.0 cm to 1.5 cm.

3. Tissue Distance

Placement of tissue within the gun chamber can have significant effects on microprojectile penetration. Increasing the flight path of the microprojectiles will decrease velocity and trauma associated with the shock wave. A decrease in velocity also will result in shallower penetration of the microprojectiles.

4. Helium Pressure

By manipulation of the type and number of rupture disks, pressure can be varied between 400 and 2000 psi within the gas acceleration tube. Optimum pressure for stable transformation has been determined to be between 1000 and 1200 psi.

5. Coating of Microprojectiles

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of interactions between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It is further contemplated that transformation of a target cell may occur by way of direct illegitimate or homology-dependent recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may occur.

Any technique for coating microprojectiles which allows for delivery of transforming DNA to the target cells may be used. Methods for coating microprojectiles which have been demonstrated to work well with the current invention have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

6. Transforming DNA

As disclosed above, it further is proposed, that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

Various other methods also may be used to increase transformation efficiency and/or increase the relative proportion of low-copy transformation events. For example, the inventors contemplate end-modifying transforming DNA with alkaline phosphatase or an agent which will blunt DNA ends prior to transformation. Still further, an inert carrier DNA may be included with the transforming DNA, thereby lowering the effective transforming DNA concentration without lowering the overall amount of DNA used. These techniques are described in further detail in U.S. Ser. No. 08/995,451, filed Dec. 22, 1997, the disclosure of which is specifically incorporated herein by reference in its entirety.

(ii) Biological Parameters

Culturing conditions and other factors can influence the physiological state of the target cells and may have profound effects on transformation and integration efficiencies. First, the act of bombardment could stimulate the production of ethylene which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. For example, synchronization may be achieved using cold treatment, amino acid starvation, or other cell cycle-arresting agents. Third, the degree of tissue hydration also may contribute to the amount of trauma associated with bombardment as well as the ability of the microprojectiles to penetrate cell walls.

The position and orientation of an embryo or other target tissue relative to the particle trajectory also may be important. For example, the PDS-1000 biolistics device does not produce a uniform spread of particles over the surface of a target petri dish. The velocity of particles in the center of the plate is higher than the particle velocity at further distances from the center of the petri dish. Therefore, it is advantageous to situate target tissue on the petri dish such as to avoid the center of the dish, referred to by some as the "zone of death." Furthermore, orientation of the target tissue with regard to the trajectory of targets also can be important. It is contemplated that it is desirable to orient the tissue most likely to regenerate a plant toward the particle stream. For example, the scutellum of an immature embryo comprises the cells of greatest embryogenic potential and therefore should be oriented toward the particle stream.

It also has been reported that slightly plasmolyzed yeast cells allow increased transformation efficiencies (Armaleo et al., 1990). It was hypothesized that the altered osmotic state of the cells helped to reduce trauma associated with the penetration of the microprojectile. Additionally, the growth and cell cycle stage may be important with respect to transformation.

1. Osmotic Adjustment

It has been suggested that osmotic pre-treatment could potentially reduce bombardment associated injury as a result of the decreased turgor pressure of the plasmolyzed cell. In a previous study, the number of cells transiently expressing GUS increased following subculture into both fresh medium and osmotically adjusted medium (U.S. Ser. No. 08/113,561, filed Aug. 25, 1993, specifically incorporated herein by reference in its entirety). Pretreatment times of 90 minutes showed higher numbers of GUS expressing foci than shorter times. Cells incubated in 500 mOSM/kg medium for 90 minutes showed an approximately 3.5 fold increase in transient GUS foci than the control. Preferably, cells are precultured for 4–5 hours prior to bombardment on culture medium containing 12% sucrose. A second culture on 12% sucrose may be performed for 16–24 hours following bombardment. Alternatively, cells are pretreated on 0.2M mannitol or 12% sucrose for 3–5 hours prior to bombardment. It is contemplated that pretreatment of cells with other osmotically active solutes for a period of 1–6 hours also may be desirable.

2. Plasmid Configuration

In some instances, it will be desirable to deliver DNA to maize cells that does not contain DNA sequences necessary for maintenance of the plasmid vector in the bacterial host, e.g., *E. coli*, such as antibiotic resistance genes, including but not limited to ampicillin, kanamycin, and tetracycline resistance, and prokaryotic origins of DNA replication. In such case, a DNA fragment containing the transforming DNA may be purified prior to transformation. An exemplary method of purification is gel electrophoresis on a 1.2% low melting temperature agarose gel, followed by recovery from the agarose gel by melting gel slices in a 6–10 fold excess of Tris-EDTA buffer (10 mM Tris-HCl pH 8.0, 1 mM EDTA, 70° C.–72° C.); frozen and thawed (37° C.); and the agarose pelleted by centrifugation. A Qiagen Q-100 column then may be used for purification of DNA. For efficient recovery of DNA, the flow rate of the column may be adjusted to 40 ml/hr.

Isolated DNA fragments can be recovered from agarose gels using a variety of electroelution techniques, enzyme digestion of the agarose, or binding of DNA to glass beads (e.g., Gene Clean™ or EluQuick™). In addition, HPLC and/or use of magnetic particles may be used to isolate DNA fragments. As an alternative to isolation of DNA fragments, a plasmid vector can be digested with a restriction enzyme and this DNA delivered to maize cells without prior purification of the expression cassette fragment.

IX. Recipient Cells for Transformation

Tissue culture requires media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, maize cells will grow in suspension or on solid medium, but regeneration of plants from suspension cultures requires transfer from liquid to solid media at some point in development. The type and extent of differentiation of cells in culture will be affected not only by the type of media used and by the environment, for example, pH and light, but also by whether media is solid or liquid. Table 8 illustrates the composition of various media useful for creation of recipient cells and for plant regeneration.

Recipient cell targets include, but are not limited to, meristem cells, Type I, Type II, and Type III callus, immature embryos and gametic cells such as microspores, pollen, sperm and egg cells. It is contemplated that any cell from which a fertile plant may be regenerated is useful as a recipient cell. Type I, Type II, and Type III callus may be initiated from tissue sources including, but not limited to, immature embryos, seedling apical meristems, microspores and the like. Those cells which are capable of proliferating as callus also are recipient cells for genetic transformation. The present invention provides techniques for transforming immature embryos and subsequent regeneration of fertile transgenic plants. Transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization Direct pollen transformation, or transformation of other germline cells such as microspores or megaspores would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Cultured plant cells that can serve as recipient cells for transforming with desired DNA segments may be any plant cells including corn cells, and more specifically, cells from *Zea mays* L. Somatic cells are of various types. Embryogenic cells are one example of somatic cells which may be induced to regenerate a plant through embryo formation. Non-embryogenic cells are those which typically will not respond in such a fashion. An example of non-embryogenic cells are certain Black Mexican Sweet (BMS) corn cells.

The development of embryogenic maize calli and suspension cultures useful in the context of the present invention, e.g., as recipient cells for transformation, has been described in U.S. Pat. Nos. 5,134,074; and 5,489,520; each of which is incorporated herein by reference in its entirety.

Certain techniques may be used that enrich recipient cells within a cell population. For example, Type II callus development, followed by manual selection and culture of friable, embryogenic tissue, generally results in an enrichment of recipient cells for use in transformation. Suspension culturing, particularly using the media disclosed herein, may improve the ratio of recipient to non-recipient cells in any given population. Manual selection techniques which can be employed to select recipient cells may include, e.g., assessing cell morphology and differentiation, or may use various physical or biological means. Cryopreservation is a possible method of selecting for recipient cells.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 $\mu$m), and capable of sustained divisions and somatic proembryo formation.

It is proposed that other means for identifying such cells also may be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers including glutamate dehydrogenase may lead to some degree of false positives from non-embryogenic cells such as rooty cells which nonetheless have a relatively high metabolic activity.

(i) Culturing Cells to be Recipients for Transformation

The inventors believe that the ability to prepare and cryopreserve cultures of maize cells is important to certain aspects of the present invention, in that it provides a means for reproducibly and successfully preparing cells for particle-mediated transformation. A variety of different types of media have been developed by the inventors and employed in carrying out various aspects of the invention. The following table, Table 8, sets forth the composition of the media preferred by the inventors for carrying out these aspects of the invention.

TABLE 8

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 7 | MS* | 2% | 6.0 | .25 mg thiamine<br>.5 mg BAP<br>.5 mg NAA<br>Bactoagar |
| 10 | MS | 2% | 6.0 | .25 mg thiamine<br>1 mg BAP<br>1 mg 2,4-D<br>400 mg L-proline<br>Bactoagar |
| 19 | MS | 2% | 6.0 | .25 mg thiamine<br>.25 mg BAP<br>.25 mg NAA<br>Bactoagar |
| 20 | MS | 3% | 6.0 | .25 mg<br>1 mg BAP<br>1 mg NAA<br>Bactoagar |
| 52 | MS | 2% | 6.0 | .25 mg thiamine<br>1 mg 2,4-D<br>$10^{-7}$ M ABA<br>BACTOAGAR |
| 101 | MS | 3% | 6.0 | MS vitamins<br>100 mg myo-inositol<br>Bactoagar |
| 142 | MS | 6% | 6.0 | MS vitamins<br>5 mg BAP<br>0.186 mg NAA<br>0.175 mg IAA<br>0.403 mg 2IP<br>Bactoagar |
| 157 | MS | 6% | 6.0 | MS vitamins<br>100 mg myo-inositol<br>Bactoagar |
| 163 | MS | 3% | 6.0 | MS vitamins<br>3.3 mg dicamba<br>100 mg myo-inositol<br>Bactoagar |
| 171 | MS | 3% | 6.0 | MS vitamins<br>.25 mg 2,4-D<br>10 mg BAP<br>100 mg myo-inositol<br>Bactoagar |
| 173 | MS | 6% | 6.0 | MS vitamins<br>5 mp BAP<br>.186 mg NAA<br>.175 mg IAA<br>.403 mg 2IP<br>$10^{-7}$ M ABA<br>200 mg myo-inositol<br>Bactoagar |
| 177 | MS | 3% | 6.0 | MS vitamins<br>.25 mg 2,4-D<br>10 mg BAP<br>$10^{-7}$ M ABA<br>100 mg myo-inositol<br>Bactoagar |
| 185 | MS | — | 5.8 | 3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA |

TABLE 8-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 201 | N6 | 2% | 5.8 | .5 mg niacin<br>800 mg L-asparagine<br>100 mg casamino acids<br>20 g sorbitol<br>1.4 g L-proline<br>100 mg myo-inositol<br>Gelgro<br>N6 vitamins<br>2 mg L-glycine<br>1 mg 2,4-D<br>100 mg casein hydrolysate<br>2.9 g L-proline<br>Gelgro |
| 205 | N6 | 2% | 5.8 | N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 mg Ca pantothenate<br>100 mg myo-inositol<br>790 mg L-asparagine<br>100 mg casein hydrolysate<br>1.4 g L-proline<br>Hazelton agar****<br>2 mg L-glycine |
| 212 | N6 | 3% | 5.5 | N6 vitamins<br>2 mg L-glycine<br>2 mg 2,4-D<br>250 mg Ca pantothenate<br>100 mg myo-inositol<br>100 mg casein hydrolysate<br>1.4 g L-proline<br>Hazelton agar**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro |
| 273 (also,201V,N6 236S, 201D, 2071, 236G,201SV, 2377, and 201BV) | | 2% | 5.8 | N6 vitamins<br>2 mg L-glycine<br>1 mg 2,4-D<br>16.9 mg AgNO$_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>Gelgro**** |
| 288 | N6 | 3% | | 3.3 mg dicamba<br>1 mg thiamine<br>.5 mg niacin<br>.8 g L-asparagine<br>100 mg myo-inositol<br>1.4 g L-proline<br>100 mg casein hydrolysate<br>16.9 mg AgNO$_3$<br>Gelgro |
| 401 | MS | 3% | 6.0 | 3.73 mg Na$_2$EDTA<br>.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 402 | MS | 3% | 6.0 | 3.73 mg Na$_2$EDTA<br>.25 mg thiamine<br>1 mg 2,4-D<br>200 mg casein hydrolysate<br>2.9 g L-proline<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>.25 mg thiamine<br>9.9 mg dicamba<br>200 mg casein hydrolysate<br>2.9 g L-proline<br>500 mg K$_2$SO$_4$<br>400 mg KH$_2$PO$_4$<br>100 mg myo-inositol |
| 501 | Clark's Medium*** | 2% | 5.7 | |
| 607 | 1/2 × MS | 3% | 5.8 | 1 mg thiamine<br>1 mg niacin<br>Gelrite |
| 615 | MS | 3% | 6.0 | MS vitamins<br>6 mg BAP<br>100 mg myo-inositol<br>Bactoagar |
| 617 | 1/2 × MS | 1.5% | 6.0 | MS vitamins<br>50 mg myo-inositol<br>Bactoagar |
| 708 | N6 | 2% | 5.8 | N6 vitamins<br>2 mg L-glycine<br>1.5 mg 2,4-D<br>200 mg casein hydrolysate<br>0.69 g L-proline<br>Gelrite |
| 721 | N6 | 2% | 5.8 | 3.3 mg dicamba<br>1 mg thiamine |

TABLE 8-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | OTHER COMPONENTS** pH (Amount/L) |
|---|---|---|---|
| | | | .5 mg niacin<br>800 mg L-asparagine<br>100 mg myo-inositol<br>100 mg casein hydrolysate<br>1.4 g L-proline<br>54.65 g mannitol<br>Gelgro |
| 726 | N6 | 3% | 5.8 3.3 mg dicamba<br>.5 mg niacin<br>1 mg thiamine<br>800 mg L-asparagine<br>100 mg myo-inositol<br>100 mg casein hydrolysate<br>1.4 g L-proline |
| 727 | N6 | 3% | 5.8 N6 vitamins<br>2 mg L-glycine<br>9.9 mg dicamba<br>100 mg casein hydrolysate<br>2.9 g L-proline<br>Gelgro |
| 728 | N6 | 3% | 5.8 N6 vitamins<br>2 mg L-glycine<br>9.9 mg dicamba<br>16.9 mg AgNO$_3$<br>100 mg casein hydrolysate<br>2.9 g L-proline<br>Gelgro |
| 734 | N6 | 2% | 5.8 N6 vitamins<br>2 mg L-glycine<br>1.5 mg 2,4-D<br>14 g Fe sequestreene<br>(replaces Fe-EDTA)<br>200 mg casein hydrolyste<br>0.69 g L-proline<br>Gelrite |
| 735 | N6 | 2% | 5.8 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>Gelgro |
| 2004 | N6 | 3% | 5.8 1 mg thiamine<br>0.5 mg niacin<br>3.3 mg dicamba<br>17 mg AgNO$_3$<br>1.4 g L-proline<br>0.8 g L-asparagine<br>100 mg casein hydrolysate<br>100 mg myo-inositol<br>Gelrite |
| 2008 | N6 | 3% | 5.8 1 mg thiamine<br>0.5 mg niacin<br>3.3 mg dicamba<br>1.4 g L-proline<br>0.8 g L-asparagine<br>Gelrite |

*Basic MS medium described in Murashige and Skoog (1962). This medium is typically modified by decreasing the NH$_4$NO$_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2,isopentyl adenine
2,4-D = 2,4-Dichlorophenoxyacetic Acid
BAP = 6-Benzyl aminopurine
ABA = abscisic acid
***Basic medium described in Clark (1982)
****These media may be made with or without solidifying agent.

A number of exemplary maize cultures which may be used for transformation have been developed and are disclosed in U.S. patent application Ser. No. 08/113,561, filed Aug. 25, 1993, the disclosure of which is specifically incorporated herein by reference.

(ii) Media

In certain embodiments, recipient cells are selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components (see, Table 8), but may differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells previously have been described. Examples of these media include, but are not limited to, the N6 medium described by Chu et al. (1975) and MS media (Murashige and Skoog, 1962). The inventors have discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

(iii) Maintenance

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It also is contemplated that passing cell cultures through a 1.9 mm sieve is useful in maintaining the friability of a callus or suspension culture and may be beneficial in enriching for transformable cells.

(iv) Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23 M proline and 0.23 M glucose. The mixture was allowed to equilibrate at 0° C. for 30 minutes, during which time the cell suspension/ cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e., there is little free water left in the cells), and they could be safely plunged into liquid nitrogen for storage. The paucity of free water remaining in the cells in conjunction with the rapid cooling rates from −35° C. to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). The cryoprotectant solution is removed by pipetting. Culture medium comprised a callus proliferation medium with increased osmotic strength. Dilution of the cryoprotectant occurred slowly as the solutes diffused away through the filter and nutrients diffused upward to the recovering cells. Once subsequent growth of the thawed cells was noted, the growing tissue was transferred to fresh culture medium. If initiation of a suspension culture was desired, the cell clusters were transferred back into liquid suspension medium as soon as sufficient cell mass had been regained (usually within 1 to 2 weeks). Alternatively, cells were cultured on solid callus proliferation medium. After the culture was reestablished in liquid (within 1 to 2 additional weeks), it was used for transformation experiments. When desired, previously cryopreserved cultures may be frozen again for storage.

X. Production and Characterization of Transgenic Plants

After effecting delivery of exogenous DNA to recipient cells, the next steps generally concern identifying the transformed cells for further culturing and plant regeneration. As disclosed herein, in order to improve the ability to identify transformants, the constructs of the invention preferably include selectable and screenable marker gene function, and additionally, one or more expressible gene of interest. The selectable marker gene offers an efficient means for the primary identification of transformed cells, while the screenable marker system offers an efficient means for selection of seeds which have inherited the transgene construct. It is specifically contemplated by the inventors, however, that cells, clusters of cells (for example, callus or immature embryos), or plants could be selected with either the selectable or screenable marker functions of the constructs of the instant invention. For instance, transformed cells could be identified which express GFP, and transformed plants could be selected by treatment with a selection agent such as paromomycin.

(i) Selection

It is believed that DNA is introduced into only a small percentage of target cells in any one experiment. In order to provide an efficient system for identification of those cells receiving DNA and integrating it into their genomes one may employ a means for selecting those cells that are stably transformed. In a preferred embodiment of the invention, cells are transformed with a gene fusion between a selectable and a screenable marker gene which encodes a fusion protein having selectable and screenable marker gene activities, and the transformed cells are selected by exposure to appropriate selection agent. One exemplary embodiment of a selectable marker is a gene which confers resistance to some normally inhibitory agent, such as an antibiotic or herbicide. In particular, genes conferring resistance to aminoglycoside antibiotics, for example, neomycin phosphotransferase II (NPT II) or NPTI, are deemed especially useful in this respect. Examples of aminoglycoside antibiotics which may be used for selection with these genes include neomycin, kanamycin and paromomycin. Where NPTII is used with maize cells, paromomycin is preferred for selection.

To select potentially transformed cells, the cells are first exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

A herbicide which has been used successfully as a selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block, 1987) and Brassica (De Block, 1989) plants. In previous reports, some transgenic plants which expressed the resistance gene were completely resistant to commercial formulations of PPT and bialaphos in greenhouses.

Another example of a herbicide which can be used for selection of transformed cell lines is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

It is further contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. patent application No. 08/113,561, filed Aug. 25, 1993; U.S. Pat. Nos. 5,508,468; 5,508,468).

Alternatively, a gene encoding an anthranilate synthase gene which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468; and U.S. Ser. No. 08/604,789.

The neo gene, encoding the NPTII protein, is particularly useful for selection of transformed plant cells. The neo gene was isolated from the transposon Tn5 of *E. coli* and encodes a protein consisting of 264 amino acids (Beck et al., 1982). Expression of the neo gene in plant cells confers resistance to amino glycoside antibiotics (such as kanamycin, paromomycin, and G418) by phosphorylation of the 3' hydroxyl group of the antibiotics (Bryan, 1984). The neo gene has been successfully used as a selectable marker for transformation of a wide range of plant species.

(ii) Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 8) by including further substances such as growth regulators. A preferred growth regulator for such purposes is dicamba or 2,4-D. However, other growth regulators may be employed, including NAA, NAA+2,4-D or perhaps even picloram. Media improvement in these and similar ways have been found to facilitate the growth of cells at specific developmental stages. Tissue may be maintained on a basic media with growth regulators until sufficient tissue is available to begin plant regeneration efforts, or following repeated rounds of manual selection until the morphology of the tissue is suitable for regeneration, at least two weeks, then transferred to media conducive to maturation of embryoids. Cultures are transferred about every two weeks on this medium, although the time between subcultures may vary depending on the rate of growth of the cells. For example, cultures may be transferred at 3 week intervals. Shoot development will signal the time to transfer to medium lacking growth regulators.

The transformed cells, identified by selection or screening and cultured in an appropriate medium that supports regeneration, then will be allowed to mature into plants. Developing plantlets are transferred to soilless plant growth mix, and hardened, e.g., in an environmentally controlled chamber at about 85% relative humidity, 600 ppm $CO_2$, and 25–250 microeinsteins $m^{-2}s^{-1}$ of light. Plants preferably are matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes, Plant Cons and Phytatrays. Regenerating plants preferably are grown at about 19° C. to 280C. After the regenerating plants have reached the stage of shoot and root development, they may be transferred to a greenhouse for further growth and testing.

It should be noted, however, that kernels on transformed plants may occasionally require embryo rescue due to cessation of kernel development and premature senescence of plants. To rescue developing embryos, they are excised from surface-disinfected kernels 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Smaller embryos may be cultured for one week on media containing the above ingredients along with $10^{-5}M$ abscisic acid and then transferred to growth regulator-free medium for germination.

XI. Genetic Analysis of Transgenic Plants

In particular embodiments of the invention, molecular genetic techniques may be used for detecting the presence or expression of transgenes in plants. For example, the expression of a transgene construct in a particular tissue could be confirmed by performing of assays. The method of assaying may comprise determining the level of protein expressed by the transgene or by determining specific alterations in the expressed product. Such assays may in some cases be faster, more accurate or less expensive than conventional screening assays.

The biological sample may potentially be any type of plant tissue. Nucleic acid may be isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants.

A variety of different assays are contemplated in the screening of transgenic plants created using the methods of the current invention. These techniques can be used to detect for both the presence of particular genes as well as rearrangements that may have occurred in the gene construct. The techniques include but are not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein), an antigen (biotin, streptavidin, digoxigenin), or a chemilluminscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases and are described in WO 90/07641, filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases can be present. The other two bases can be added as biotinylated derivatives for easy detection. A similar approach is used in SDA. Target specific sequences also can be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependant synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case, the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohlman, M. A., In: *PCR PROTOCOLS. A GUIDE TO METHODS AND APPLICATIONS,* Academic Press, N.Y., 1990; Ohara et al., 1989; each incorporated herein by reference in their entirety).

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used.

(vi) Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from plants. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

(vii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991).

XII. Site Specific Integration or Excision of Transgenes

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527,695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5-4.2 \times 10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site—specific recombination sequences) and a specific enzyme (the site—specific recombinase). The site—specific recombinase will catalyze a recombination reaction only between two site—specific recombination sequences.

A number of different site specific recombinase systems could be employed in accordance with the instant invention, including, but not limited to, the Cre/lox system of bacteriophage P1(U.S. Pat. No. 5,658,772, specifically incorporated herein by reference in its entirety), the FLP/FRT system of yeast (Golic and Lindquist, 1989), the Gin recombinase of phage Mu (Maeser et al., 1991), the Pin recombinase of E. coli (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently in plant cells. Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA Segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

XIII. Definitions

Aleurone-specific promoter: A promoter which directs the expression of a gene preferentially in the aleurone and/or embryo of a plant seed. By "preferentially," it is meant a promoter which expresses a screenable marker gene at least a 50% greater level in the aleurone of a seed than in vegetative tissue or in endosperm tissue.

Automated: When used in the context of seed selection or screening, this term refers to the use of an apparatus or machine for the identification and determination of seeds which express a given screenable marker.

Exogenous gene: A gene which is not naturally found in the host genome. In this respect, the gene itself may be native to the host genome, however, the exogenous gene will have been modified by the addition or deletion of one or more different regulatory or other elements.

Expression: The combination of intracellular processes, including transcription and translation undergone by a coding DNA molecule in the production of a polypeptide.

Marker Gene: A gene which confers one or more recognizable phenotypes upon a plant cell, plant, plant part, or seed.

Progeny: Any subsequent generation, including the seeds and plants therefrom, which is derived from a particular parental plant or set of parental plants.

Promoter: A recognition site on a DNA sequence or group of DNA sequences that provide an expression control element for a structural gene or gene fusion and to which RNA polymerase specifically binds and initiates RNA synthesis (transcription) of that gene.

Regeneration: The process of growing a plant from a plant cell (e.g., plant protoplast or explant).

Screenable marker gene: A gene which encodes a cellular product providing a cell, cell cluster, plant, plant part or seed with a recognizable phenotype.

Selectable marker gene: A gene which encodes a cellular product that provides a cell, cell cluster, plant, plant part or seed with resistance to one or more selective agents, for example, a herbicide or antibiotic.

Selectable-screenable marker gene fusion: A gene fusion between a selectable and a screenable marker gene, the polypeptide product of which comprises both a screenable and a selectable marker gene function.

Transformation: A process of introducing an exogenous DNA sequence or construct (e.g., a vector or expression cassette) into a cell or protoplast in which that exogenous DNA is incorporated into a chromosome or is capable of autonomous replication.

Transformed cell: A cell whose DNA complement has been altered by the introduction of an exogenous DNA molecule into that cell.

Transgene: A segment of DNA which is incorporated into a host genome or is capable of autonomous replication within a host cell and is capable of causing the expression of one or more cellular products. Exemplary transgenes will provide the host cell, or plants regenerated therefrom, with a novel phenotype relative to the corresponding non-transformed cell or plant.

Transgenic cell: Any cell derived or regenerated from a transformed cell and comprising a transgene. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny of any subsequent generation derived therefrom, of a transformed plant cell or protoplast comprising a transgene, wherein the transgene comprises an introduced exogenous DNA molecule not originally present in a native, non-transgenic plant of the same strain. The transgenic plant may additionally contain sequences which are native to the plant being transformed, but wherein the "exogenous" gene has been altered by gene technological means in order to alter the level or pattern of expression of the gene.

Transit Peptide: A polypeptide sequence which is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Generation of GFP::NPTII Fusion Protein Constructs

Protein coding sequences for each of two green fluorescent proteins (GFPs) were individually fused to the neomycin phosphotransferase (NPTII) protein coding sequence by a cloning strategy which allowed for generation of in-frame translational fusions. The preparation of these constructs was as follows. Primers were designed for amplification of a GFP sequence, herein designated as MGFP, reported by Pang et al. (Plant Phys. 112:893–900, 1996). These primers correspond to nucleotide positions 16–32 (M-FP 5'NCO; SEQ ID NO:7), including the translation initiation codon, and nucleotide positions 903–922 (M-FP 3'BAM; SEQ ID NO:8), excluding the stop codon, of the above reported sequence. This strategy allowed for the addition of NcoI and BamHI restriction sites to facilitate subsequent cloning manipulation steps. The sequence of the primers was as given below:

M-FP 5'NCO AACCATGGGCAAGGGCG
M-FP 3'BAM CTGGATCCCTTGTAGAGTTCATC-CATGC

The plasmid pMON30107 (Pang et al., 1996) was used as template for PCR amplification with these primers by using the following conditions with a HF PCR Kit (Boehringer Mannheim; Indianapolis, Ind.).
100 pg template
200 μM dATP
200 μM dCTP
200 μM dGTP
200 μM dTTP
500 nM each primer
3.75 mM MgCl$_2$
Amplification was performed by using a Robocycler apparatus (Stratagene, La Jolla, Calif.) programmed as follows:

| 95° | 2 min. | 1 cycle |
|---|---|---|
| 94° | 1 min. | |
| 56–67° gradient | 1 min. | |
| 72° | 1 min. | 32 cycles |
| 72° | 4 min. | 1 cycle |
| 6° | hold | |

PCR amplification yielded the expected 915 bp fragment, which was purified by gel electrophoresis, band excision, and DNA elution by using the components of the Genelute kit (Supelco; Bellafonte, Pa.) and ligated into the plasmid cloning vector pCR2.1 (Invitrogen; Carlsbad, Calif.) in a reaction containing T4 DNA ligase from Boehringer Mannheim (Indianapolis, Ind.) using the reaction buffer provided by the manufacturer. The clone containing the MGFP amplification product was designated DV124.

Another GFP sequence was obtained from the plasmid EGFP (Clontech: Palo Alto, Calif.; Catalog No. 6077-1). Primers were designed using same strategy as above, including the translation initiation codon in the 5' primer (FP 5' NCO2; SEQ ID NO:9) and excluding the stop codon in the 3' primer (FP 3' BAM; SEQ ID NO: 10):
FP 5' NCO2-CCGGCCATGGTGAGCAAGGGCG
FP 3' BAM-CTGGATCCCTTGTACAGCTCGTCCATGC PCR amplification conditions for the EGFP sequence, carried out using the Clontech EGFP plasmid as template and the primers "FP 5' NCO2" and "FP 3' BAM," were identical to those described above for the MGFP sequence.

PCR amplification yielded the expected 731 bp fragment, which was subsequently purified by gel electrophoresis, band excision, and DNA elution by using the components of the Genelute kit (Supelco; Bellafonte, Pa.) and ligated into the plasmid cloning vector pCR2.1 (Invitrogen; Carlsbad, Calif.) in a reaction containing T4 DNA ligase from Boehringer Mannheim (Indianapolis, Ind.) using the reaction buffer provided by the manufacturer. The clone containing the EGFP amplification product was designated DV123.

The NPTII protein coding sequence was amplified by using a similar strategy to that above, with the exception that the start codon was excluded from the 5' primer and the stop codon was included in the 3' primer. Primers corresponded to nucleotide position 528–548 (NEO5' BAM; SEQ ID NO:11) or positions 1299–1316 (NEO3' SAC; SEQ ID NO:12) of the NPTII sequence contained in pDPG832. These primers contained either an additional BamHI "tail" (NEO5' BAM) or Sac1 "tail" (NEO3' SAC). Amplification and cycling conditions were identical to those used for the EGFP reaction described above but using 100 pg pDPG 832 as template. The expected 805 bp band was purified by gel electrophoresis, band excision, and DNA elution by using the components of the Genelute kit (Supelco; Bellafonte, Pa.) and cloned into pCR2.1 as described above. This clone was designated DV 125. The primer sequences were as follows:

NEO5' BAM-CGGGATCCATTGAACAAGATTGCAC
NEO3' SAC-GGGAGCTCTCAGAAGAACTCGTCAAGAAG

To create the desired fusion protein, DV 125 was cleaved with BamHI and SacI to separate the NPTII coding sequence from the remainder of the plasmid and the 802 bp fragment containing the NPTII coding sequence was purified by gel electrophoresis, band excision, and DNA elution by using the components of the Genelute kit (Supelco; Bellafonte, Pa.). DV123 and DV124 were cleaved with these same enzymes, creating complementary cloning sites that would join the GFP and NPTII coding sequences at the BamHI site. These ligations were performed using standard procedures and the clones obtained have been named DV127 (MGFP::NPTII in pCR2.1) and DV134 (EGFP::NPTII in pCR2.1).

These novel coding sequences were placed under the control of the embryo/aleurone specific mzL3 promoter in the following expression cassettes, which were prepared as described in Example 3:
pDPG778-L3/GUS/Tr7
pDPG779-L3/rACTI IntronI/GUS/Tr7

To construct DV130 (containing an L3/MGFP::NPTII/Tr7 expression cassette; SEQ ID NO:2), the MGFP::NPTII fusion was excised from DV127 with EcoRI and HindIII, purified by gel electrophoresis, band excision, and DNA elution by using the components of the Genelute kit (Supelco; Bellafonte, Pa.), and blunt ends were generated by using Klenow polymerase (Boehringer Mannheim, Indianapolis, Ind.) as described in Sambrook et al., (1989). This fragment was then cloned into pDPG778 which had been cleaved with restriction enzymes EcoRI and SmaI and blunt-ended in the same manner. Plasmid clones containing the desired orientation of the GFP::NPTII fragment were identified by cleavage with NcoI and NotI, which provides a diagnostic set of fragments of 197 bp, 891 bp, 1468 bp, and 3681 bp for those clones which contain the MGFP::NPTII sequence in the appropriate orientation relative to the promoter sequence.

To construct DV132 (containing an L3/rACTI IntronI/MGFP::NPTII/Tr7 expression cassette; SEQ ID NO:4), the MGFP:: NPTII fusion was excised from DV127 with EcoRI and HindIII, purified by gel electrophoresis, band excision, and DNA elution by using the components of the Genelute kit (Supelco; Bellafonte, Pa.) and blunt ends generated by using Klenow polymerase. This was then cloned into the backbone of plasmid pDPG779, which was obtained as follows: pDPG779 was cleaved with SmaI to release a GUS coding sequence from the plasmid backbone containing the L3 promoter and the Tr7 terminator. The backbone of 5047 bp plasmid was purified by gel electrophoresis, band excision, and DNA elution by using the components of the Genelute kit (Supelco; Bellafonte, Pa.) and ligated to the blunt-ended MGFP::NPTII fusion under standard conditions. Plasmid clones containing the desired orientation of the MGFP::NPTII fragment were identified by cleavage with NcoI and NotI, which provides a diagnostic set of fragments of 738 bp, 891 bp, 1468 bp, and 3681 bp for those clones which contain the MGFP::NPTII sequence in the appropriate orientation relative to the promoter sequence.

To construct DV131 (containing an L3/EGFP::NPTII/Tr7 expression cassette; SEQ ID NO:3), the EGFP:: NPTII fragment was excised from DV126 with EcoRI and HindIII and blunt ends generated by using Klenow polymerase. This was then cloned into the backbone of plasmid pDPG778, which was obtained as follows: pDPG778 was cleaved with EcoRI and SmaI to release the GUS coding sequence from the plasmid backbone containing the L3 promoter and the Tr7 terminator. The backbone of 4501 bp was purified by gel electrophoresis, band excision, and DNA elution by using the components of the Genelute kit (Supelco; Bellafonte, Pa.) and blunt ends generated by using Klenow polymerase. This backbone was ligated to the blunt-ended EGFP::NPTII fragment under standard conditions. Plasmid clones containing the desired orientation of the MGFP::NPTII fragment were identified by cleavage with NcoI and NotI, which provides a diagnostic set of fragments of 199 bp, 891 bp, 1282 bp, and 3682 bp for those clones which contain the MGFP::NPTII sequence in the appropriate orientation relative to the promoter sequence.

To construct DV133 (containing an L3/rACTI IntronI/ EGFP::NPTII/Tr7 expression cassette; SEQ ID NO:5), the EGFP:: NPTII fragment was excised from DV126 with EcoRI and HindIII and blunt ends generated by using Klenow polymerase. This was then cloned into the backbone of plasmid pDPG779 which was obtained as follows: pDPG779 was cleaved with SmaI to release the GUS coding sequence from the plasmid backbone containing the L3 promoter and the Tr7 terminator. The backbone of 5047 bp was purified by gel electrophoresis, band excision, and DNA elution by using the components of the Genelute kit (Supelco; Bellafonte, Pa.) and ligated to the blunt-ended EGFP::NPTII fusion under standard conditions. Plasmid clones containing the desired orientation of the EGFP::NP-TII fragment were identified by cleavage with NcoI and NotI, which provides a diagnostic set of fragments of 740 bp, 891 bp, 1282 bp, and 3682 bp for those clones which contain the EGFP::NPTII sequence in the appropriate orientation relative to the promoter sequence.

EXAMPLE 2

Isolation of the L3 Promoter

Plants from the inbred maize line Mo17 were propagated in the greenhouse and grown for several weeks for the isolation of genomic DNA. Genomic DNA was prepared from 2–3 week old leaf material according to the following protocol. Frozen leaf tissue (2 grams fresh weight) was ground into a fine powder with a glass rod under liquid nitrogen. Powdered tissue was mixed thoroughly with 8 ml of extraction buffer (100 mM Tris, pH 8.0; 50 mM EDTA; 1% v/v SDS; 500 mM NaCl), pre-warmed to 60° C., followed by a 45 minute incubation at 60° C. The sample was then mixed with 2.5 ml of ice-cold 5 M potassium acetate and then incubated on ice for 20 minutes. Protein aggregates were removed by centrifugation at 3750 rpm for 20 minutes. The supernatant was poured through a layer of Miracloth and the DNA was precipitated by mixing with 5 ml of isopropyl alcohol. Precipitated DNA was collected by centrifugation at 3750 rpm for 15 minutes. The supernatant was poured off of the pelleted DNA and the tube was inverted for 5 minutes to allow residual supernatant to drain from the pellet. DNA was resuspended in 300 µL of water containing 50 mM Tris, pH 8.0, 10 mM EDTA and 3 µL of RNase (10 mg/mL stock). The DNA was precipitated again by the mixing with 50 µL of 4.4 M ammonium acetate, pH 5.2, and 350 µL of isopropyl alcohol, followed by centrifugation in a microcentrifuge at 14,000 rpm for 10 minutes. The DNA pellet was washed with 750 µL of 80% v/v ethanol and then allowed to drain by inversion for 10 minutes. The DNA was resuspended in 200 µL of water containing 10 mM Tris, pH 8.0, and 1 mM EDTA.

The genomic DNA was used as a template for PCR reactions which utilized PCR primers derived from a maize oleosin sequence (L3 mRNA partial coding sequence.; Locus MZEMPL3; GenBank accession M17225). Oligo L3-TOP (SEQ ID NO:13) matches nucleotides 123–143 and L3-BOT (SEQ ID NO:14) matches the sequence complementary to nucleotides 407–427. The predicted PCR amplification product is 305 bp. The primer sequences were as follows:

L3-TOP CGGGTCGATGCTGGTGCTGTC
L3-BOT GGTCGATGCGGTGCTGTGCTG

The conditions for PCR amplification of the oleosin coding sequence were as follows:
20% v/v glycerol
1×PCR Buffer (Supplied with Taq Polymerase, Perkin-Elmer Corp., Foster City, Calif.)
1.5 mM MgCl2
0.2 mM dNTPs
0.5 mM each oligonucleotide
1 µL genomic DNAs (100 ng of Mo 17 genomic DNA)
6.5 units Taq polymerase (Perkin-Elmer Corp., Foster City, Calif.)

The thermocycling profile for amplification was:

| | | |
|---|---|---|
| 1. | 94° C. | 2 minutes |
| 2. | 94° C. | 1 minute |
| 3. | 62° C. | 1 minute |
| 4. | 72° C. | 1 minute |
| 5. | 36 cycles to step 2 | |
| 6. | 72° C. | 4 minutes |
| 7. | 4° C. | hold |

DNA bands of predicted sizes (approximately 300 bp) were purified by gel excision from a 2% w/v agarose gel and further purified using the Elu-Quick kit (Schelicher and Schuell, Keene, N.H.) according to manufacturer's instructions. Isolated DNA fragments were ligated into plasmid pDK101 (ATCC 77406) which had been cleaved with XcmI using the Boehringer-Mannheim (Indianapolis, Ind.) Rapid Ligation Kit, according to the manufacturer's instructions. The cloned oleosin coding sequence was sequenced by the double-stranded dideoxy termination method using the Sequenase Sequencing Kit (US Biochemicals), according to the manufacturer's instructions. DNA sequencing reactions were analyzed by standard protocols (Sambrook et al., 1989), utilizing gel electrophoresis, followed by detection of radioactive sequencing products by exposure to X-ray film.

Approximately 30 ng of amplified PCR product was labeled with $^{32}$P-dCTP using Pharmacia Random-Priming Kit (Pharmacia, Piscataway, N.J.), according to the manufacturer's instructions, and used to probe 30,000 genomic clones from a Mo17 genomic library (Stratagene, La Jolla, Calif.) on duplicate filters using standard protocols (Sambrook et al, 1989). Four clones were picked from the L3 screen. Individual clones were further purified by plating of 1:500 dilutions and subsequent screening. Four clones were purified to homogeneity, designated 28B, 29B, 32B, 35B.

Bacteriophage λ DNA was prepared from the 28B clone by the standard plate lysate method (Sambrook et al., 1989). DNA from clone 28B was restricted with NotI enzyme and subjected to Southern blot analysis using the 300 bp oleosin sequence prepared as described above. The digested genomic clone produced 11 and 5 kb fragments, and the 11 kb fragment hybridized with the 300 bp oleosin probe. Both NotI fragments were isolated and cloned into NotI digested pBSK (Stratagene, La Jolla, Calif.). These subclones were designated 28B 1–8 (11 kb insert) and 28B 2–3 (5 kb insert) and each was subjected to nucleotide sequence analysis as previously described. Clone 28B 1–8 contained the oleosin coding sequence and approximately 200 bp of 5' flanking sequence. Clone 28B 2–3 contained 5' sequence upstream of that present in clone 28B 1–8.

The 28B 1–8 clone was used as PCR template for amplification of promoter fragments. PCR primers L3-BOT(-1) (SEQ ID NO:15) and the vector localized KS primer (SEQ ID NO:16) were used to PCR amplify the region of the genomic clone which is approximately 200 bp upstream of the ATG start codon (PCR amplification conditions used as described previously). The PCR amplification yielded a 250 bp band, which was purified by gel excision and EluQuick and subsequently cloned by T/A cloning into pBSK (Stratagene, La Jolla, Calif.) which had been cleaved with EcoRV and treated with terminal nucleotide transferase and dideoxy dTTP (Promega, Madison, Wis.) to create T overhangs. The PCR product was cloned using the Rapid Ligation Kit (Boehringer Mannheim, Indianapolis, Ind.). A recombinant plasmid containing the insert was designated "t/aL3 1–3." By restriction digestion of t/aL3 1–3 with EcoRI and NotI (which cuts 165 bp upstrean of the ATG initiating codon), a 200 bp fragment was removed and sub-cloned into pcDNAII (Invitrogen) cleaved with EcoRI and NotI. This plasmid was named "pcDNAII/L3 3' 200 bp pro." The primer sequences were as follows:

```
L3-BOT(-1)      GGTAGGCTAGCAGAGCGAGCT
KS primer       TCGAGGTCGACGGTATC
```

The remainder of the L3 promoter region was isolated from the 5 kb sub-cloned fragment designated 28B 2–3. By restriction mapping, a 600 bp NotI/ClaI fragment was identified that would provide a contiguous promoter when combined with the 200 bp promoter region. This 600 bp fragment was cloned into pBSK (Stratagene, La Jolla, Calif.) cleaved with NotI and ClaI (clone pBSK/L3 5' 600 bp pro). To combine this fragment with "pcDNAII/L3 3' 200 bp pro", the 600 bp promoter fragment from "pBSK/L3 5' 600 bp pro" was removed using NotI and XhoI and then cloned into "pcDNAII/L3 3' 200 bp pro" cleaved with NotI and XhoI. A representative clone from this ligation containing the full 800 bp assembled promoter was designated "L3 pcDNAII contiguous."

To obtain additional sequence of the 5' promoter region, a sequencing primer was designed on the bottom strand of clone 28B 2–3 near the ClaI site (approximately 800 bp upstream of ATG) (L3 ClaIB; SEQ ID NO:17). An additional 300 bp of nucleotide sequence was obtained, which identified a unique ScaI site upstream. This ClaI/ScaI fragment was isolated from 28B 2–3 and sub-cloned into "L3 pcDNAII contiguous" cleaved with ClaI and HindII. A full length promoter was assembled when clone "L3 1050-4" was chosen from this ligation. The actual length of the final promoter sequence was 1039 bp. The L3 ClaIB sequence was:
L3 ClaIB TTGCTGAAGGTGAGATGC

EXAMPLE 3

Preparation of L3/GUS Constructs

The preparation of the vector pDPG778 first involved construction of pDPG684, which contains a multiple cloning site immediately upstream of the GUS coding sequence. pDPG684 was constructed as follows: pDPG126 (35S/GUS/Tr7) was cleaved with EcoRI and BamHI in order to isolate a 2370 bp fragment containing the GUS coding sequence and Tr7 terminator. A fragment of the expected size was observed in agarose gel electrophoresis, and this was excised from the gel and purified using the Elu-Quik Kit (Schleicher and Schuell, Keene, N.H.). The cohesive ends of this fragment were then filled in using Klenow enzyme (DNA polymerase I, Boehringer Mannheim, Indianapolis, Ind). The vector pBSK(-) (Stratagene, LaJolla, Calif.) was cleaved with SalI and the cohesive ends filled in the same manner followed by treatment with alkaline phosphatase to prevent self ligation. These two fragments were then ligated using the Rapid Ligation Kit (Boehringer Mannheim, Indianapolis, Ind.) and clones were selected by cleavage with EcoRV, which provides a diagnostic set of fragments of 231, 604, 1308 and 3257 bp. This clone was designated pDPG684.

The L3 promoter (1039 bp) was excised from clone "L3 1050-4," prepared as described in Example 2, by cleavage with XbaI and EcoRI, and the expected 1064 bp band was purified by gel electrophoresis, band excision, and DNA elution by using the components of the Genelute system (Supelco, Bellafonte, Pa.). The plasmid pDPG684 (polylinker/GUS/Tr7) was also cleaved with XbaI and EcoRI and the 5370 bp backbone was purified by the same method. The 1039 bp L3 promoter fragment were inserted into the cleaved pDPG684 backbone in a ligation reaction using the Rapid Ligation Kit (Boehringer Mannheim, Indianapolis, Ind.). A single clone was selected and designated pDPG778.

For construction of the plasmid vector pDPG779, pDPG778 DNA was cleaved with EcoRI and treated with alkaline phosphatase to prevent self ligation. The rice ActinI IntronI sequence was amplified in a PCR in which pDM302 (Plant Cell Reports 11:586–591, 1992) was used as a template and oligonucleotides pRACT 5I (SEQ ID NO: 18) and rACT 31 (SEQ ID NO:19) as primers; these primers also served to add EcoRI ends to the amplification product. Each primer containing an EcoRI tail for cloning.
rACT 5I-GGAATTCGGTAACCACCCCGCCCCTCT
rACT 3I-GGAATTCTACCTACAAAAAAGCTCCG
PCR amplification of the rice ActinI IntronI sequence from pDM302 was performed as follows:
HF PCR Kit (Boehringer Mannheim, Indianapolis, Ind.)
500 nM each primer
200 uM dNTP's
100 pg template (pDM302; Plant Cell Reports (1992) 11:586–591)
3 mM MgCl
Cycling

| MJ Research PTC-100 | | |
|---|---|---|
| 95° | 2 min. | 1 cycle |
| 94° | 45 sec. | |
| 56° | 45 sec. | |
| 72° | 45 sec. | 32 cycles |
| 72° | 4 min. | 1 cycle |
| 4° | hold | |

The expected 472 bp fragment was purified by gel electrophoresis, band excision, and DNA elution by using the components of the Genelute system (Supelco, Bellafonte, Pa.). This product was then cleaved with EcoRI and ligated into the EcoRI site of pDPG778 by using the Rapid Ligation Kit (Boehringer Mannheim, Indianapolis, Ind.). A clone was selected by cleaving with BamHI and KpnI, which provides a diagnostic of fragments of 16, 333, 563, 717, 1921 and 3391 bp. This clone was designated pDPG779.

EXAMPLE 4

Bacterial Expression of GFP:NPTII Constructs

Figure 6:
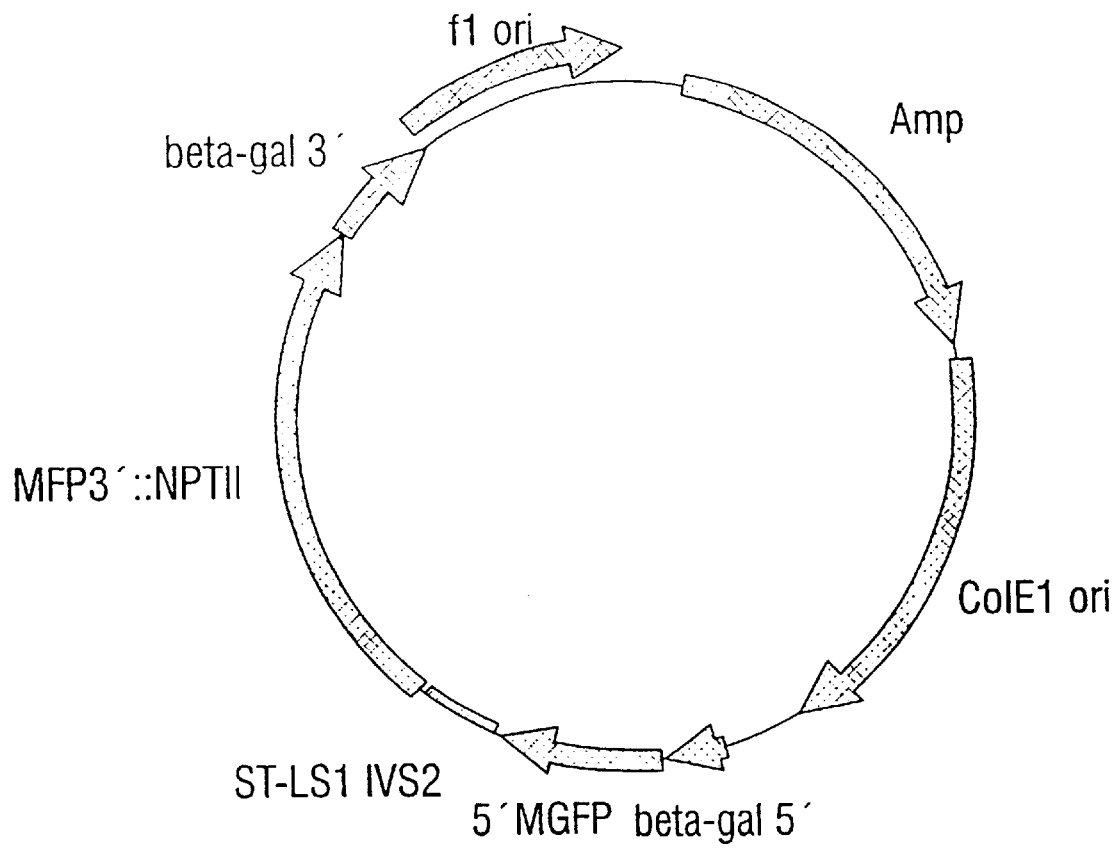
FIG. 6: Map of plasmid PBSK/MGFP/NPTII. The 4690 bp plasmid construct contains the coding sequence of a MGFP::NPTII translational fusion inserted in-frame into the beta-galactosidase protein coding sequence in the pBSK plasmid.

The plasmid DV127 (SEQ ID NO:1), prepared as described in Example 1, was cleaved with EcoRV and HindIII to release a fragment of 1736 bp containing the MGFP::NPTII sequence. The fragment was isolated by gel electrophoresis, band excision, and DNA elution by using the components of the Genelute kit (Supelco; Bellafonte, Pa.) according to the manufacturers directions. This fragment was inserted into the plasmid pBSK (Stratagene, La Jolla, Calif.) which had been cleaved with EcoRV and HindIII using the components of the Rapid Ligation Kit (Boehringer Mannheim, Indianapolis, Ind.). This placed the MGFP::NPTII fusion protein in frame with the beta-galactosidase coding sequence resident in the pBSK plasmid under the control of the E. coli lac-i promoter. This plasmid was designated pBSK/MGFP::NPTII (FIG. 6).

Figure 5:
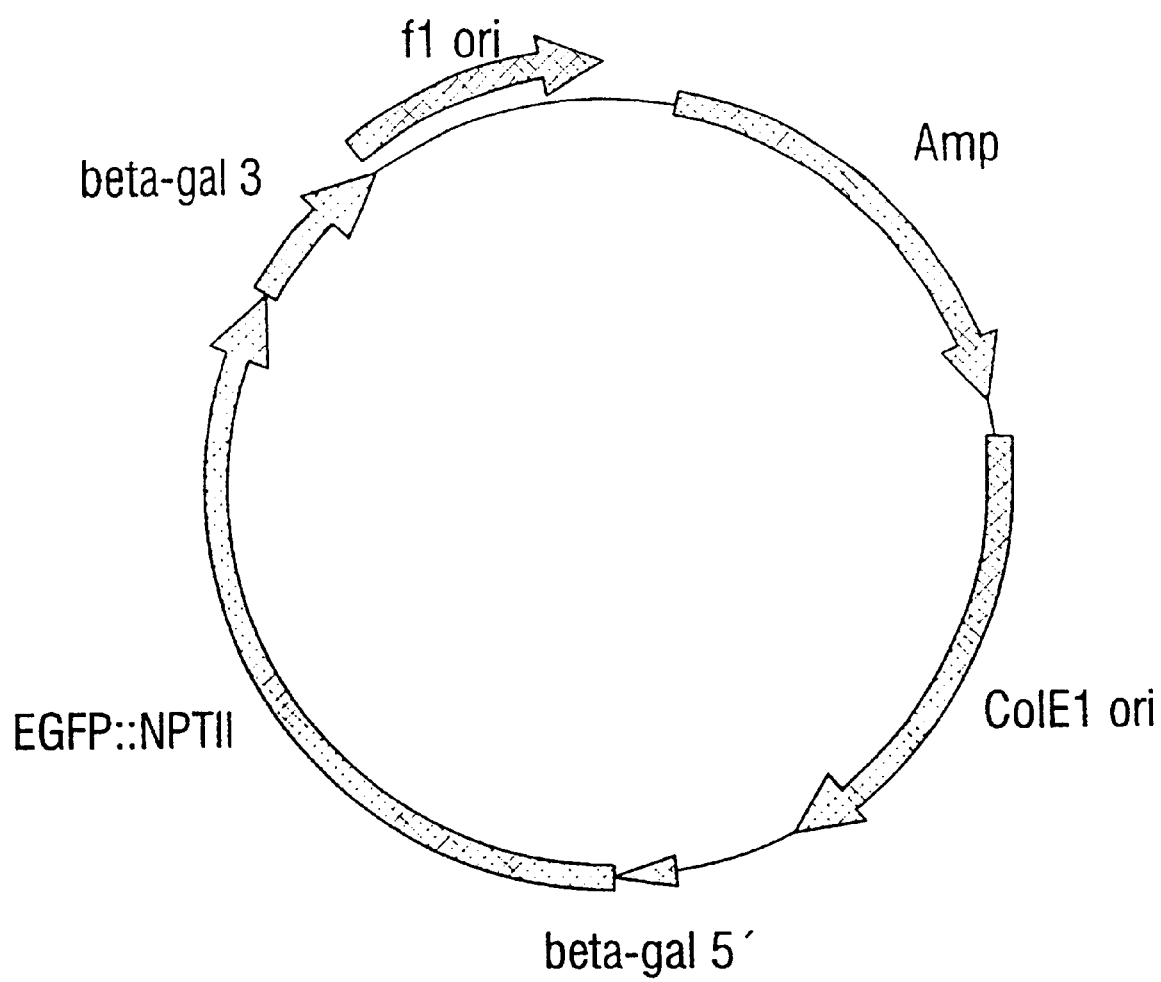
FIG. 5: Map of plasmid PBSK/EGFP/NPTII. The 4530 bp plasmid contains the coding sequence of a EGFP::NPTII translational fusion inserted in-frame into the beta-galactosidase protein coding sequence in the pBSK plasmid.

Similarly, pDPG899 (DV134; SEQ ID NO:6) was cleaved with NotI and HindIII to release a 1621 bp fragment containing the EGFP::NPTII. This fragment was isolated by gel electrophoresis, band excision, and DNA elution using the Genelute kit (Supelco; Bellafonte, Pa.). This fragment was inserted into the plasmid pBSK (Stratagene, La Jolla, Calif.), which had been cleaved with NotI and HindIII by using the components of the Rapid Ligation Kit (Boehringer Mannheim, Indianapolis, Ind.). This placed the EGFP::NPTII fusion protein in frame with the beta-galactosidase coding sequence resident in the pBSK plasmid under control of the E. coli lac-i promoter. This plasmid was designated pBSK/EGFP::NPTII (FIG. 5).

DH5α cells (Gibco Life Sciences, Bethesda, Md.) were transformed with either pBSK/MGFP::NPTII or pBSK/EGFP::NPTII, as recommended by the manufacturer, with the addition of IPTG to 1 mM in the liquid LB growth medium. Cells were plated out on LB-agar (Gibco Life Sciences) containing 0.0008% X-gal and 0.2 mM IPTG and supplemented with either kanamycin (50 µg/ml) or ampicillin (100 µg/ml). Colonies were observed on both kanamycin and ampicillin media from the transformation involving pBSK/EGFP::NPTII, indicating the presence of NPTII activity as determined by resistance of the colonies to kanamycin. Colonies resulting from transformation with pBSK/MGFP::NPTII were observed only on ampicillin media, and not on kanamycin media. The growth of colonies on ampicillin media in both transformation experiments was the result of expression of the beta-lactamase gene resident in pBSK; the absence of colonies on kanamycin media in the pBSK/MGFP::NPTII transformation experiment was likely due to the fact that the MGFP sequence contains the potato ST-LS1 intron which is not removed from the NGFP::NPTII transcript in the E. coli host. Analysis of pBSK/EGFP::NPTII colonies using fluorescent microscopy allowed for detection of fluorescence of GFP, indicating the presence of both nptII and GFP activity in these cells.

EXAMPLE 5

Transformation of Hi x AW Immature Embryos and 716 Suspensions With GFP Fusion Gene Constructs Immature embryos (Hi X AW) and 716 suspension were used to study transient expression of vectors comprising selectable-screenable marker gene fusions. The makeup of the vectors used is listed below, in Table 9, and given in FIGS. 1–4, and the components included in the vectors are given in Table 10. Two plates of each tissue were used for each of the vectors. A 35S-GFP vector was used as a control (pDPG720). Approximately 0.5 µg of plasmid DNA was used for each plate (2.0 µg/tube). Microprojectile bombardment was carried out as described in Example 7. Bombarded tissue was observed with a Zeiss Axiophot microscope. Fluorescence was supplied by a mercury light source and a filter set comprising a BP450–490 exciter filter, a FT510 chromatic beam splitter, and a BP515–565 barrier filter (Carl Zeiss, Inc., Thornwood, N.Y.). GFP expression was observed for each of the vectors. Table 11 shows a visual estimate of GFP expression 48 h post-bombardment. It was noted that the L3 promoter seemed to express better in the embryos than in suspension cells. Also, the Actin intron appeared to boost expression in the suspension cells, whereas expression in the embryos was high regardless of the presence of the intron.

TABLE 9

Vectors Tested by Transient Assay

| Plasmid number | GFP Expression Cassette |
| --- | --- |
| pDPG720 | 35S-GFP-TYG-nos |
| pDV130 | L3/MGFP::NPTII/Tr7 |
| pDV131 | L3/EGFP::NPTII/Tr7 |
| pDV132 | L3/rACT/MGFP::NPTII/Tr7 |
| pDV133 | L3/rACT/EDFP::NPTII/Tr7 |

TABLE 10

Components of GFP Fusion gene Constructs

| Gene Element | Description | Reference | GenBank Accession |
| --- | --- | --- | --- |
| L3 promoter | promoter from maize ole 16 gene | Lee and Huang, Plant Mol. Biol., 26:1981–1987, 1994 | U13701 |
| MGFP | enhanced GFP sequence | Pang et al., Plant Physiology, 112:893–900, 1996 | |
| EGFP | enhanced GFP sequence (Clontech cat #6077-1) | Yang et al., Nucleic Acids Res., 24:4592–4593, 1996 | U76561 |
| GFP-TYG | enhanced GFP sequence | Chiu et al., Curr. Biol., 1996 6:325–330, 1996 | |
| rACT | rice actin1 intron1 | McElroy et al., Plant Cell, 2:163–171, 1990 | |
| Tr7 | Agrobactertium tumefaciens transcript 7 3' untranslated region. | Dhaese et al., EMBO J., 2:419–426, 1983 | |

TABLE 11

Visual Estimate of GFP Expression in (1X6) 716 Suspension Cells and (AWXCW) Immature Embryos at 48 H Post-Bombardment

| GFP Vector | Expression in 716 Suspension | Expression in AWX HiII Immature Embryos |
| --- | --- | --- |
| 35S-GFP | +++ | +++ |
| L3/MGFP::NPTII/Tr7 | ++ | ++++ |
| L3/EGFP::NPTII/Tr7 | ++ | ++++ |
| L3/rACT/MGFP::NPTII/Tr7 | ++++ | ++++ |
| L3/rACT/EGFP::NPTII/Tr7 | ++++ | ++++ |

EXAMPLE 6

Initiation of the Suspension Culture G(A188XB73) 716 (designated 716) for Use in Transformation The maize suspension culture designated 716, which was employed by the instant inventors for transformation studies with selectable-screenable marker gene fusions, was prepared as follows. Type II tissue used to initiate the cell suspension was initiated from immature embryos of A188× B73 plated onto N6-based medium with 1 mg/ml 2,4-D (201; see Table 8). A Type II callus was initiated by visual selection of fast growing, friable embryogenic cells. The suspension was initiated within 6 months after callus initiation. Tissue chosen from the callus to initiate the suspension consisted of undifferentiated Type II callus. The characteristics of this undifferentiated tissue include the earliest stages of embryo development and soft, friable, undifferentiated tissue underlying it.

Approximately one gram of tissue was added to 20 ml of liquid medium. In this example, the liquid medium was medium 402 to which different slow-release growth regulator capsule treatments were added (U.S. Pat. No. 5,550,318). These capsule treatments included 2,4-D, NAA, 2,4-D plus NAA, and two NAA capsules. One flask was initiated for each of the different 402 media plus growth regulator combinations. Every 7 days each culture was subcultured into fresh medium by transferring a small portion of the cellular suspension to a new flask. This involved swirling the original flask to suspend the cells (which tend to settle to the bottom of the culture vessel), tilting the flask on its side and allowing the denser cells and cell aggregates to settle slightly. One ml of packed cells was then drawn off from this pool of settled cells together with 4 ml of conditioned medium and added to a flask containing 20 ml fresh medium. A sterile ten ml, wide tip, pipet was used for this transfer (Falcon 7304). Any very large aggregates of cells which would not pass easily through the pipet tip were excluded. If a growth regulator capsule was present, it was also transferred to the new flask.

After approximately 7 weeks, the loose embryogenic cell aggregates began to predominate and fragment in each of the cultures, reached a state referred to as "dispersed." The treatment which yielded the highest proportion of embryogenic clusters was the 402 medium plus one NAA capsule. After the cultures became dispersed and were doubling approximately every two to three days as determined by increase in packed cell volume, a one ml packed cell volume inoculum from each culture was transferred into 20 ml 401 medium using a ten ml narrow tip pipet (Falcon 7551). These transfers were performed about every 3½ days. An inoculum from the 402 plus 2,4-D plus NAA capsules culture was also used to initiate a culture in 409 medium (402 without 2,4-D and including 10 mg/l dicamba) either with or without 1 ml coconut water (Gibco 670–8130AG) per 25 ml culture medium. The most dispersed cultures were cryopreserved after 2 weeks, 2 months or 5 months.

The culture grown on 409 with coconut water was thawed approximately 3.5 years after cryopreservation, cultured for two weeks on solid 201 (except containing 0.5 mg/kg 2,4-D, 2% manitol, and 3% sucrose) culture medium using BMS as a feeder layer (Rhodes et al., 1988) and transferred to media 409 without coconut water. The culture was maintained by subculturing once or twice weekly in 409 or 401 medium by the method described above.

EXAMPLE 7

Microprojectile Bombardment Transformation of Immature Embryos and Suspension Cultures SC716 suspension culture cells were plated onto Whatman #4 paper filters (7 cm) using a Bucher funnel. Filters with suspension culture cells (approximately 0.5 ml PCU/filter) were transferred to 735 medium containing 12% sucrose prior to bombardment. Alternatively, immature embryos (1.2–3.0 mm in length) were excised from surface-sterilized, greenhouse-grown ears of Hi-II 10–12 days post-pollination. The Hi-II genotype was developed from an A188×B73 cross (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2(N-morpholino) ethanesulfonic acid (MES), 0.75 g/l $MgCl_2$, and 2% sucrose solidified with 2 g/l Gelgro, pH 5.8 (#735 medium). Embryos were cultured in the dark for two to four days at 24° C.

Approximately 3–4 hours prior to bombardment, embryos were transferred to the above culture medium with the sucrose concentration increased from 3% to 12%. When embryos were transferred to the high osmoticum medium they were arranged in concentric circles on the plate, starting 1 cm from the center of the dish, positioned such that their coleorhizal end was oriented toward the center of the dish. Usually two concentric circles were formed with 25–35 embryos per plate.

Microprojectiles were prepared for transformation by adding 60 mg of 0.6 µm gold microprojectiles (BioRad, cat. no. 165–2262) to 1000 µl absolute ethanol and incubating for at least 3 hours at room temperature followed by storage at –20° C. Twenty to thirty five µl of the sterile gold particles and more preferably 30 to 35 µl of gold particles (30 µl contains 1.8 mg of particles) was then centrifuged in a microcentrifuge for up to 1 min. The supernatant was removed and one ml sterile water was added to the tube, followed by centrifugation at 1800–2000 rpm for 2–5 minutes. Microprojectile particles were resuspended in 25–30 µl of DNA solution containing approximately 1–1000 µg per each 1.8 mg of particles.

Two hundred twenty microliters sterile water, 250 µl 2.5 M $CaCl_2$ and 50 µl stock spermidine (14 µl spermidine in 986 µl water ) we re then added to t he particle containing solution. The solution was thoroughly mixed and placed on ice, followed by vortexing at 4° C. for 10 minutes and centrifugation at 500 rpm for 5 minutes. The supernatant was removed and the pellet resuspended in 600 µl absolute ethanol. Following centrifugation at 500 rpm for 5 minutes, the pellet was resuspended in 36–38 µl of absolute ethanol, vortexed for approximately 20 seconds, and sonicated for 20–30 seconds. At this stage the particles were allowed to sit for 2–5 minutes, after which 5–10 µl of the supernatant was removed and dispensed on the surface of a flyer disk and the ethanol allowed to dry completely. Alternatively, particles may be removed directly after resuspension and vortexing 20 to 30 seconds in 36 µl–38 µl of ethanol, placed on the flyer disk and allowed to dry as done for the settled treatment.

The particles were then used for bombardment of the embryos or SC716 suspension cultures by a helium blast of approximately 1100 psi using the DuPont Biolistics PDS1000He particle bombardment device. The plates containing embryos were placed on the third shelf from the bottom, 5 cm below the stopping screen. Each plate was bombarded once with the DuPont Biolistics PDS1000He particle gun. Cells and embryos were bombarded and incubated in the dark at approximately 27° C. GFP was visualized about 48 hours post bombardment.

EXAMPLE 8

Screenable Marker Assay and Photography

For GFP analysis, seeds were exposed to ultraviolet light and visually scored. Alternatively, if fluorescence is faint, scoring may be enhanced utilization of devices that enhance night vision, or by a highly light sensitive video camera, such as a photon counting camera. Detection will be enhanced by the utilization of specialized filters for excitation and detection of fluorescence. In the instant case, transgenic tissue was observed with a Zeiss Axiophot microscope. Fluorescence was supplied by a mercury light source and appropriate filter set (an exciter filter (BP450–490), a chromatic beam splitter (FT510), and a barrier filter (BP515–565) (Carl Zeiss, Inc., Thornwood, N.Y.).

For the luciferase analysis of seeds, seeds are immersed into a petri dish containing 150 $\mu$l of 1 mM potassium luciferin (Analytical Luminescence Laboratories, La Jolla, Calif.) in 67 mM sodium Mes, pH 5.4. For observation, a starlight scope with relay lens (for example, a light amplifier NVS100; OpticElectronic, Dallas) and a highly sensitive video camera are used, e.g., a photon counting camera (Hamanatsu Corp., Bridgewater, N.J.)). Preferably observations are made about 20 min after administration of luciferin. The presence of the R-gene screenable marker can be scored by the color of the seed, with transformed seeds exhibiting a red color.

EXAMPLE 9

Transformation of H99 Immature Embryos or Callus and Selection with Paromomycin

Maize immature embryos (1.2–3.0 mm, 10–14 days post pollination) are isolated from greenhouse grown H99 plants that have been self or sib pollinated. Immature embryos are cultured on 735 medium in the dark at approximately 27° C. Immature embryos are either bombarded 1–6 days after isolation or cultured to produce embryogenic callus that is used for bombardment. Embryogenic callus is expanded and maintained by subculturing at 2–3 week intervals to fresh 735 medium. Prior to bombardment, cultured embryos or embryogenic callus (subdivided in approximately 2–4 mm clumps) are transferred to 735 medium containing 12% sucrose for 3–6 hours. Following bombardment, carried out as described in Example 7, tissue cultures are incubated overnight and transferred to 735 medium containing 500 mg/L paromomycin. After 2–3 weeks, callus is subdivided into small pieces (approximately 2–4 mm in diameter) and transferred to fresh selection medium. This subculture step is repeated at 2–3 week intervals for up to about 15 week post-bombardment, with subdivision and visual selection for healthy, growing callus.

Paromomycin tolerant callus is transferred to 735 medium without 2,4-D but containing 3.52 mg/L BAP for 3–9 days in the dark at approximately 27° C. and is subsequently transferred to 110 medium (½×MS salts, 0.5 mg/L thiamine, 0.5 mg/L nicotinic acid, 3% sucrose, 3.6 g/L Gelgro, pH 5.8) containing 100 mg/L paromomycin in Phytatrays (Sigma) and cultured at about 27° C. in the light. Plantlets that develop in Phytatrays after 3–6 weeks are then transferred to soil. Plantlets are acclimated in a growth chamber and grown to maturity in the greenhouse.

EXAMPLE 10

General Methods for Microprojectile Bombardment

Many variations in techniques for microprojectile bombardment are well known in the art and therefore deemed useful with the current invention. Exemplary procedures for bombardment are discussed in, for example, U.S. Ser. No. 08/113,561, filed Aug. 25, 1993. Examples of target tissues which may be used with the current invention include immature embryos, Type I callus, Type II callus, Type III callus, suspension cultures and meristematic tissue (PCT Publication WO 96/04392). Some genotypes which are especially useful for maize transformation are disclosed in, for example, U.S. Ser. No. 08/113,561, filed Aug. 25, 1993. Preferred genotypes will be those which are readily transformable and which also may be regenerated to yield a fertile transgenic plant.

Any method for acceleration of microprojectiles may potentially be used to transform a plant cell with the current invention. A preferred method will be a gas-driven particle gun such as the DuPont Biolistics PDS1000He particle bombardment device. Exemplary particles for bombardment include those comprised of tungsten, gold, platinum, and the like. Gold particles are deemed particularly useful in the current invention, with 0.6 $\mu$m or 0.7 $\mu$m gold particles being preferred and 0.6 $\mu$m particles most preferred. The most preferred particles will be DNA coated and have a mean size between 0.6 $\mu$m and 1.0 $\mu$m.

As disclosed herein, any DNA sequence may potentially be used for transformation. The DNA segments used for transformation will include a selectable and/or screenable marker construct in accordance with the current invention. Many examples of selectable and screenable marker genes which may be used with constructs prepared in accordance with the invention are specifically disclosed herein. In the case of selectable markers, selection may be carried out in solid or liquid media. The DNA constructs of the invention will preferably also include one or more genes which confer, either individually or in combination with other sequences, a desired phenotype on the transformed plant. Exemplary genes for transformation and the corresponding phenotypes these sequences may confer on the transformed plant are disclosed herein.

EXAMPLE 11

Plant Breeding Protocols Using Seed-Expressed Screenable Markers

The constructs of the instant invention will be especially useful in plant breeding programs. In particular, the invention facilitates the advancement of transgene constructs into subsequent generations by allowing direct screening of transgenic seeds at each generation. An example of a breeding protocol for which the invention can be applied is backcrossing. Backcrossing may be used to transfer a selected trait to a plant originally lacking the trait. In the case of the current invention, the selected trait is comprised on a transgene which includes a screenable marker, or is genetically linked thereto. The advantage of the instant invention is that the presence of this transgene can be ascertained directly in viable seeds without the need for destructive assays or growing of the seed. In particular, transgenic seeds can be identified based on the expression of a screenable marker.

Therefore, plants comprising the constructs of the current invention may be entered into breeding protocols which utilize the transgenic seed screening capabilities provided by these constructs. For example, in a conventional breeding protocol, a superior inbred (A) (recurrent parent) is crossed to a donor inbred (non-recurrent parent), which carries the appropriate gene(s) for the trait in question. The progeny of this cross are then selected which comprise the desired trait to be transferred from the non-recurrent parent, then the selected progeny are mated back to the superior recurrent parent (A). This process requires the time and labor intensive steps of growing of the progeny seeds and assaying the resultant plants for the desired trait at each generation. However, the instant invention allows the step of selecting a trait which is genetically linked to a screenable marker based on the phenotype of the seed, saving significant time and effort. The gene controlling a trait being advanced in the breeding protocol may be genetically linked to the screenable marker as a result of being introduced into the host genome on a single segment of DNA which includes the screenable marker or selectable-screenable marker gene fusion, thereby forming a single transformation event in the host genome, or the gene or trait could be native to a chromosomal region which is in close proximity to the site of integration of the transgenic marker gene or marker gene fusion. The marker gene could also be introduced by co-transformation or multiple transformations, thereby leading to the production of multiple transformation events located in close genomic proximity.

A backcrossing protocol such as that described above typically proceeds five or more generations with selection for the desired trait at each generation, after which the progeny are hemizygous for loci controlling the characteristic being transferred, but are like the superior parent for most or almost all other genes. The last backcross generation are typically selfed to give progeny which are pure breeding for the gene(s) being transferred, i.e. one or more transformation events. With the instant invention, however, the last step is not required, as seeds could be selected from a set of heterozygous parents by identification of the screenable marker phenotype.

Therefore, through a series a breeding manipulations, a selected transgene may moved from one line into an entirely different line without the need for further recombinant manipulation. Transgenes are valuable in that they typically behave genetically as any other gene and can be manipulated by breeding techniques in a manner identical to any other corn gene. Therefore, one may produce inbreds plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

EXAMPLE 12

General Methods for Assays

DNA analysis of transformed plants is performed as follows. Genomic DNA is isolated using a procedure modified from Shure, et al., 1983. Approximately 1 gm callus or leaf tissue is ground to a fine powder in liquid nitrogen using a mortar and pestle. Powdered tissue is mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate is extracted with 4 ml phenol/chloroform. The aqueous phase is separated by centrifugation, passed through Miracloth, and precipitated twice using 1/10 volume of 4.4 M ammonium acetate, pH 5.2 and an equal volume of isopropanol. The precipitate is washed with 70% ethanol and resuspended in 200–500 $\mu$l TE (0.01 M Tris-HCl, 0.001 M EDTA, pH 8.0).

The presence of a DNA sequence in a transformed cell may be detected through the use of polymerase chain reaction (PCR). Using this technique specific fragments of DNA can be amplified and detected following agarose gel electrophoresis. For example, two hundred to 1000 ng genomic DNA is added to a reaction mix containing 10 mM Tris-HCl pH 8.3, 1.5 mM $MgCl_2$, 50 mM KCl, 0.1 mg/ml gelatin, 200 $\mu$M each dATP, dCTP, dGTP, dTTP, 0.5 $\mu$M each forward and reverse DNA primers, 20% glycerol, and 2.5 units Taq DNA polymerase. The reaction is run in a thermal cycling machine as follows: 3 minutes at 94 C., 39 repeats of the cycle 1 minute at 94 C., 1 minute at 50 C., 30 seconds at 72 C., followed by 5 minutes at 72 C. Twenty $\mu$l of each reaction mix is run on a 3.5% NuSieve gel in TBE buffer (90 mM Tris-borate, 2 mM EDTA) at 50V for two to four hours.

For Southern blot analysis, genomic DNA is digested with a 3-fold excess of restriction enzymes, electrophoresed through 0.8% agarose (FMC), and transferred (Southern, 1975) to Nytran (Schleicher and Schuell) using 10×SCP (20×SCP: 2 M NaCl, 0.6 M disodium phosphate, 0.02 M disodium EDTA). Filters are prehybridized at 65° C. in 6×SCP, 10% dextran sulfate, 2% sarcosine, and 500 $\mu$g/ml heparin (Chomet et al., 1987) for 15 min. Filters then are hybridized overnight at 65 C. in 6×SCP containing 100 $\mu$g/ml denatured salmon sperm DNA and $^{32}$P-labeled probe. Filters are washed in 2×SCP, 1% SDS at 65 C. for 30 min. and visualized by autoradiography using Kodak XAR5 film. For rehybridization, the filters are boiled for 10 min. in distilled $H_2O$ to remove the first probe and then prehybridized as described above.

EXAMPLE 13

Utilization of Transgenic Crops

The ultimate goal in plant transformation is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. Such products may be made from particular plant parts or from the entire plant. One product made from the entire plant, which is deemed of particular value, is silage for animal feed.

Means for preparing products from plants, such as those that may be made with the current invention, have been well known since the dawn of agriculture and will be known to those of skill in the art. Specific methods for crop utilization may be found in, for example, Sprague and Dudley (1988), and Watson and Ramstad (1987).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Abdullah et al., *Biotechnology*, 4:1087, 1986.
Abel, Nelson, De, Hoffmann, Rogers, Fraley, Beachy, *Science*, 232:738–743, 1986.
Armaleo et al., *Current Genetics*, 17:97–103, 1990.
Armstrong et al., *Maize Genetics Coop Newsletter*, 65:92–93, 1991.
Barkai-Golan et al., *Arch. Microbiol*, 116:119–124, 1978.
Barnes, "Variable patterns of expression of luciferase in transgenic tobacco leaves," *Proc. Natl. Acad. Sci. USA*, 87:9183–9187, 1990.
Barton et al., *Plant Physiol.*, 85, 1103–1109, 1987.
Beck, Ludwig, Anerswald, Reiss, Schaller, "Nucleotide sequence and exact localization of the neomycin phosphotransferase gene from transposon Tn5," *Gene*, 9:327–336, 1982.
Bernal-Lugo and Leopold, *Plant Physiol.*, 98:1207–1210, 1992.
Bevan et al., *Nucleic Acid Research*, 11:369–385, 1983.
Blackman et al., *Plant Physiol.*, 100:225–230, 1992.
Bol et al., *Annu. Rev. Phytopath.*, 28:113–138, 1990.
Bouchez et al., *EMBO Journal*, 8(13):4197–4204, 1989.
Bowler et al., *Ann Rev. Plant Physiol.*, 43:83–116, 1992.
Branson and Guss, *Proceedings North Central Branch Entomological Society of America*, 27:91–95, 1972.
Broakaert et al., *Science*, 245:1100–1102, 1989.
Bryan et al., "Antimicrobial drug resistance," Bryan, L. E., ed., Academic Press, New York, 1984.
Buchanan-Wollaston et al., *Plant Cell Reports*, 11:627–631, 1992.
Callis et al., *Genes and Development*, 1:1183, 1987.
Campbell, W. C., ed. Avermectin and Abamectin. 1989.
Cashmore et al., *Gen. Eng. of Plants*, Plenum Press, New York, 29–38, 1983.
Chalfie, Tu, Euskirchen, Ward, Prasher, "Green fluorescent protein as a marker for gene expression," *Science*, 263:725–888, 1994a.
Chandler et al., *The Plant Cell*, 1:1175–1183, 1989.
Chau et al., *Science*, 244:174–181, 1989.
Chiu, Niwa, Zeng, Hirano, Kobayashi, Sheen, "Engineered GFP as a vital reporter in plants," *Curr. Biol.*, 6:325–330, 1996.
Chu et al., *Scientia Sinica*, 18:659–668, 1975.
Cody, Prasher, Westler, Prendergast, Ward, "Chemical structure of the hexapeptide chromophore of the Aequorea green fluorescent protein," *Biochemistry*, 32:1212–1218, 1993.
Conkling et al., *Plant Physiol.*, 93:1203–1211, 1990.
Cormack, Valdivia, Falkow, "FACS optimized mutants of the green fluorescent protein (GFP)," *Gene*, 173:33–38, 1996.
Coxson et al., *Biotropica*, 24: 121–133, 1992.
Cuozzo et al., *Bio/Technology*, 6:549–553, 1988.
Cutler et al., *J Plant Physiol*, 135:351–354, 1989.
Czapla and Lang, *J. Econ. Entomol.*, 83:2480–2485, 1990.
Davies et al., *Plant Physiol.*, 93:588–595, 1990.
De Block et al., *EMBO J.*, 6:2513–2518, 1987.
De Block et al., *Plant Physiol*, 91:694–701, 1989.
Delagrave, Hawtin, Silva, Yang, "Red-shifted excitation mutants of the green fluorescent protein," *Bio/Technology*, 13:151–154, 1995.
Dellaporta et al., "In Chromosome Structure and Function: Impact of New Concepts, 18th Stadler Genetics Symposium", 263–282, 1988.
Depicker et al., *Plant Cell Reports*, 7:63–66, 1988.
Dhaese, DeGreve, Gielen, Seurinck, Van Montagus, Schell, "Identification of sequences involved in polyadenylation of higher plant nuclear transcripts using Agrobacterium T-DNA genes as models," *EMBO J.*, 2:419–426, 1983.
Dure et al., *Plant Mol. Biol.*, 12:475–486, 1989.
Ebert et al., *Proc. Natl. Acad. Sci., USA*, 84:5745–5749, 1987.
Ellis et al., *EMBO Journal*, 6(11):3203–3208, 1987.
Erdmann et aL, *J. Gen. Microbiology*, 138:363–368, 1992.
Finkle et al., *Plant Sci.*, 42:133–140, 1985.
Fitzpatrick, *Gen. Engineering News* 22: (March 7): 7, 1993.
Fodor et al., Light-directed, spatially addressable parallel chemical synthesis. *Science*, 251:767–773, 1991.
Fransz et al., *Plant Cell Rep.*, 8:67–70, 1989.
Freifelder, *Physical Biochemistry Applications to Biochemistry and Molecular Biology*, 2nd ed. Wm. Freeman and Co., New York, N.Y., 1982.
Frohman, In: PCR Protocols: *A Guide To Methods And Applications*, Academic Press, N.Y., 1990.
Fromm M. E., Taylor L. P., Walbot V. (1986). *Nature* 312:791–793.
Fromm et al., *The Plant Cell*, 1:977–984, 1989.
Fujimura et al., *Plant Tissue Culture Letters*, 2:74, 1985.
Gallie et al., *The Plant Cell*, 1:301–311, 1989.
Gatehouse et al., *J. Sci. Food Agric.*, 35:373–380, 1984.
Goring et al., *Proc. Natl. Acad. Sci., USA*, 88:1770–1774, 1991.
Guerrero et al., *Plant Molecular Biology*, 15: 11–26, 1990.
Gupta et al., *Proc. Natl. Acad. Sci., USA*, 90:1629–1633, 1993.
Hacia et al., Detection of heterozygous mutations in BRCA1 using high density oligonucleotide arrays and two-colour fluorescence analysis. *Nature Genetics*, 14:441–447, 1996.
Hamilton et al., *Proc. Nat. Acad. Sci., USA*, 93(18) :9975–9979, 1996.
Hammock et al., *Nature*, 344:458–461, 1990.
Haseloff and Amos, "GFP in plants," *Trends Genet.*, 11:328–329, 1995.
Haseloff, Siemering, Prasher, Hodge, "Removal of a cryptic intron and subcellular localization of green fluorescent protein are required to mark transgenic Arabidopsis plants brightly," *Proc. Natl. Acad. Sci., USA*, 94:2122–2127, 1997.
Heim and Tsien, "Engineering green fluorescent protein for improved brightness, longer wavelengths and fluorescence resonance energy transfer," *Curr. Biol.*, 6:178–182, 1996.
Heim, Cubitt, Tsien, "Improved green fluorescence," *Nature*, 373:663–664, 1995.
Heim, Prasher, Tsien, "Wavelength mutations and posttranslational autoxidation of green fluorescent protein," *Proc. Natl. Acad. Sci., USA*, 91:12501–12504, 1994.
Hemenway et al., *The EMBO J.*, 7:1273–1280, 1988.
Hilder et al., *Nature*, 330:160–163, 1987.
Hinchee et al., *Bio/technol.*, 6:915–922, 1988.
Hu and Cheng, "Expression of Aequorea green fluorescent protein in plant cells," *FEBS Lett.*, 369:331–334, 1995.
Hudspeth and Grula, *Plant Mol. Biol.*, 12:579–589, 1989.
Ikeda et al., *J Bacteriol*, 169:5615–5621, 1987.
Jefferson, Kavanagh, Bevan, "GUS fusions: β-glucuronidase as a sensitive and versatile gene fusion marker in higher plants," *The EMBO Journal*, 6(13) :3901–3907, 1987.

Johnson et al., *Proc. Natl. Acad. Sci., USA*, 86:9871–9875, 1989.
Joshi, *Nucleic Acids Res.*, 15:6643–6653, 1987.
Kaasen et al., *J. Bacteriology*, 174:889–898, 1992.
Kaeppler et al. (1990) *Plant Cell Reports*, 9: 415–418.
Kaether and Gerdes, "Visualization of protein transport along the secretory pathway using green fluorescence protein," *FEBS Lett.*, 369:267–271, 1995.
Karsten et al., *Botanica Marina*, 35:11–19, 1992.
Keller et al., *EMBO J.*, 8:1309–14, 1989.
Klein et al., *Nature*, 327:70, 1987.
Koster et al., *Plant Physiol.*, 88:829–832, 1988.
Kwoh et al., *Proc. Nat. Acad. Sci., USA*, 86: 1173, 1989.
Langridge et al., *Proc. Natl. Acad. Sci,. USA*, 86:3219–3223, 1989.
Lawton et al., *Plant Mol. Biol.*, 9:315–324, 1987.
Lee and Huang, "Genes encoding oleosins in maize kernel of inbreds Mo17 and B73," *Plant Molecular Biology*, 26:1981–1987, 1994.
Lee and Saier, *J. Bacteriol*, 153–685, 1983.
Leff and Leff, "Use of green fluorescent protein to monitor survival of genetically engineered bacteria in aquatic environments," *Appl. Environ. Microbiol.*, 62:3486–3488, 1996.
Levings, *Science*, 250: 942–947, 1990.
Lindstrom et al., *Developmental Genetics*, 11:160, 1990.
Loomis et al., *J. Expt. Zoology*, 252:9–15, 1989.
Lorz et al.,*Mol. Gen. Genet.*, 199:178, 1985.
Lybarger, Dempsey, Franek, Chervenak, "Rapid Generation and Flow Cytometric Analysis of Stable GFP-Expressing Cells," *Cytometry*, 25:211–220, 1996.
Ma, J. et al., *Nature*, 334:631–633, 1988.
Marcotte et al., *Nature*, 335:454, 1988.
Mariani et al., *Nature*, 347:737–741, 1990.
McElroy, Zhang, Cao, Wu, "Isolation of an efficient actin promoter for use in rice transformation," *Plant Cell*, 2(2):163–171, 1990.
Millar, Carre, Strayer, Chua, Kay, "The regulation of circadian period by phototransduction pathways in Arabidopsis," *Science*, 267:1161–1163, 1995.
Mundy and Chua, *The EMBO J.*, 7: 2279–2286, 1988.
Murakami et al., *Mol Gen Genet*, 205:42–50, 1986.
Murashige and Skoog, *Physiol Plant*, 15:473–497, 1962.
Murdock et al., *Phytochemistry*, 29:85–89, 1990.
Napoli et al., *Plant Cell*, 2:279–289, 1990.
Nester et al., *Ann. Rev. Plant Physiol*, 35:387–413, 1984.
Odell et al., *Nature*, 313:810, 1985.
Ogawa et al., *Sci. Rep.*, 13:42–48, 1973.
Ohara et al., *Proc. Natl. Acad. Sci. USA*, 86:5673–5677, 1989.
Omirulleh et al., *Plant Molecular Biology*, 21:415–428, 1993.
Ow, Wood, Deluca, de Wet, Helinski, Howell, "Transient and stable expression of the firefly luciferase gene in plant cells and transgenic plants," *Science*, 234:856–859, 1986.
Pang, DeBoer, Wan, Ye, Layton, Neher, Armstrong, Fry, Hinchee, Fromm, "An improved green fluorescent protein gene as a vital marker in plants," *Plant Physiol.*, 112:893–900, 1996.
Pease et al., Light-generated oligonucleotide arrays for rapid DNA sequence analysis. *Proc. Natl. Acad Sci., USA*, 91:5022–5026, 1994.
Perlak et al., *Proc. Natl. Acad. Sci., USA*, 88:3324–3328, 1991.
Phi-Van, L., Kries, J. P., Ostertag, W., Stratling, W. H. (1990), *Mol. Cell. Biol.*, 10:2302–2307.
Piatkowski et al., *Plant Physiol.*, 94:1682–1688, 1990.
Pignon et al., *Hum. Mutat.*, 3: 126–132, 1994.
Plautz, Day, Dailey, Welsh, Hall, Halpain, Kay, "Green fluorescent protein and its derivatives as versatile markers for gene expression in living *Drosophila melanogaster*, plant and mammalian cells," *Gene*, 173:83–87, 1996.
Poszkowski et al., *EMBO J.*, 3:2719, 1989.
Potrykus et al., *Mol. Gen. Genet.*, 199:183, 1985.
Poulsen et al., *Mol. Gen. Genet.*, 205:193–200, 1986.
Prasher, Eckenrode, Ward, Prendergrast, Cormier, "Primary structure of the Aequorea Victoria green fluorescent protein," *Gene*, 111:229–233, 1992.
Reed et al., *J. Gen. Microbiology*, 130:1–4, 1984.
Reichel, Mathur, Eckes, Langenkemper, Koncz, Schell, Reiss, Maas, "Enhanced green fluorescence by the expression of an Aequorea victoria green fluorescent protein mutant in mono- and dicotyledonous plant cells," *Proc. Natl. Acad Sci., USA*, 93:5888–5893, 1996.
van Rensburg et al., *J. Plant Physiol*, 141:188–194, 1993.
Rhodes et al., *Science*, 240:204–207, 1988.
Sambrook et al., Molecular Cloning, A Laboratory Manual, 2nd ed., 1989.
Shagan and Bar-Zvi, *Plant Physiol.*, 101:1397–1398, 1993.
Shapiro, Mobile Genetic Elements, Academic Press, N.Y., 1983.
Sheen, Hwang, Niwa, Kobayashi, Galbraith, "Green fluorescent protein as a new vital marker in plant cells," *Plant J.*, 8(5):777–784, 1995.
Shoemaker et al., Quantitative phenotypic analysis of yeast deletion mutants using a highly parallel molecular barcoding strategy. *Nature Genetics* 14:450–456, 1996.
Siemering, Golbik, Sever, Haseloff, "Mutations that suppress the thermosensitivity of green fluorescent protein," *Curr. Biol.*, 6:1653–1663, 1996.
Simpson, *Science*, 233:34, 1986.
Skriver and Mundy, *Plant Cell*, 2:503–512, 1990.
Smith et al., *EMBO J.*, 9,741, 1990.
Spellig, Bottin, Kahmann, "Green fluorescent protein (GFP) as a new vital marker in the phytopathogenic fungus Ustilago maydis," *Mol. Gen. Genet.*, 252:503–509, 1996.
Sprague G. and Dudley J. W. (eds.), "Corn and Improvement", Third Ed., *American Society of Agronomy*, 1988.
Stalker et al., *J. Biol. Chem.*, 263:6310–6314, 1988.
Stief et al., *Nature*, 341:343, 1989.
Stougaard, *The Plant Journal*, 3:755–761, 1993.
Sullivan et al., *Mol. Gen. Genet*, 215:431–440, 1989.
Tarczynski et al., *Proc. Natl. Acad. Sci., USA*, 89:2600, 1992.
Tarczynski et al., *Science*, 259:508–510, 1993.
Thillet et al., *J. Biol. Chem.*, 263:12500–12508, 1988.
Thompson et al., *EMBO J.*, 6:2519–2623, 1987.
Tian, Sequin, Charest, "Expression of the green fluorescent protein gene in conifer tissues," *Plant Cell Rep.*, 16:267–271, 1997.
Toriyama et al., *Theor Appl. Genet.*, 73:16, 1986.
Uchimiya et al., *Mol. Gen. Genet.*, 204:204, 1986.
Vaeck, Reynaerts, Hofte, Jansens, DeBeuckeleer, Dean, Zabeau, VanMontagu, Leemans, *Nature* (London), 328:33–37, 1987.
Van der Krol et al., *Plant Cell*, 2:291–299, 1990.
Van Tunen et al., *EMBO J.*, 7:1257, 1988.
Vasil et al., *Plant Physiol.*, 91:1575–1579, 1989.
Vasil et al., *Plant Physiol.*, 91:1575–1579, 1989.
Vernon and Bohnert, *The EMBO, J.*11:2077–2085, 1992.
Vodkin et al., *Cell*, 34:1023, 1983.
Vogel et al., *J. Cell Biochem.*, 13D(Supp):312, 1989.
Wada, K-n., Aota, S-i., Tsuchiya, R., Ishibashi, F., Gojobori, T. and Ikemura, T., "Codon usage tabulated from the GenBank genetic sequence data," *Nucleic Acids Res.* 18:2367–2411, 1990.
Walker et al., *Proc. Natl. Acad. Sci., USA,* 84:6624–6628, 1987.
Walker et al., *Proc. Natl. Acad. Sci., USA,* 89:392–396 1992.
Wang et al., *Molecular and Cellular Biology,* 12:3399–3406, 1992.
Watrud et al., in *Engineered Organisms and the Environment,* H. O. Halvorson et al., eds., Am. Soc. Microbiol., Washington, D.C., 1985.
Watson S. and Ramstad P. E. (eds), "Corn: Chemistry and Technology", *American Association of Cereal Chemists,* 1987.
Wenzler et al., *Plant Mol. Biol.,* 12:41–50, 1989.
Withers and King, *Plant Physiol,* 64:675–687, 1979.
Wolter et al., *The EMBO J.,* 4685–4692, 1992.
Wu et al., *Genomics,* 4:560,1989.
Xiang and Guerra, *Plant Physiol.,* 102:287–293, 1993.
Xu et al., *Plant Physiol.,* 110: 249–257, 1996.
Yamada et al., *Plant Cell Rep.,* 4:85, 1986.
Yamaguchi-Shinozaki et al. *Plant Cell Physiol.,* 33:217–224, 1992.
Yang et al., *Proc. Natl. Acad. Sci., USA,* 87:4144–48,1990.
Yang, Cheng, Kain, "Optimized codon usage and chromophore mutations provide enhanced sensitivity with the green fluorescent protein," *Nucleic Acid Res.,* 24:4592–4593, 1996.
Zolotukhin, Potter, Hauswirth, Guy, Muzyczka, "A 'humanized' green fluorescent protein cDNA adapted for high level expression in mammalian cells," *J. Virol.,* 70:4646–4654, 1996.

What is claimed is:

1. A construct comprising a gene fusion between a selectable marker gene and a screenable marker gene, wherein said gene fusion is operably linked to an aleurone-specific promoter and wherein said screenable marker is further defined as capable of detection by non-destructive assay.

2. The construct of claim 1, wherein said screenable marker gene is selected from the group consisting of a GFP gene, a luciferase gene, and an R gene.

3. The construct of claim 2, wherein said selectable marker gene comprises a gene selected from the group consisting of NPTII, bar, EPSPS, anthranalite synthase and dalapon dehalogenase.

4. The construct of claim 1, wherein said promoter is selected from the group consisting of an oleosin promoter, globulin 1 promoter, barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter.

5. The construct of claim 4, wherein said oleosin promoter is an L3 oleosin promoter.

6. The construct of claim 1, further comprising a second gene.

7. The construct of claim 6, wherein said second gene is selected from the group consisting of an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

8. The construct of claim 7, wherein said second gene is operably linked to a second promoter.

9. A transgenic plant comprising a gene fusion between a selectable marker gene and a screenable marker gene, wherein said gene fusion is operably linked to an aleurone-specific promoter and wherein said screenable marker is further defined as capable of detection by non-destructive assay.

10. The transgenic plant of claim 9, wherein said screenable marker gene is selected from the group consisting of a GFP gene, a luciferase gene, and an R gene.

11. The transgenic plant of claim 10, wherein said screenable marker is a GFP gene.

12. The transgenic plant of claim 9, wherein said selectable marker gene is selected from the group consisting of NPTII, bar, EPSPS, anthranalite synthase and dalapon dehalogenase.

13. The transgenic plant of claim 9, wherein said aleurone-specific promoter is selected from the group consisting of an oleosin promoter, globulin 1 promoter, barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter.

14. The transgenic plant of claim 13, wherein said oleosin promoter is an L3 oleosin promoter.

15. The transgenic plant of claim 9, further defined as a monocotyledonous plant.

16. The transgenic plant of claim 15, wherein said monocotyledonous plant is selected from the group consisting of maize, rice, wheat, barley, oat, rye, millet, sorghum, sugarcane and turfgrass.

17. The transgenic plant claim 16, wherein said monocotyledonous plant is maize.

18. The transgenic plant of claim 9, further defined as a dicotyledonous plant.

19. The transgenic plant of claim 18, wherein said dicotyledonous plant is selected from the group consisting of cotton, soybean, tomato, potato, citrus, and tobacco.

20. The plant of claim 19, wherein the dicotyledonous plant is soybean.

21. A progeny plant of any generation of the transgenic plant of claim 9, wherein said progeny plant comprises said gene fusion.

22. A method of identifying transgenic seeds comprising the steps of:
 (a) obtaining a transgenic plant, the cells of which comprise a gene fusion between a selectable marker gene and a screenable marker gene, wherein said gene fusion is operably linked to an aleurone-specific promoter;
 (b) cultivating said transgenic plant until seed set;
 (c) collecting seeds produced on said transgenic plant; and
 (d) screening said seeds based on a phenotype conferred upon the seeds by said screenable marker gene.

23. The method of claim 22, wherein said screenable marker gene is selected from the group consisting of a GFP gene, a luciferase gene, and an R gene.

24. The method of claim 23, wherein said screenable marker is a GFP gene.

25. The method of claim 22, wherein said transgenic plant is a monocotyledonous plant.

26. The method of claim 25, wherein said monocotyledonous plant is selected from the group consisting of maize, rice, wheat, barley, oat, rye, millet, sorghum, sugarcane and turfgrass.

27. The method of claim 26, wherein said monocotyledonous plant is maize.

28. The method of claim 22, wherein said transgenic plant is a dicotyledonous plant.

29. The method of claim 28, wherein said dicotyledonous plant is selected from the group consisting of cotton, soybean, tomato, potato, citrus, and tobacco.

30. The method of claim 29, wherein the dicotyledonous plant is soybean.

31. The method of claim 22, wherein said transgenic plant further comprises an exogenous gene encoding a selected trait, wherein said exogenous gene is genetically linked to said gene fusion.

32. The method of claim 31, wherein said exogenous gene comprises a second promoter operatively linked to said exogenous gene.

33. The method of claim 31, wherein said exogenous gene encodes a trait selected from the group consisting of an insect resistance gene, a viral disease resistance gene, a bacterial disease resistance gene, a fungal disease resistance gene, a nematode disease resistance gene, a herbicide resistance gene, a nematode disease resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

34. The method of claim 22, wherein said gene fusion comprises a 3' region operatively linked to said gene fusion.

35. The method of claim 22, wherein said gene fusion comprises an element enhancing the expression of said gene fusion.

36. The method of claim 22, wherein said screening is automated.

37. A method of plant breeding comprising the steps of:
 (a) obtaining first and second plants, wherein cells of one or both of said first or second plants comprise a gene encoding a screenable marker operably linked to an aleurone-specific promoter, wherein said screenable marker gene is fused to a selectable marker gene and wherein said screenable marker is further defined as capable of detection by non-destructive assay;
 (b) crossing said first and second plants; and
 (c) collecting the seeds resulting from said crossing.

38. The method of claim 37, further comprising the step of:
 (d) selecting transgenic seeds from collected seeds based on a phenotype conferred upon said transgenic seeds by said screenable marker gene.

39. The method of claim 37, wherein said screenable marker gene is selected from the group consisting of a GFP gene, a luciferase gene, and an R gene.

40. The method of claim 39, wherein said screenable marker is a GFP gene.

41. The method of claim 37, wherein said selectable marker gene comprises a gene selected from the group consisting of NPTII, bar, EPSPS, anthranalite synthase and dalapon dehalogenase.

42. The method of claim 37, wherein said promoter is selected from the group consisting of an oleosin promoter, globulin 1 promoter, barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter.

43. The method of claim 42, wherein said promoter is an oleosin promoter.

44. The method of claim 43, wherein said oleosin promoter is an L3 oleosin promoter.

45. The method of claim 42, wherein said promoter is a globulin 1 promoter.

46. The method of claim 42, wherein said promoter is a barley LTP2 promoter.

47. The method of claim 37, wherein said first and second transgenic plants are monocotyledonous plants.

48. The method of claim 47, wherein said monocotyledonous plants are selected from the group consisting of maize, rice, wheat, barley, oat, rye, millet, sorghum, sugarcane and turfgrass.

49. The method of claim 48, wherein said monocotyledonous plants are maize plants.

50. The method of claim 37, wherein said first and second transgenic plants are dicotyledonous plants.

51. The method of claim 50, wherein said dicotyledonous plants are selected from the group consisting of cotton, soybean, tomato, potato, citrus, and tobacco.

52. The method of claim 51, wherein the dicotyledonous plants are soybean plants.

53. The method of claim 38, wherein said selecting is automated.

54. A method of plant breeding comprising the steps of:
   (a) obtaining a transgenic plant, the cells of which comprise a gene encoding a screenable marker operably linked to an aleurone-specific promoter, wherein said screenable marker gene is fused to a selectable marker gene and wherein said screenable marker is further defined as capable of detection by non-destructive assay;
   (b) allowing said plant to self fertilize; and
   (c) collecting the seeds produced on said plant.

55. The method of claim 54, further comprising the step of:
   (d) selecting transgenic seeds from said collected seeds based on the phenotype conferred upon said transgenic seeds by said screenable marker gene.

56. The method of claim 54, wherein said screenable marker gene is selected from the group consisting of a GFP gene, a luciferase gene, and an R gene.

57. The method of claim 56, wherein said screenable marker is a GFP gene.

58. The method of claim 54, wherein said selectable marker gene comprises a gene selected from the group consisting of NPTII, bar, EPSPS, anthranalite synthase and dalapon dehalogenase.

59. The method of claim 54, wherein said promoter is selected from the group consisting of an oleosin promoter, globulin 1 promoter, barley LTP2 promoter, alpha-amylase promoter, chitinase promoter, beta-glucanase promoter, cysteine proteinase promoter, glutaredoxin promoter, HVA1 promoter, serine carboxypeptidaseII promoter, catalase promoter, alpha-glucosidase promoter, beta-amylase promoter, VP1 promoter, and bronze2 promoter.

60. The method of claim 59, wherein said oleosin promoter is an L3 oleosin promoter.

61. The method of claim 59, wherein said promoter is a globulin 1 promoter.

62. The method of claim 59, wherein said promoter is a barley LTP2 promoter.

63. The method of claim 54, wherein said transgenic plant is a monocotyledonous plant.

64. The method of claim 63, wherein said monocotyledonous plant is selected from the group consisting of maize, rice, wheat, barley, oat, rye, millet, sorghum, sugarcane and turfgrass.

65. The method of claim 64, wherein said monocotyledonous plant is a maize plant.

66. The method of claim 54, wherein said transgenic plant is a dicotyledonous plant.

67. The method of claim 66, wherein said dicotyledonous plant is selected from the group consisting of cotton, soybean, tomato, potato, citrus, and tobacco.

68. The method of claim 67, wherein the dicotyledonous plant is a soybean plant.

69. The method of claim 55, wherein said step of selecting is automated.

* * * * *